United States Patent [19]

Tsubotani et al.

[11] Patent Number: 5,668,128
[45] Date of Patent: Sep. 16, 1997

[54] AZIRIDINE DERIVATIVES, THEIR PRODUCTION AND USE

[75] Inventors: Shigetoshi Tsubotani; Masayuki Takizawa; Mikio Shirasaki, all of Ibaraki; Junji Mizoguchi, Osaka; Yoshiaki Shimizu, Ibaraki, all of Japan

[73] Assignee: Takeda Chemical Industries, Ltd., Osaka, Japan

[21] Appl. No.: 513,896

[22] PCT Filed: Apr. 12, 1995

[86] PCT No.: PCT/JP95/00718
  § 371 Date: Sep. 5, 1995
  § 102(e) Date: Sep. 5, 1995

[87] PCT Pub. No.: WO95/28416
  PCT Pub. Date: Oct. 26, 1995

[30] Foreign Application Priority Data

Apr. 13, 1994 [JP] Japan .................... 6-074621
Nov. 1, 1994 [JP] Japan .................... 6-269175

[51] Int. Cl.$^6$ .................... C07D 203/16; C07D 413/00; A61K 31/33; A61K 31/535
[52] U.S. Cl. .................... 514/183; 514/235.5; 514/326; 514/336; 514/371; 514/422; 544/111; 546/208; 546/268.1; 548/195; 548/518; 548/966

[58] Field of Search .................... 548/966, 195, 548/518; 514/183, 235.5, 326, 336, 371, 422; 544/111; 546/208, 268.1

[56] References Cited

U.S. PATENT DOCUMENTS 4,418,075  11/1983  Tamai et al. .................... 424/278

FOREIGN PATENT DOCUMENTS

4142958A1  7/1993  Germany .

Primary Examiner—Mukund J. Shah
Assistant Examiner—Brenda Coleman
Attorney, Agent, or Firm—Wenderoth, Lind & Ponack

[57] ABSTRACT

The present invention relates to a compound of the formula:

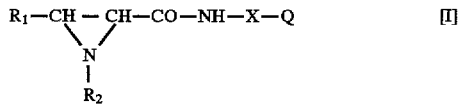

wherein $R_1$ and Q are independently an optionally esterified or amidated carboxyl group; $R_2$ is hydrogen, an acyl group or an optionally substituted hydrocarbon residue; X is a divalent hydrocarbon residue which may be substituted; or a salt thereof, which is useful as prophylactic and therapeutic agents of bone diseases and as agents for inhibiting thiol protease.

37 Claims, No Drawings

AZIRIDINE DERIVATIVES, THEIR PRODUCTION AND USE

BACKGROUND OF THE INVENTION

1. Field of the Invention

This invention relates to novel aziridinedicarboxylic acid derivatives, which are useful as a prophylactic and therapeutic agent of bone diseases and an agent of inhibiting thiol protease.

2. Description of Related Art

In bone tissue, bone resorption and formation occur constantly with a good balance to ensure bone homeostasis; bone diseases such as osteoporosis are caused when the balance shifts to the bone resorption side. In recent years, various epoxy compounds possessing prophylactic and therapeutic activity against bone diseases have been reported [JPA H2(1990)-218610, EP-A 269311].

However, aziridinedicarboxylic acid derivatives having prophylactic and therapeutic activity against bone diseases and activity of inhibiting thiol protease have not been reported yet.

Currently, bone resorption suppressors such as estrogens and calcitonin are used for the prophylaxis and therapy of bone diseases such as osteoporosis. However, in the case of administration of these therapeutic agents, subjects to be administered are limited and their efficacy is uncertain in some instances, and satisfactory effects have not yet been brought about. And, at the present stage, compounds showing satisfactory inhibiting action against thiol protease secreted from lysosome of osteoclasts have not yet been available.

SUMMARY OF THE INVENTION

With the above situation in mind, the present inventors paid attention to thiol protease, especially cathepsin L [H. Kakegawa et al., FEBS Letters, Vol.321,p.247 (1993)], which has recently been shown to play a major role in bone resorption, and they conducted diligent study and found that novel aziridinedicarboxylic acid derivatives show potent actions of inhibiting cathepsin L and further of suppressing bone resorption.

Based on these findings, the present inventors have made further study to accomplish the invention.

According to the present invention, there is provided:
(1) A compound of the formula:

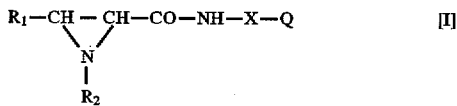

wherein $R_1$ and Q are independently an optionally esterified or amidated carboxyl group; $R_2$ is hydrogen, an acyl group or an optionally substituted hydrocarbon residue; X is a divalent hydrocarbon residue which may be substituted; or a salt thereof, (2) A compound or a salt thereof according to term (1) above, wherein the salt is a pharmaceutically acceptable salt, (3) The compound according to term (1) above, wherein Q is a group of the partial structural formula: —CO— N($R_3$)($R_4$) wherein $R_3$ and $R_4$ are independently hydrogen, an optionally substituted hydrocarbon residue or an optionally substituted heterocyclic group; or $R_3$ and $R_4$ are combined with the adjacent nitrogen atom to represent an optionally substituted heterocyclic group, (4) The compound according to term (3) above, wherein $R_3$ and $R_4$ are independently hydrogen or an optionally substituted hydrocarbon residue; or $R_3$ and $R_4$ are combined with the adjacent nitrogen atom to represent an optionally substituted heterocyclic group, (5) The compound according to term (1) above, wherein $R_1$ is an optionally esterified carboxyl group, (6) The compound according to term (1) above, wherein $R_2$ is hydrogen or an acyl group, (7) The compound according to term (1) above, wherein $R_2$ is hydrogen, (8) The compound according to term (3) above, wherein the partial structural formula: —NH—X—CO— is an α-amino acid residue, (9) The compound according to term (8) above, wherein the α-amino acid residue is of L-configuration,

(10) The compound according to term (8) above, wherein the α-amino acid residue is an aromatic amino acid residue,

(11) The compound according to term (3) above, wherein either $R_3$ or $R_4$ is hydrogen and the other is an optionally substituted hydrocarbon residue,

(12) The compound according to term (11) above, wherein the hydrocarbon residue is an alkyl group,

(13) The compound according to term (11) above, wherein the hydrocarbon residue is an aralkyl group,

(14) The compound according to term (3) above, wherein $R_3$ and $R_4$ are combined with the adjacent nitrogen atom to represent an optionally substituted heterocyclic group,

(15) The compound according to term (14) above, wherein the heterocyclic group is a 6-membered heterocyclic group,

(16) The compound according to term (1) above, wherein the compound is N-[N-[(2S,3S)-3-ethoxycarbonylaziridine-2-carbonyl]-L-phenylalanyl]-2-phenylethylamine,

(17) The compound according to term (1) above, wherein the compound is N-[N-[(2S,3S)-3-ethoxycarbonylaziridine-2-carbonyl]-L-phenylalanyl]isopentylamine,

(18) The compound according to term (1) above, wherein the compound is N-[N-[(2S,3S)-3-ethoxycarbonylaziridine-2-carbonyl]-L-phenylalanyl]-3-methoxypropylamine,

(19) The compound according to term (1) above, wherein the compound is N-[N-[(2S,3S)-3-ethoxycarbonylaziridine-2-carbonyl]-L-phenylalanyl]-N-methyl-2-phenylethylamine,

(20) A composition for inhibition of a thiol protease, which comprises a compound or a salt thereof as defined in term (1) above,

(21) A pharmaceutical composition for preventing or treating a bone disease, which comprises a compound or a pharmaceutical acceptable salt thereof as defined in term (2) above,

(22) The pharmaceutical composition according to term (21) above, wherein the bone disease is osteoporosis,

(23) Use of a compound according to term (1) above, for the manufacture of a medicament for inhibition of a thiol protease,

(24) Use of a compound according to term (1) above, for the manufacture of a medicament for preventing or treating a bone disease,

(25) The use according to term (24) above, wherein the bone disease is osteoporosis,

(26) A method for inhibiting a thiol protease in a mammal, which comprises administering an effective amount of the compound or a pharmaceutically acceptable salt thereof as defined in term (2) above, to the mammal,

(27) A method for preventing or treating a bone disease in a mammal, which comprises administering an effective amount of the compound or a pharmaceutically acceptable salt thereof as defined in term (2) above, to the mammal,

(28) The method according to term (27) above, wherein the bone disease is osteoporosis, and

(29) The compound according to term (1) above, wherein Q is a carboxyl group.

DETAILED DESCRIPTION OF THE INVENTION

Abbreviations for amino acids, peptides and others used in the present specification are based on those specified by the IUPAC-IUB Commission on Biochemical Nomenclature or those in conventionally used in relevant fields. When an optical isomer is present in amino acid, it is of the L-configuration, unless otherwise specified.

With respect to the general formula [I], as optionally esterified carboxyl groups represented by $R_1$ and Q, use is made of, for example, pharmaceutically acceptable ones or those which convert to pharmaceutically acceptable ones in vivo. Preferable examples of esterified carboxyl group are represented by the formula —$COOR_5$, wherein $R_5$ is an optionally substituted hydrocarbon residue. $R_5$ is exemplified by (1) $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.) optionally having 1 to 3 substituents selected from (a) nitro group, (b) halogen atom (e.g. fluorine, chlorine, bromine and iodine) and (c) $C_{1-6}$ alkanoyloxy group (e.g. formyloxy, acetyloxy, propionyloxy, isopropionyloxy, butyryloxy, isobutyryloxy, valeryloxy, isovaleryloxy, pivaloyloxy, hexanoyloxy, etc.), (2) $C_{6-14}$ aryl groups (e.g. phenyl, naphthyl, etc.) optionally having 1 to 3 substituents selected from (a) nitro group, (b) halogen atom (e.g. fluorine, chlorine, bromine and iodine) and (c) $C_{1-4}$ alkoxy group (e.g. methoxy, ethoxy, propoxy, isopropoxy, butoxy, isobutoxy, sec-butoxy, tert-butoxy, etc.), and (3) $C_{7-12}$ aralkyl groups (e.g. benzyl, phenethyl, etc.) optionally having 1 to 3 substituents selected from (a) nitro group, (b) halogen atoms (e.g. fluorine, chlorine, bromine and iodine) and (c) $C_{1-4}$ alkoxy groups (e.g. methoxy, ethoxy, propoxy, isopropoxy, butoxy, isobutoxy, sec-butoxy, tert-butoxy, etc.).

Preferable examples of $R_5$ include $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, hexyl, etc.) optionally having 1 to 3 substituents selected from (a) nitro group, (b) halogen atoms (e.g. fluorine, chlorine, bromine and iodine) and (c) $C_{1-6}$ alkanoyloxy groups (e.g. formyloxy, acetyloxy, propionyloxy, isopropionyloxy, butyryloxy, valeryloxy, isovaleryloxy, pivaloyloxy, hexanoyloxy, etc.).

More preferable examples of $R_5$ include $C_{1-5}$ alkyl groups (e.g. methyl, ethyl, propyl, isopropyl, butyl, isobutyl, sec-butyl, tert-butyl, pentyl, isopentyl, sec-pentyl, neopentyl, tert-pentyl, etc.)

As the amidated carboxyl group represented by $R_1$ and Q in general formula [I], use is made of, for example, pharmaceutically acceptable ones or those which convert to pharmaceutically acceptable ones in vivo. Preferable amidated carboxyl groups for $R_1$ are represented by the formula —$CONHR_6$, wherein $R_6$ is hydrogen or an optionally substituted hydrocarbon residue. More specifically, $R_6$ is, for example, (1) hydrogen, (2) $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl and hexyl) optionally having 1 to 3 substituents selected from (a) nitro group and (b) halogen atoms (e.g. fluorine, chlorine, bromine and iodine), (3) $C_{6-14}$ aryl groups (e.g. phenyl and naphthyl) optionally having 1 to 3 substituents selected from (a) nitro group, (b) halogen atoms (e.g. fluorine, chlorine, bromine and iodine) and (c) $C_{1-4}$ alkoxy groups (e.g. methoxy, ethoxy, propoxy, isopropoxy, butoxy, isobutoxy, sec-butoxy and tert-butoxy), and (4) $C_{7-12}$ aralkyl groups (e.g. benzyl and phenethyl) optionally hating 1 to 3 substituents selected from (a) nitro group, (b) halogen atoms (e.g. fluorine, chlorine, bromine and iodine) and (c) $C_{1-4}$ alkoxy groups (e.g. methoxy, ethoxy, propoxy, isopropoxy, butoxy, isobutoxy, sec-butoxy and tert-butoxy).

Preferable examples of $R_6$ include $C_{1-6}$ alkyl groups (e.g. methyl, ethyl, propyl, isopropyl, butyl, isobutyl, sec-butyl, tert-butyl, pentyl, isopentyl, sec-pentyl, neopentyl, tert-pentyl and hexyl) optionally having 1 to 3 substituents selected from (a) nitro group and (b) halogen atoms (e.g. fluorine, chlorine, bromine and iodine).

More preferable examples of $R_6$ include $C_{1-5}$ alkyl groups (e.g. methyl, ethyl, propyl, isopropyl, butyl, isobutyl, sec-butyl, tert-butyl, pentyl, isopentyl, sec-pentyl, neopentyl and tert-pentyl).

The amidated carboxyl group represented by Q is primary amide or secondary amide. The amidated carboxyl group is preferably represented by the partial structural formula: —$CON(R_3)R_4$ wherein $R_3$ and $R_4$ are independently hydrogen, an optionally substituted hydrocarbon residue or an optionally substituted heterocyclic group; or $R_3$ and $R_4$ are combined with the adjacent nitrogen atom to represent an optionally substituted heterocyclic group.

The optionally substituted hydrocarbon residues represented by $R_3$ and $R_4$ have the same meaning as that of $R_2$ described hereinafter.

As the optionally substituted heterocyclic group represented by $R_3$ and $R_4$, use is made of, for example, 5- to 6-membered heterocyclic groups containing, besides carbon atoms, 1 to 4 hetero atoms such as oxygen atom, sulfur atom and nitrogen atom, or condensed heterocyclic groups thereof (e.g. 2- or 3-thienyl, 2- or 3-furyl, 1-, 2- or 3-pyrrolyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl, indolyl, piperidino, morpholino).

Such heterocyclic groups as above may optionally have, at any possible positions, 1 to 5 substituents selected from, for example, (1) $C_{1-4}$ alkyl groups (e.g. methyl, ethyl, propyl, isopropyl, butyl, isobutyl, sec-butyl and tert-butyl), (2) $C_{6-14}$ aryl groups (e.g. phenyl and naphthyl) optionally having 1 to 4 substituents selected from (a) nitro group, (b) halogen atoms (e.g. bromine, chlorine, fluorine and iodine), (c) $C_{1-4}$ alkyl groups (e.g. methyl, ethyl, propyl, isopropyl, butyl, isobutyl, sec-butyl and tert-butyl) and (d) $C_{1-4}$ alkoxy groups (e.g. methoxy, ethoxy, propoxy, isopropoxy, butoxy, isobutoxy, sec-butoxy and tert-butoxy), (3) $C_{7-12}$ aralkyl groups (e.g. benzyl and phenethyl) optionally having 1 to 4 substituents selected from (a) nitro group, (b) halogen atoms (e.g. fluorine, chlorine, bromine and iodine), (c) $C_{1-4}$ alkyl groups (e.g. methyl, ethyl, propyl, isopropyl, butyl, isobutyl, sec-butyl, tert-butyl) and (d) $C_{1-4}$ alkoxy groups (e.g. methoxy, ethoxy, propoxy, isopropoxy, butoxy, isobutoxy, sec-butoxy and tert-butoxy), (4) hydroxyl group optionally having substituent selected from (a) $C_{1-4}$ alkyl groups (e.g. methyl, ethyl, propyl, isopropyl, butyl, isobutyl, sec-butyl and tert-butyl), (b) $C_{7-12}$ aralkyl groups (e.g. benzyl and phenethyl), (c) $C_{1-6}$ alkanoyl groups (e.g. formyl, acetyl, propionyl, isopropionyl, butyryl, isobutyryl, valeryl, isovaleryl, pivaloyl and hexanoyl) and (d) $C_{7-11}$ aroyl groups (e.g. benzoyl, p-toluoyl, 1-naphthoyl and 2-naphthoyl), (5) carboxyl group, (6) carbamoyl group, (7) $C_{2-5}$ alkoxycarbonyl groups (e.g. methoxycarbonyl and ethoxycarbonyl), (8) $C_{8-14}$ aralkyloxycarbonyl groups (e.g. benzyloxycarbonyl), (9) nitro group, and (10) halogen atoms (e.g. fluorine, chlorine, bromine and iodine).

In the present invention, the compound, wherein either $R_3$ or $R_4$ is hydrogen and the other is an optionally substituted hydrocarbon residue, is preferably used. The compound, wherein either $R_3$ or $R_4$ is hydrogen and the other is an optionally substituted alkyl or aralkyl group, is more preferably used.

As the optionally substituted heterocyclic group, wherein $R_3$ and $R_4$ are combined with the adjacent nitrogen atom, use is made of, for example, 5- to 8-membered heterocyclic groups optionally containing, besides nitrogen atoms, 1 to 3 hetero-atoms such as oxygen atom, sulfur atom and nitrogen atom, or condensed heterocyclic groups thereof. Specific examples of them include (1) 5-membered heterocyclic groups optionally containing, besides nitrogen atom, 1 to 3 hetero-atoms selected from oxygen atom, sulfur atom and nitrogen atom, (e.g. 1-pyrrolidinyl, 2-pyrrolin-1-yl, 1,3-diazacyclopentan-1-yl, 1-aza-3-oxacyclopentan-1-yl, 1-aza-3-thiacyclopentan-1-yl, pyrazolyl, pyrazolidinyl, 3-pyrazolin-2-yl, 2-imidazolidin-1-yl, 1,2,3-triazolyl, 1,2,4-triazolyl and 1H- or 2H-tetrazolyl), (2) 6-membered heterocyclic groups optionally containing, besides nitrogen atom, one or two hetero-atoms selected from oxygen atom, sulfur atom and nitrogen atom, (e.g. piperidino, thiomorpholino, morpholino, piperazinyl, 4H-1,4-oxazinyl and 4H-1,4-thiazinyl), and (3) bicyclic or tricyclic condensed heterocyclic groups optionally containing, besides nitrogen atom, one or two hetero-atoms selected from oxygen atom, sulfur atom and nitrogen atom, (e.g. 1H-indazol-1-yl, purin-1-yl, phenothiazin-10-yl, phenoxazin-10-yl and indolyl).

Preferable heterocyclic groups include 6-membered heterocyclic groups optionally containing, besides nitrogen atom, one or two hetero-atoms selected from oxygen atom, sulfur atom and nitrogen atom, (e.g. piperidino, thiomorpholino, morpholino, piperazinyl, 4H-1,4-oxazinyl and 4H-1,4-thiazinyl).

Such heterocyclic groups as above may optionally have, at any possible positions, 1 to 5 substituents which have the same meaning as the substituents in the optionally substituted heterocyclic group represented by $R_3$ and $R_4$.

With respect to general formula [I], $R_1$ is preferably an optionally esterified carboxyl group.

More preferably, $R_1$ is a carboxyl group optionally esterified with a $C_{1-6}$ alkyl group optionally having 1 to 3 substituents selected from (a) nitro group, (b) halogen atoms (e.g. fluorine, chlorine, bromine and iodine) and (c) $C_{1-6}$ alkanoyloxy groups (e.g. formyloxy, acetyloxy, propionyloxy, isopropionyloxy, butyryloxy, isobutyryloxy, valeryloxy, isovaleryloxy, pivaloyloxy and hexanoyloxy).

Especially preferable examples of $R_1$ include a carboxyl group esterified with a $C_{1-5}$ alkyl group.

In the general formula [I], acyl groups represented by $R_2$, are preferably (1) formyl group, (2) $C_{2-6}$ alkanoyl groups (e.g. acetyl, propionyl, isopropionyl, butyryl, isobutyryl, valeryl, isovaleryl, pivaloyl and hexanoyl) optionally having 1 to 3 substituents selected from, for example, halogen atoms (e.g. fluorine, chlorine, bromine and iodine), $C_{2-6}$ alkanoyl groups (e.g. acetyl, propionyl, isopropionyl, butyryl, isobutyryl, valeryl, isovaleryl, pivaloyl and hexanoyl) and nitro group, (3) $C_{7-11}$ aroyl groups (e.g. benzoyl) optionally having 1 to 3 substituents selected from, for example, halogen atoms (e.g. fluorine, chlorine, bromine and iodine), $C_{2-6}$ alkanoyl groups (e.g. acetyl, propionyl, isopropionyl, butyryl, isobutyryl, valeryl, isovaleryl, pivaloyl and hexanoyl) and nitro group, (4) $C_{2-7}$ alkoxycarbonyl groups (e.g. methoxycarbonyl, ethoxycarbonyl, n-propoxycarbonyl, n-butoxycarbonyl, and tert-butoxycarbonyl) optionally having 1 to 3 substituents selected from, for example, halogen atoms (fluorine, chlorine, bromine and iodine), $C_{2-6}$ alkanoyl groups (e.g. acetyl, propionyl, isopropionyl, butyryl, isobutyryl, valeryl, isovaleryl, pivaloyl and hexanoyl) and nitro group, (5) $C_{7-11}$ aryloxycarbonyl groups (e.g. phenyloxycarbonyl) optionally having 1 to 3 substituents selected from, for example, halogen atoms (e.g. fluorine, chlorine, bromine and iodine), $C_{2-6}$ alkanoyl groups (e.g. acetyl, propionyl, isopropionyl, butyryl, valeryl, isovaleryl, pivaloyl and hexanoyl) and nitro group, (6) $C_{8-3}$ aralkylcarbonyl groups (e.g. benzylcarbonyl and phenylethylcarbonyl) optionally having 1 to 3 substituents selected from, for example, halogen atoms (e.g. fluorine, chlorine, bromine and iodine), $C_{2-6}$ alkanoyl groups (e.g. acetyl, propionyl, isopropionyl, butyryl, isobutyryl, valeryl, isovaleryl, pivaloyl and hexanoyl) and nitro group, and (7) $C_{8-13}$ aralkyloxycarbonyl groups (e.g. benzyloxycarbonyl) optionally having 1 to 3 substituents selected from, for example, halogen atoms (e.g. fluorine, chlorine, bromine and iodine), $C_{2-6}$ alkanoyl groups (e.g. acetyl, propionyl, isopropionyl, butyryl, isobutyryl, valeryl, isovaleryl, pivaloyl and hexanoyl) and nitro group.

More preferable examples of the acyl group include (1) formyl, (2) $C_{2-6}$ alkanoyl groups (e.g. acetyl, propionyl, isopropionyl, butyryl, isobutyryl, valeryl, isovaleryl, pivaloyl and hexanoyl) optionally having 1 to 3 substituents selected from, for example, halogen atoms (e.g. fluorine, chlorine, bromine and iodine), $C_{2-6}$ alaknoyl groups (e.g. acetyl, propionyl, isopropionyl, butyryl, isobutyryl, valeryl, isovaleryl, pivaloyl and hexanoyl) and nitro group, (3) $C_{2-7}$ alkoxycarbonyl groups (e.g. methoxydarbonyl, ethoxycarbonyl, n-propoxycarbonyl, n-butoxycarbonyl and tert-butoxycarbonyl) optionally having 1 to 3 substituents selected from, for example, halogen atoms (e.g. fluorine, chlorine, bromine and iodine), $C_{2-6}$ alkanoyl groups (e.g. acetyl, propionyl, isopropionyl, butyryl, isobutyryl, valeryl, isovaleryl, pivaloyl and hexanoyl) and nitro group, and (4) $C_{8-13}$ aralkyloxycarbonyl groups (e.g. benzyloxycarbonyl) optionally having 1 to 3 substituents selected from, for example, halogen atoms (e.g. fluorine, chlorine, bromine and iodine), $C_{2-6}$ alkanoyl groups (e.g. acetyl, propionyl, isopropionyl, butyryl, isobutyryl, valeryl, isovaleryl, pivaloyl and hexanoyl) and nitro group.

Referring to the general formula [I], the hydrocarbon residues in the optionally substituted hydrocarbon residues represented by $R_2$ are preferably $C_{1-20}$ hydrocarbon residues. These hydrocarbon residues are exemplified by (1) $C_{1-15}$ alkyl groups (methyl, ethyl, propyl, isopropyl, butyl, isobutyl, sec-butyl, tert-butyl, pentyl, isopentyl, hexyl, heptyl, octyl, nonyl, decyl, undecyl, dodecyl, tridecyl, tetradecyl and pentadecyl), (2) $C_{3-12}$ cycloalkyl groups (cyclopropyl, cyclobutyl, cyclopentyl, cyclohexyl and adamantyl), (3) $C_{2-10}$ alkenyl groups (e.g. vinyl, allyl, 2-methylallyl, 2-butenyl, 3-butenyl and 3-octenyl), (4) $C_{2-10}$ alkynyl groups (e.g. ethynyl, 2-propinyl and 3-hexynyl), (5) $C_{3-10}$ cycloalkenyl groups (e.g. cyclopropenyl, cyclopentenyl and cyclohexenyl), (6) $C_{6-14}$ aryl groups (e.g. phenyl and naphthyl) and (7) $C_{7-14}$ aralkyl groups (e.g. benzyl, phenethyl, (1-naphthyl)methyl, (2-naphthyl)methyl and 2,2-diphenylethyl).

More preferable examples of hydrocarbon residues are $C_{1-5}$ hydrocarbon residues, as exemplified by $C_{1-15}$ alkyl groups (e.g. methyl, ethyl, propyl, isopropyl, butyl, isobutyl, sec-butyl, tert-butyl, pentyl, isopentyl, hexyl, heptyl, octyl, nonyl, decyl, undecyl, dodecyl, tridecyl, tetradecyl and pentadecyl) and $C_{7-14}$ aralkyl groups (e.g. benzyl, phenethyl, (1-naphthyl)methyl, (2-naphthyl)methyl and 2,2-diphenylethyl).

These hydrocarbon residues may optionally have 1 to 5 substituents, at any possible positions, selected from, for example, (1) amino groups optionally having one or two substituents selected from (a) $C_{1-4}$ alkyl groups (e.g. methyl, ethyl, propyl, isopropyl, butyl, isobutyl, sec-butyl and tert-butyl), (b) $C_{1-6}$ alkanoyl groups (e.g. formyl, acetyl, propionyl, isopropionyl, butyryl, isobutyryl, valeryl, isovaleryl, pivaloyl and hexanoyl), (c) $C_{7-11}$ aroyl groups (e.g. benzoyl, p-toluoyl, 1-naphthoyl and 2-naphthoyl), (d) $C_{2-7}$ alkoxycarbonyl groups (e.g. methoxycarbonyl, ethoxycarbonyl, propoxycarbonyl, butoxycarbonyl and tert-butoxycarbonyl), (e) $C_{8-12}$ aralkyloxycarbonyl groups (e.g. benzyloxycarbonyl and phenylethyloxycarbonyl), (f) $C_{1-6}$ alkylsulfonyl groups (e.g. methylsulfonyl, ethylsulfonyl and propylsulfonyl) and (g) $C_{6-2}$ arylsulfonyl groups (e.g. phenylsulfonyl and tosyl), (2) hydroxyl group optionally having substituent selected from (a) $C_{1-4}$ alkyl groups (e.g. methyl, ethyl, propyl, isopropyl, butyl, isobutyl, sec-butyl and tert-butyl), (b) $C_{7-12}$ aralkyl groups (e.g. benzyl and phenethyl), (c) $C_{1-6}$ alkanoyl groups (e.g. formyl, acetyl, propionyl, isopropionyl, butyryl, isobutyryl, valeryl, isovaleryl, pivaloyl and hexanoyl) and (d) $C_{7-11}$ aroyl groups (e.g. benzoyl, p-toluoyl, 1-naphthoyl and 2-naphthoyl), (3) mercapto group optionally having substituent selected from (a) $C_{1-4}$ alkyl group (e.g. methyl, ethyl, propyl, isopropyl, butyl, isobutyl, sec-butyl and tert-butyl) and (b) $C_{6-10}$ aryl group (e.g. phenyl and naphthyl), (4) carboxyl group, (5) carbamoyl group, (6) $C_{2-5}$ alkoxycarbonyl groups (e.g. methoxycarbonyl and ethoxycarbonyl), (7) $C_{8-14}$ aralkyloxycarbonyl groups (e.g. benzyloxycarbonyl), (8) 5- or 6-membered heterocyclic groups including, besides carbon atoms, 1 to 4 hetero-atoms selected from oxygen, sulfur and nitrogen, or condensed heterocyclic groups thereof (e.g. 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl, indolyl, 2- or 3-tetrahydrofuryl, pyrrolidinyl and piperidino) optionally having 1 to 4 substituents selected from (a) halogen atoms (e.g. fluorine, chlorine, bromine and iodine), (b) $C_{1-4}$ alkyl groups (e.g. methyl, ethyl, propyl and isopropyl), (c) halogenophenoxy groups (e.g. o-, m- or p-chlorophenoxy and o-, m- or p-bromophenoxy) and (d) hydroxyl group, (9) nitro group, (10) cyano group, (11) halogen atom (e.g. fluorine, chlorine, bromine and iodine), (12) guanidyl groups optionally substituted with nitro group, (13) amidino group and (14) $C_{3-8}$ cycloalkyl groups (e.g. cyclopropyl, cyclobutyl, cyclopentyl and cyclohexyl); and, when the hydrocarbon residue is cycloalkyl, cyloalkenyl, aryl or aralkyl group, it may optionally have, as substituents, one to four $C_{1-4}$ alkyl groups optionally substituted by halogen atoms (e.g. fluorine, chlorine, bromine and iodine) (e.g. methyl, ethyl, propyl, isopropyl, butyl and trifluoromethyl).

In the general formula [I], $R_2$ is preferably hydrogen or an optionally substituted hydrocarbon residue, more preferably hydrogen or an optionally substituted alkyl or aralkyl group. $R_2$ is most preferably hydrogen.

In the general formula [I], the divalent hydrocarbon residue in the optionally substituted divalent hydrocarbon represented by X is preferably, among others, a $C_{1-20}$ divalent aliphatic hydrocarbon residue.

Examples of the divalent aliphatic hydrocarbon residue include straight-chain or branched saturated hydrocarbon groups represented by $—C_mH_{2m}—$ ($1 \leq m \leq 15$, m is an integer) (e.g. methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, methylmethylene, ethylethylene and propylene), straight-chain or branched unsaturated hydrocarbon groups (e.g. propenylene and vinylene) represented by $—C_pH_{2(p-q)}—$ ($2 \leq p \leq 15$, p>q, p and q are integral numbers) and aliphatic cyclic hydrocarbon groups (e.g. cyclohexylene and cyclopentylene) represented by $—C_rH_{2(r-1)}—$ ($3 \leq r \leq 15$, r is an integer).

The divalent aliphatic hydrocarbon residue is preferably a straight-chain or branched saturated hydrocarbon group represented by $—C_mH_{2m}—$ ($1 \leq m \leq 15$, m is an integral number).

Referring to the general formula [I], examples of the substituents in the optionally substituted divalent hydrocarbon residue represented by X include (1) amino group optionally having one or two substituents selected from (a) $C_{1-4}$ alkyl groups (e.g. methyl, ethyl, propyl, isopropyl, butyl, isobutyl, sec-butyl and tert-butyl), (b) $C_{1-6}$ alkanoyl groups (e.g. formyl, acetyl, propionyl, isopropionyl, butyryl, isobutyryl, valeryl, isovaleryl, pivaloyl and hexanoyl), (c) $C_{7-11}$ aroyl groups (e.g. benzoyl, p-toluoyl, 1-naphthoyl and 2-naphthoyl), (d) $C_{2-7}$ alkoxycarbonyl groups (e.g. methoxycarbonyl, ethoxycarbonyl, propoxycarbonyl, butoxycarbonyl and tert-butoxycarbonyl), (e) $C_{8-12}$ aralkyloxycarbonyl groups (e.g. benzyloxycarbonyl and phenethyloxycarbonyl), (f) $C_{1-6}$ alkylsulfonyl groups (e.g. methylsulfonyl, ethylsulfonyl and propylsulfonyl) and (g) $C_{6-12}$ arylsulfonyl groups (e.g. phenylsulfonyl and tosyl), (2) hydroxyl group optionally having substituent selected from (a) $C_{1-4}$ alkyl groups (e.g. methyl, ethyl, propyl, isopropyl, butyl, isobutyl, sec-butyl and tert-butyl), (b) 7–12 aralkyl groups (e.g. benzyl and phenethyl), (c) $C_{1-6}$ alkanoyl groups (e.g. formyl, acetyl, propionyl, isopropionyl, butyryl, isobutyryl, valeryl, isovaleryl, pivaloyl and hexanoyl) and (d) $C_{7-11}$ aroyl groups (e.g. benzoyl, p-toluoyl, 1-naphthoyl, and 2-naphthoyl), (3) mercapto group optionally having substituent selected from (a) alkyl groups (e.g. methyl, ethyl, propyl, isopropyl, butyl, isobutyl, sec-butyl and tert-butyl) and (b) $C_{6-10}$ aryl groups (e.g. phenyl and naphthyl), (4) carboxyl group, (5) carbamoyl group, (6) $C_{2-5}$ alkoxycarbonyl groups (e.g. methoxycarbonyl and ethoxycarbonyl), (7) $C_{8-14}$ aralkyloxycarbonyl groups (e.g. benzyloxycarbonyl), (8) 5- or 6-membered heterocyclic groups containing 1 to 4 hetero-atoms, besides carbon atom, selected from oxygen, sulfur and nitrogen, or its condensed heterocyclic groups (e.g. 2- or 3-thienyl, 2- or 3-furyl, 2- or 3-pyrrolyl, 3-, 4-or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl and indolyl) optionally having 1 to 4 substituents selected from (a) halogen atoms (e.g. fluorine, chlorine, bromine and iodine), (b) $C_{1-4}$ alkyl groups (e.g. methyl, ethyl, propyl and isopropyl), (c) halogenophenoxy groups (e.g. o-, m- or p-chlorophenoxy and o-, m- or p-bromopohenoxy) and (d) hydroxyl group, (9) nitro group, (10) cyano group, (11) halogen atoms (e.g. fluorine, chlorine, bromine and iodine), (12) guanidyl group optionally substituted with nitro group, (13) amidino group, (14) $C_{6-14}$ aryl groups (e.g phenyl and naphthyl) optionally having 1 to 3 substituents selected from (a) halogen atoms (e.g. fluorine, chlorine, bromine and iodine), (b) nitro group, (c) hydroxyl group and (d) $C_{1-4}$ alkoxy groups (e.g. methoxy, ethoxy, propoxy, isopropoxy, butoxy, isobutoxy, sec-butoxy and tert-butoxy) and (15) $C_{3-8}$ cycloalkyl groups (e.g. cyclopropyl, cyclobutyl, cyclopentyl and cyclohexyl) optionally having 1 to 3 substituents selected from (a) halogen atoms (e.g. fluorine, chlorine, bromine and iodine), (b) nitro group, (c) hydroxyl group and (d) $C_{1-4}$ alkoxy groups (e.g. methoxy, ethoxy, propoxy, isopropoxy, butoxy, isobutoxy, sec-butoxy and tert-butoxy).

Preferable substituents include (1) 5- or 6-membered heterocyclic group having, besides carbon atoms, 1 to 4 hetero-atoms selected from oxygen, sulfur and nitrogen, or its condensed heterocyclic group (e.g. 2- or 3-thienyl, 2- or 3-furyl, 2- or 3-pyrrolyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3, or 4-pyridazinyl, quinolyl, isoquinolyl and indolyl) optionally having 1 to 4 substituents selected from (a) halogen atoms (e,g, fluorine, chlorine, bromine and iodine), (b) $C_{1-4}$ alkyl groups (e.g. methyl, ethyl, propyl and isopropyl), (c) halogenophenoxy groups (e.g. o-, m- or p-chlorophenoxy, and o-, m- or p-bromophenoxy) and (d) hydroxyl group, (2) $C_{6-14}$ aryl groups (e.g. phenyl and naphthyl) optionally having 1 to 3 substituents selected from (a) halogen atoms (e.g. fluorine, chlorine, bromine and iodine), (b) nitro group, (c) hydroxyl group and (d) $C_{1-4}$ alkoxy groups (e.g. methoxy, ethoxy, propoxy, isopropoxy, butoxy, isobutoxy, sec-butoxy and tert-butoxy), and (3) $C_{3-8}$ cycloalkyl groups (e.g. cyclopropyl, cyclobutyl, cyclopentyl and cyclohexyl) optionally having 1 to 3 substituents selected from (a) halogen atoms (e.g. fluorine, chlorine, bromine and iodine), (b) nitro group, (c) hydroxyl group and (d) $C_{1-4}$ alkoxy groups (e.g. methoxy, ethoxy, propoxy, isopropoxy, butoxy, isobutoxy, sec-butoxy and tert-butoxy).

More preferable substituents are $C_{6-14}$ aryl groups (e.g. phenyl and naphthyl) optionally having 1 to 3 substituents selected from (a) halogen atoms (e.g. fluorine, chlorine, bromine and iodine), (b) nitro group, (c) hydroxyl group and (d) $C_{1-4}$ alkoxy groups (e.g. methoxy, ethoxy, propoxy, isopropoxy, butoxy, isobutoxy, sec-butoxy and tert-butoxy).

Number of substituents ranges preferably from 1 to 5, more preferably 1 to 3.

In the general formula [I] wherein Q represents the partial structural formula: —CO—N($R_3$)($R_4$), the partial structural formula —NH—X—CO— are preferably amino acid residue. As the amino acid, mention is made of, for example, amino acid which constitutes protein or amino acid obtainable from natural sources as metabolite of microorganisms or components of animals and vegetables.

Examples of amino acids which constitute protein include aliphatic monoaminocarboxylic acid (e.g. glycine, alanine, valine, leucine and isoleucine), aliphatic hydroxyamino acid (e.g. serine and threonine), acidic amino acid (e.g. aspartic acid and glutamic acid), acidic amino acid amide (.e.g. asparagine and glutamine), aromatic amino acid (e.g. phenylalanine, tyrosine and tryptophan), basic amino acid (e.g. arginine, lysine and histidine) and sulfur-containing amino acid (e.g. methionine, cystine and cysteine).

Examples of amino acids obtainable from natural sources as metabolites of microorganisms or components of animals and vegetables include aliphatic monoaminocarboxylic acids (e.g. L-α-aminobutyric acid, γ-aminobutyric acid, β-aminoisobutyric acid, β-alanine, homoserine, α-methyl-D-serine, O-carbamyl-D-serine, and δ-hydroxy-γ-oxo-norvaline), monoaminodicarboxylic acid (e.g. L-α-aminoadipic acid, L-theanine,L-γ-methyleneglutamic acid and L-γ-methylglutamic acid), diaminomonocarboxylic acid (e.g. L-ornithine, β-lysine, α,β-diaminopropionic acid and L-α,γ-diaminobutyric acid), diaminiodicarboxylic acid (e.g. diaminopimeric acid), amino acid containing sulfonic acid (e.g. cysteic acid), aromatic amino acid (e.g. kynurenine and 3,4-dioxyphenyl-L-alanine), heterocyclic amino acid (e.g. aziridine-2,3-dicarboxylic acid, [S]-2-amino-3-(isoxazolin-5-on-4-yl)propionic acid and anticapsin), basic amino acid (e.g. L-4-oxalysine, L-4-oxolysine and [3R,5R]-3,6-diamino-5-hydroxyhexanoic acid), sulfur-containing amino acid (e.g. lanthionine and S-methyl-L-cysteine), cyclic amino acid (e.g. pipecolic acid, azetidine-2-carboxylic acid and [1R,2S]-2-aminocyclopentane-1-carboxylic acid) and amino acid substituted with specific functional group (e.g. citrulline, alanosine and L-azaserine).

The amino acid residue represented by the partial structural formula, —NH—X—CO—, is preferably α-amino acid residue. Preferable examples of the α-amino acid residue include residues of aliphatic monoaminocarboxylic acid (e.g. glycine, alanine, valine, leucine and isoleucine), acidic amino acid (e.g. aspartic acid and glutamic acid), aromatic amino acid (e.g. phenylalanine, tyrosine and tryptophan) and basic amino acid (e.g. arginine, lysine and histidine). More preferable examples of the α-amino acid residue are residues of aromatic amino acid (e.g. phenylalanine, tyrosine and tryptophan). The α-amino acid is preferably of L-configuration.

In the present invention, compounds of the general formula [I], wherein $R_1$ is an optionally esterified carboxyl group; $R_2$ is hydrogen or an optionally substituted hydrocarbon residue; and Q represents the partial structural formula: —CO—N($R_3$)($R_4$), are preferable. Furthermore, the compounds, wherein amino acid residue represented by the partial structural formula —NH—X—CO— is α-amino acid residue; and either $R_3$ or $R_4$ is hydrogen, and the other is an optionally substituted hydrocarbon residue, are especially preferable.

The preferred examples of compound [I] or salts thereof include

N-[N-[(2S,3S)-3-ethoxycarbonylaziridine-2-carbonyl]-L-phenylalanyl]-2-phenylethylamine, N-[N-[(2S,3S)-3-ethoxycarbonylaziridine-2-carbonyl]-L-phenylalanyl]isopentylamine, N-[N-[(2S,3S)-3-ethoxycarbonylaziridine-2-carbonyl]-L-phenylalanyl]-3-methoxypropylamine, N-[N-[(2S,3S)-3-ethoxycarbonylaziridine-2-carbonyl]-L-phenylalanyl]-N-methyl-2-phenylethylamine or salts thereof.

A method of producing the above-described compound [I] or a salt thereof is hereinafter described.

Protecting groups and reagents often mentioned herein are abbreviated as follows:

FmOC: 9-fluorenylmethyloxycarbonyl
Z: benzyloxycarbonyl
Boc: t-butoxycarbonyl
Bzl: benzyl
TFA: trifluoroacetic acid
Tos: p-toluenesulfonic acid
DCC: N,N'-dicyclohexylcarbodiimide
BOP: benzotriazol-1-yloxytris (dimethylamino) phosphonium hexafluorophosphate
DIC: N,N'-diisopropylcarbodiimide
HONB: N-hydroxy-5-norbornene-2,3-dicarboxyimide
HOBT: 1-hydroxybenzotriazole WSC: water-soluble carbodiimide[1-ethyl-3-(3-dimethylaminopropyl)carbodiimide hydrochloride]
R-: R-configuration
S-: S-configuration A compound represented by general formula [I] or a salt thereof can be produced by subjecting a compound represented by general formula:

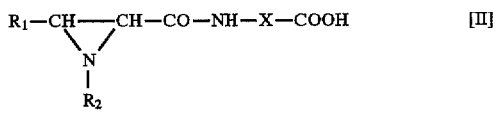

wherein symbols have the same meanings as defined above, or a salt thereof, to esterification or amidation; or by reacting a compound represented by the general formula:

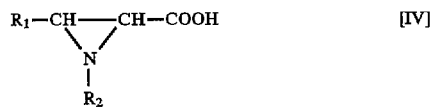

wherein symbols have the same meaning as defined above, or a salt thereof with a compound represented by the general formula:

wherein symbols have the same meaning as defined above, or a salt thereof, followed by, when necessary, a deprotection reaction.

The esterification can be carried out by per se known methods, as exemplified below.

1) A starting compound is allowed to react with diazoalkane (e.g. diazomethane, phenyldiazomethane and diphenyldiazomethane).

2) A starting compound is allowed to react with an activated alkyl halide (e.g. methyl iodide, benzyl bromide and pivaloyloxymethyl chloride).

3) A starting compound is allowed to react with alcohol (e.g. methanol, ethanol and benzyl alcohol) in the presence of an acid catalyst or a condensing agent. As the acid catalyst, use is made of, for example, hydrochloric acid, sulfuric acid or camphorsulfonic acid, and as the condensing agent, use is made of DCC, WSC or DIC.

4) A starting material is led to its active ester, which is allowed to react with alcohol (e.g. methanol, ethanol, benzyl alcohol). As the active ester, use is made of, for example, esters with 1-hydroxy-1H-2-pyridone, N-hydroxysuccinimide, N-hydroxyphthalimide and 1-hydroxybenzotriazole.

5) A starting compound is allowed to react with an acid halogenide (e.g. ethyl chloroformate and benzyl chloroformate) to give an acid anhydride, which is then allowed to react with alcohol (e.g. methanol, ethanol and benzyl alcohol).

This reaction is usually carried out in a solvent which does not interfere with the reaction. Examples of the solvent include amides such as formamide, N,N-dimethylformamide and N-methylpyrrolidone, sulfoxides such as dimethyl sulfoxide, aromatic amines such as pyridine, halogenated hydrocarbons such as chloroform and dichloromethane, ethers such as tetrahydrofuran and dioxane, nitriles such as acetonitrile, esters such as ethyl acetate and ethyl formate, alcohols such as methanol and ethanol, or mixtures of them in appropriate ratios.

This reaction may be conducted in the presence of a base. As the base, use is made of, for example, tertiary amines such as trimethylamine, triethylamine, tripropylamine, N-methylpiperidine, N-methylpyrrolidine, cyclohexyldimethylamine and N-methylmorpholine, secondary amines such as di-n-butylamine, diisobutylamine and dicyclohexylamine, aromatic amine such as pyridine, lutidine and collidine, hydroxides or salts of alkali metals such as lithium, sodium and potassium, and hydroxides or salts of alkaline earth metals such as calcium and magnesium.

The reaction temperatures ranges usually from –50° C. to 150° C., preferably –30° C. to 80° C., although they are not specifically limited so long as the reaction proceeds. The reaction time varies with starting compounds, bases, reaction temperatures and kinds of solvents then employed, and it ranges normally from several ten minutes to several ten hours.

In the above-mentioned amidation and reaction of compound [IV] with compound [V], a conventional means of peptide synthesis, such as liquid phase synthesis or solid phase synthesis. Any known methods for peptide synthesis can be employed, as exemplified by those described in "Peptide Synthesis" authored by M. Bondasky and M. Ondetti, Interscience, New York, (1966); in "The Proteins Vol.2" authored by F. M. Finn and K. Hofmann, edited by H. Nenrath and R. L. Hill, Academic Press Inc., New York, (1976),; in "Peptide Gosei No Kiso To Jikken" Maruzen Co., Ltd., (1985), authored by Nobuo Izumiya et al.; in "Seikagaku Jikken Koza 1" authorized by Haruaki Yajima, Shunpei Sakakibara et al., edited by the Japanese Biochemical Society, Tokyo Kagaku Dojin (1977); in "Zoku Seikagaku Jikken Koza 2", authorized by Toshiya Kimura et al., edited by the Japanese Biochemical Society, Tokyo Kagaku Dojin (1987); and in "Solid Peptide Synthesis", Pierce Chemical Company, Illinois (1984), authorized by J. M. Stewart and J. D. Young; or analogous methods thereto. Specific examples of those methods include the azide method, the chloride method, the acid anhydride method, the mixed acid anhydride method, the DCC method, the active ester method, the method using Woodward reagent K, the carbonylimidazole method, the oxidation reduction method, the DCC/HONB method, the DIC/HONB method, the DCC/HOBT method, the WSC/HOBT method and the method using BOP reagent, in which the carboxylic acid in compound [II] or a salt thereof and compound [IV] or a salt thereof is activated, which is then condensed with a compound represented by the general formula

wherein symbols have the same meaning as defined above, or a salt thereof, and compound [V] or a salt thereof, respectively.

With respect, among others, to the protection of functional groups not to be involved in the reaction of starting materials, the protecting groups to be employed, elimination of the protecting groups, and activation of functional groups involved in the reaction, per se known ones or per se known means can be appropriately employed.

This reaction may be conducted in the presence of a base. Examples of the base include tertiary amines such as trimethylamine, triethylamine, tripropylamine, N-methylpiperidine, N-methylpyrrolidine, cyclohexyldimethylamine and N-methylmorpholine, secondary amines such as di-n-butylamine, diisobutylamine and dicyclohexylamine, aromatic amines such as pyridine, lutidine and collidine, alkali metal hydroxides such as lithium hydroxide, sodium hydroxide and potassium hydroxide, alkali metal hydrogencarbonates such as sodium hydrogencarbonate and potassium hydrogencarbonate, alkali metal carbonates such as sodium carbonate and potassium carbonate, alkaline earth metal hydroxides such as calcium hydroxide and magnesium hydroxide, and alkaline earth metal carbonates such as calcium carbonate and magnesium carbonate.

In the above-mentioned reaction of compound [II] with compound [III], usually about 1 mol. of a reactive derivative of carboxylic acid of compound [II] is used relative to 1 mol. of compound [III]. And, in the reaction of compound [IV] with compound [V], usually about 1 mol. of a reactive derivative of carboxylic acid of compound [IV] is used relative to 1 mol. of compound [V]. These reactive derivatives of carboxylic acid can be used in an excess amount, so long as they do not give undesirable effects on the reaction. When a base is used, its amount ranges usually from about 1 to 5 mol., preferably from about 1 to 3 mol., relative to 1 mol. of compound [III] or [V], while it varies depending on starting compounds, kinds of reactive derivatives of carboxylic acid and other reaction conditions.

This reaction is usually carried out in a solvent which does not interfere with the reaction. The solvent can be selected appropriately from known solvents as useful in peptide condensation reaction. Such solvents are exemplified by amides such as formamide, N,N-dimethylformamide and N-methylpyrrolidone, sulfoxides such as dimethyl sulfoxide, aromatic amines such as pyridine, halogenated hydrocarbons such as chloroform and dichloromethane, ethers such as tetrahydrofuran and dioxane, nitriles such as acetonitrile, and esters such as ethyl acetate and ethyl formate. These solvents can be used as an appropriate mixture.

The reaction temperatures range usually from about −50° C. to +150° C., preferably from −30° C. to +80° C., although they are not specifically limited, so long as the reaction proceeds. The reaction time ranges usually from several ten minutes to several ten hours, depending on starting compounds, bases, reaction temperatures and kinds of solvents employed.

A compound [I], wherein $R_1$ is an esterified carboxyl group, or a salt thereof can be produced by, for example, subjecting a compound [I], wherein $R_1$ is carboxyl group, or a salt thereof to esterification described above.

A compound [I], wherein $R_1$ is an amidated carboxyl group, or a salt thereof can also be produced by, for example, subjecting a compound [I], wherein $R_1$ is carboxyl group, or a salt thereof to condensation with a compound represented by the formula:

$$R_6\text{—NH}_2 \qquad [VI]$$

wherein $R_6$ has the same meaning as defined above, or a salt thereof by a conventional method for petitde synthesis as described above.

A compound [I], wherein $R_2$ is an optionally substituted hydrocarbon residue, or a salt thereof can also be produced by subjecting a compound [I], wherein $R_2$ is hydrogen, or a salt thereof to substitution reaction using a compound represented by the general formula:

$$R_2'\text{—Y} \qquad [VII]$$

wherein $R_2'$ is an optionally substituted hydrocarbon residue and Y is a leaving group, or a salt thereof.

The above-mentioned optionally substituted hydrocarbon residue represented by $R_2'$ has the same meaning as that in $R_2$ described above.

The leaving group represented by Y mentioned above is a functional group which is readily substituted by a chemical reaction. More specifically, use is made of, for example, halogen atoms (e.g. fluorine, chlorine, bromine and iodine), methanesulfonyloxy group, p-toluenesulfonyloxy group, benzenesulfonyloxy group, trifluoromethanesulfonyloxy group, methoxysulfonyloxy group and ethoxysulfonyloxy group.

This reaction is carried out in a solvent which does not interefere with the reaction. Examples of the solvent include amides such as formamide, N,N-dimethylformamide and N-methylpyrrolidone, sulfoxides such as dimethyl sulfoxide, aromatic amines such as pyridine, halogenated hydrocarbons such as chloroform and dichloromethane, ethers such as tetrahydrofuran and dioxane, nitriles such as acetonitrile, esters such as ethyl acetate and ethyl formate, alcohols such as methanol and ethanol, or mixtures of them in appropriate ratios.

This reaction may be conducted in the presence of a base. As the base, use is made of, for example, tertiary amines such as trimethylamine, triethylamine, tripropylamine, N-methylpiperidine, N-methylpyrrolidine, cyclohexyldimethylamine and N-methylmorpholine, secondary amines such as di-n-butylamine, diisobutylamine and dicyclohexylamine, aromatic amine such as pyridine, lutidine and collidine, hydroxides or salts of alkali metals such as lithium, sodium and potassium, and hydroxides or salts of alkaline earth metals such as calcium and magnesium.

The reaction temperatures ranges usually from −50° C. to 150° C., preferably −30° C. to 80° C., although they are not specifically limited, so long as the reaction proceeds. The reaction time varies with starting compounds, bases, reaction temperatures and kinds of solvents then employed, and it ranges normally from several ten minutes to several ten hours.

A compound [I], wherein $R_2$ is an optionally substituted hydrocarbon residue, or a salt thereof can also be produced by, for example, subjecting a compound, wherein $R_2$ is hydrogen, or a salt thereof to reductive condensation with a carbonyl compound.

As the carbonyl compound, use is made of, for example, aldehydes such as formaldehyde, acetaldehyde, propionaldehyde and benzaldehyde, and ketones such as acetone, ethyl methyl ketone and diethyl ketone. As the method of reduction, mention is made of, for example, 1) reduction using complex hydrogen compounds such as lithium aluminum hydride, sodium cyanoborohydride and sodium borohydride, diborane, sodium, sodium amalgam and zinc-acid, 2) catalytic reduction using palladium catalyst (e.g. palladium/barium sulfate, palladium/activated charcoal, palladium black) or rhodium catalyst, and 3) electrolytic reduction using lead or platinum as cathode.

This reaction is carried out in a solvent which does not interfere with the reaction. Examples of the solvent include amides such as formamide, N,N-dimethylformamide and N-methylpyrrolidone, sulfoxides such as dimethyl sulfoxide, aromatic amines such as pyridine, halogenated hydrocarbons such as chloroform and dichloromethane, ethers such as tetrahydrofuran and dioxane, nitriles such as acetonitrile, esters such as ethyl acetate and ethyl formate, alcohols such as methanol and ethanol, or mixtures of them in appropriate ratios.

The reaction temperatures ranges usually from −50° C. to 150° C., preferably −30° C. to 80° C., although they are not specifically limited, so long as the reaction proceeds. The reaction time varies with starting compounds, bases, reaction temperatures and kinds of solvents then employed, and it ranges normally from several ten minutes to several ten hours.

A compound of the general formula [I] or a salt thereof can be produced by, when necessary, subjecting a compound or a salt thereof produced by the above-described method to a deprotection reaction. This deprotection reaction can be carried out by a per se known method, such as a method in common use in peptide chemistry (cf. Gosei Kagaku Series, Peptide Gosei, by Nobuo Izumiya, Motonori Ohno, Tetsuo Kato and Haruhiko Aoyagi, published by Maruzen Co., Ltd.,1975).

For instance, the deprotection reaction for the amino group protected by an urethane type protecting group is carried out in contact with an acid in the absence of a solvent or in a solvent which does not interfere with the reaction. As the solvent, use is made of, for example, halogenated hydrocarbons (e.g. dichloromethane, chloroform and 1,2-dichloroethane), alcohols (e.g. methanol and ethanol), esters (e.g. ethyl acetate), water and appropriate mixtures thereof. The acid is exemplified by haloacetic acids (e.g. trifluoroacetic acid) and hydrohalogenic acids (e.g. hydrochloric acid and hydrobromic acid).

It is advantageous that the N-benzyloxycarbonyl(Z) group and N-4-methoxybenzyloxycarbonyl group are eliminated by catalytic hydrogenation using, e.g. a palladium catalyst (e.g. palladium/barium sulfate, palladium/activated charcoal and palladium black) and a rhodium catalyst. This reaction is carried out in a solvent which does not interfere with the reaction. As the solvent, use is made of, for example, amides (e.g. N,N-dimethylformamide and acetamide), alcohols (e.g. methanol and ethanol), cyclic ethers (e.g. tetrahydrofuran), organic carboxylic acid (e.g. acetic acid and propionic acid), water or an appropriate mixture of them.

It is advantageous that the N-9-fluorenylmethyloxycarbonyl (Fmoc) group is eliminated using an organic amine such as diethylamine, piperidine, morpholine, 4-dimethylaminopyridine or dicyclohexylamine. This reaction is carried out in a solvent which does not interfere with the reaction. As the solvent, use is made of, for example, amides (e.g. N,N-dimethylformamide and acetamide), alcohols (e.g. methanol and ethanol) and an appropriate mixture of them.

It is advantageous that the N-2,2,2-trichloroethyloxycarbonyl group is eliminated using a metal (e.g. zinc) along with an organic carboxylic acid (e.g. acetic acid and propionic acid). This reaction is carried out in a solvent which does not interfere with the reaction. As the solvent, use is made of, for example, the above-mentioned organic carboxylic acid, alcohols (e.g. methanol and ethanol), water and an appropriate mixture of them.

The deprotection reaction (deacylation) of the acylated hydroxyl group is carried out in contact with an acid in a solvent which does not interfere with the reaction. As the solvent, use is made of, for example, halogenated hydrocarbons (e.g. dichloromethane, chloroform and 1,2-dichloroethane), alcohols (e.g. methanol and ethanol), water and an appropriate mixture of them. As the acid, use is made of, for example, haloacetic acids (e.g. trifluoroacetic acid) and hydrohalogenic acid (e.g. hydrochloric acid and hydrobromic acid).

It is advantageous that the O-benzyl (Bzl) group is eliminated by catalytic hydrogenation using, e.g., a palladium catalyst (e.g. palladium/barium sulfate, palladium/activated charcoal and palladium black) or a rhodium catalyst. In this case, a solvent known from literature, for example, a cyclic ether (e.g. tetrahydrofuran) is employed singly or, depending on cases, in a mixture with another inner solvent [e.g. lower aliphatic acid amide (e.g. N,N-dimethylformamide)].

For the O-tetrahydropyranyl group or O-tert-butyl group, deprotection can be conducted by acid hydrolysis as in the above-described deacylation.

The carboxyl protecting group can be removed by acid hydrolysis in substantially the same manner as above. And, for example, the benzyl ester can be removed by catalytic hydrogenation in substantially the same manner as in the case of elimination of the O-benzyl group. Further, the methyl ester or ethyl ester can be removed by bringing them into contact with a base in a solvent which does not interfere with the reaction. The solvent is exemplified by alcohols (e.g. methanol and ethanol), cyclic ethers (e.g. tetrahydrofuran), water and an appropriate mixture of them. As the base, use is made of, for example, sodium hydroxide, potassium hydroxide, sodium carbonate and potassium carbonate.

The 2-(trimethylsilyl)ethyl group can be eliminated by allowing, under neutral conditions, a salt of hydrofluoric acid, especially, for example, a salt of a quaternary nitrogen base with hydrofluoric acid (e.g. tetraethylammonium fluoride) to act in an appropriate solvent.

The compound [I] or a salt thereof thus produced is recovered, after completion of the reaction, by a means of isolating peptide, for example, extraction, distribution, reprecipitation, crystallization, various kinds of chromatography and high performance liquid chromatography.

The compound [II] or a salt thereof, which is used as a starting compound for producing the compound [I], can be produced by subjecting a compound [IV] or a salt thereof to condensation with a compound represented by the general formula:

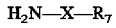

$$H_2N—X—R_7 \qquad [VIII]$$

wherein X has the same meaning as defined above and $R_7$ is a protected carboxyl group, or a salt thereof by a conventional means of peptide synthesis and, then, to deprotection reaction to eliminate the carboxyl protecting group.

The carboxyl-protecting group in the protected carboxyl group represented by $R_7$ above is exemplified by (1) $C_{1-6}$ alkyl groups (e.g. methyl, ethyl, propyl, isopropyl, n-butyl, isobutyl, sec-butyl, tert-butyl, n-pentyl, isopentyl, sec-pentyl, neo-pentyl, tert-pentyl and hexyl) optionally having 1 to 3 substituents selected from (a) nitro group, (b) halogen atoms (e.g. fluorine, chlorine, bromine and iodine) and (c) $C_{1-6}$ alkanoyloxy groups (e.g. formyloxy, acetyloxy, propionyloxy, isopropionyloxy, butyryloxy, isobutyryloxy, valeryloxy, isovaleryloxy, pivaloyloxy and hexanoyloxy), (2) $C_{6-14}$ aryl groups (e.g. phenyl and naphthyl) optionally having 1 to 3 substituents selected from (a) nitro group, (b) halogen atoms (e.g. fluorine, chlorine, bromine and iodine) and (c) $C_{1-4}$ alkoxy groups (e.g. methoxy, ethoxy, propoxy, isopropoxy, butoxy, isobutoxy, sec-butoxy and tert-butoxy), (3) $C_{7-12}$ aralkyl groups (e.g. benzyl and phenethyl) optionally having 1 to 3 substituents selected from (a) nitro group, (b) halogen atoms (e.g. fluorine, chlorine, bromine and iodine)and (c) $C_{1-4}$ alkoxy groups (e.g. methoxy, ethoxy, propoxy, isopropoxy, butoxy, isobutoxy, sec-butoxy and tert-butoxy), (4) trityl group optionally having 1 to 3 substituents selected from (a) halogen atoms (e.g. fluorine, chlorine, bromine and iodine), (b) $C_{1-6}$ alkanoyl (e.g. formyl, acetyl, propionyl and butyryl) and (c) nitro group, and (5) tri-$C_{1-4}$ alkylsilyl groups (e.g. trimethylsilyl and triethylsilyl).

The above-mentioned compound [V] or a salt thereof can be produced by subjecting a compound represented by the general formula:

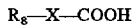

$$R_8—X—COOH \qquad [IX]$$

wherein X has the same meaning as defined above, and $R_8$ is a protected amino group, or a salt thereof to esterification or amidation. The esterification is carried out in the same manner as described above. The amidation is carried out by subjecting the compound [IX] or a salt thereof to condensation with the compound [III] or a salt thereof by such a conventional means for peptide synthesis as described above, and then to deprotection reaction to eliminate the amino-protecting group.

The amino-protecting group in the protected amino group represented by $R_8$ above has the same meaning as the acyl group represented by $R_2$ above.

A compound [IV], wherein $R_1$ is an esterified carboxyl group and $R_2$ is an amino-protecting group, or a salt thereof can be produced by protecting the amino group of aziridine-2,3-dicarboxylic acid, followed by substantially the same esterification as above to give a diester compound represented by the general formula:

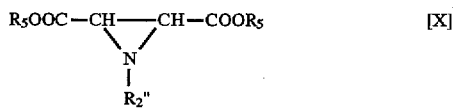 [X]

wherein $R_5$ the same meaning as defined above, and $R_2''$ is an amino-protecting group, then by subjecting the resulting compound to hydrolysis.

The amino-protecting group represented by the above-mentioned $R_2''$ has the same meaning as the acyl group in $R_2$ described above.

The hydrolysis is carried out in contact with a base, in the presence of water, in a solvent which does not interfere with the reaction.

As the solvent which does not interfere with the reaction, use is made of, for example, alcohols (e.g. methanol and ethanol), cyclic ethers (e.g. tetrahydrofuran), amides (e.g. N,N-dimethylformamide and acetamide) and an appropriate mixture of them.

As the base, use is made of, for example, alkali metal hydroxide (e.g. sodium hydroxide and potassium hydroxide) or alkali metal carbonates (e.g. sodium carbonate and potassium carbonate). The base is employed usually about 1 mol. relative to 1 mol. of the compound [X]. The reaction temperatures are not specifically limited so long as the reaction proceeds, and usually range from $-50°$ C. to $150°$ C., preferably from $-10°$ C. to $80°$ C. The reaction time usually ranges from several ten minutes to several ten hours, although it varies with the starting compounds, bases, reaction temperatures and kinds of solvents then employed.

A compound [IV], wherein $R_1$ is an esterified carboxyl group and $R_2$ is an optionally substituted hydrocarbon residue, or a salt thereof can be produced by deprotecting the amino-protecting group in the compound [X] or a salt thereof, subjecting the resultant compound to substantially the same substitution reaction or reductive condensation as described above and, then, subjecting the compound thus obtained to substantially the same hydrolysis as described above.

A compound [IV], wherein $R_1$ is an amidated carboxyl group, or a salt thereof can be produced by subjecting a compound [IV], wherein $R_1$ is an esterified carboxyl group, or a salt thereof to condensation with a compound [VI] or a salt thereof by a substantially the same conventional means for peptide synthesis as described above, and subjecting the compound thus obtained to substantially the same hydrolytic reaction as described above.

Aziridine-2,3-dicarboxylic acid employed as the starting compound for producing the compound [IV] can be produced by the production method using *Streptomyces omiyaensis* MD398-Al [JPA S52(1977)-38091] or by the synthetic method described in Tetrahedron Vol.47, p.5287 (1991). And, aziridine-2,3-dicarboxylic acid can also be produced by using a microorganism capable of producing the compound. As microorganisms employable for this purpose, mention is made of, for example, a strain of Streptomyces, 116-20 strain, which was newly isolated from soil in Ohita Prefecture.

Microbiological properties of the 116-20 strain investigated in accordance with the method described in International Journal of Systematic Bacteriology, Vol.16, p.313–p.340 (1966) are as follows.

Findings on culture media are based on observations conducted in accordance with a conventional method by incubating for 14 days at $28°$ C., unless otherwise specifically stated. Description of color tones is based on "Color Harmony Manual" 4th ed. published by Container Corporation of America, 1958.

(I) Morphological properties

Aerial mycelia grow, showing monopodial branching, from substrate mycelia well growing branchedly. The spore chain (usually consisting of 10 to 50 or more spores) on the top of them show open-spiral. No verticil is observed. Shape of spores is cylindrical or like bamboo tubes (0.8–0.9× 0.9–1.4 µm). The surface of each spore is smooth.

(II) Properties on culture media for classification (a) Sucrose nitrate agar medium
  Growth: poor pale ivory (2ca)
  Aerial mycelia: poor, white
  Color of reverse of colonies: pale ivory (2ca)
  Soluble pigment: none (b) Glucose.asparagine agar medium
  Growth: good, yellowish gray (2ge)
  Aerial mycelia: good, pale reddish gray (4ec)
  Color of reverse of colonies: pale yellowish gray (2gc) –brownish gray (2ni)
  Soluble pigment: none (c) Glycerol asparagine agar medium
  Growth: good, pale yellowish gray (2gc)
  Aerial mycelia: good, gray (3fe)
  Color of reverse of colonies: pale yellowish brown (2ga) –yellowish gray (21e)
  Soluble pigment: none (d) Inorganic salts starch agar medium
  Growth: good, yellowish gray (2ie)
  Aerial mycelia: good, gray (3fe)
  Color of reverse of colonies: pale yellowish brown (2ga) –dark brown (2ng)
  Soluble pigment: none (e) Tyrosine agar medium
  Growth: good, pale yellowish gray (2gc)
  Aerial mycelia: good, gray (3fe)
  Color of reverse of colonies: pale brown (2ic)–dark brown (2ng)
  Soluble pigment: none (f) Nutrient agar medium
  Growth: moderate, pale yellowish brown (2ga)
  aerial mycelia: none
  Color of reverse of colonies: ivory (2ea)
  Soluble pigment: none (g) Yeast extract.malt extract agar medium
  growth: good, grayish brown (31g)
  Aerial mycelia: good, grayish white (3cb)–pale reddish gray (4gc)
  Color of reverse of colonies: pale yellowish gray (2gc)–reddish gray (2ne–4ni)
  Soluble pigment: none (h) Oatmeal agar medium
    Growth: good, brownish gray (2ni)
    Aerial mycelia: good, gray (3fe)
    Color of reverse of colonies: pale yellowish gray (2gc)
    –dark brown (2pi)
    Soluble pigment: none
(i) Peptone.yeast extract.iron agar medium
    Growth: moderate, pale brown (2ic)
    Aerial mycelia: none
    Color of reverse of colonies: pale brown (2ic)
    Soluble pigment: none
(III) Physiological properties
    (a) Growth temperature range 12°–37° C.
        Optimum growth temperature range: 21°–37° C.
    (b) Nitrate reduction: negative
    (c) Liquefaction of gelatin: positive
    (d) Hydrolysis of starch: positive
    (e) Coagulation of skimmed milk: negative
        Peptonization of skimmed milk: positive
    (f) Production of melanoid pigment
        Tyrosine agar medium negative
        Peptone.yeast.iron agar medium: negative
    (g) Assimilation of carbon sources
        L-arabinose: +
        D-xylose: +
        D-glucose: ++
        D-fructose: ++
        Sucrose: ±
        Inositol: −
        L-rhamnose: ±
        Raffinose: −
        D-mannitol: −
        None: −
        Basal medium: Pridham & Gottlieb agar medium (IV) Analytical determination of diaminopimelic acid in the hydrolyzate in the whole culture cells Analysis in accordance of the method of Hasegawa et al disclosed in "Journal of General Applied Microbiology 29, 319–322 (1983)" revealed that the diaminopimelic acid in HCl-hydrolyzate of the culture cells was LL-compound.

To summarize the above-described microbiological properties, 116-20 strain has mycelia whose tips are spiral, and the surface of its spores is smooth. The color in growth is pale yellowish gray or yellowish brown to brown, and aerial mycelia show grayish tone. Incidentally, the strain does not produce melanoid pigment. And, since LL-diaminopimelic acid is detected from cell bodies, the strain classified as belonging to cell wall type I. Based on the above-described properties, identification of the strain was conducted in accordance with "Bergey's Manual of Systematic Bacteriology (1989) Vol.4" to reveal that the strain belongs to the genus Streptomyces, and can be named as Streptomyces sp. 116-20.

This strain has been deposited under accession number IFO 15746 at the Institute for Fermentation, Osaka (IFO) since Sep. 12, 1994, and under accession number FERM BP 4879 at the National Institute of Bioscience and Human Technology (NIBH), Agency of Industrial Science and Technology, Ministry of International Trade and Industry, since Nov. 24, 1994.

Aziridine-2,3-dicarboxylic acid can be produced by cultivating this strain, and in some instances, any microorganisms including any variants thereof, derived by per se known methods including genetic engineering technique, capable of producing the compound, in a culture medium, allowing the compound to be accumulated in a culture medium, and by harvesting the compound.

While a culture medium for cultivation of strains capable of producing aziridine-2,3-dicarboxylic acid may be liquid or solid one so long as it contains nutrients which the strain can utilize, it is more advantageous to employ a liquid medium for processing a relatively large volume. The culture medium is appropriately incorporated with carbon sources, nitrogen sources, inorganic substances and a trace amount of nutrient sources, assimilable by the strain capable of producing aziridine-2,3-dicarboxylic acid. Examples of carbon sources include glucose, lactose, sucrose, maltose, dextrin, starch, glycerine, mannitol, sorbitol, oils and fats (e.g. soybean oil, lard and chicken oil) and n-paraffin and, examples of nitrogen sources include meat extract, yeast extract, dry yeast, soybean flour, corn steep liquor, peptone, cotton seed powder, blackstrap molasses, urea, ammonium salts (ammonium sulfate, ammonium chloride, ammonium nitrate and ammonium acetate).

Further, salts containing, for example, sodium, potassium, calcium or magnesium, metal salts of, for example, iron, manganese, zinc, cobalt or nickel, salts of, for example, phosphoric acid or boric acid, and organic acid salts such as acetic acid and propionic acid salt may be conveniently employed. Besides, amino acids (e.g. glutamic acid, aspartic acid, alanine, lysine, methionine and proline), peptides (e.g. dipeptide and tripeptide), vitamins (e.g. B1, B2, nicotinic acid, B12, and C), nucleic acids (e.g. purine, pyrimidine, derivatives of them) may optionally be incorporated in the culture medium. Needless to state, for the purpose of adjusting the pH of the culture medium, an inorganic or organic acid or alkalis or a buffering agent may be added, or for the purpose of preventing foaming, an appropriate amount of a surfactant may be supplemented. In the case of liquid cultivation, it is preferable to conduct the cultivation for a period ranging from about 48 to 240 hours.

For harvesting the desired compound, aziridine-2,3-dicarboxylic acid, use is made of adequately a means in common use to recover microbial metabolites from a culture of the microorganism. For example, since aziridine-2,3-dicarboxylic acid, a water-soluble acidic substance, is contained principally in the culture filtrate, use is made of advantageously a means which comprises adding a filter aid to the culture broth, removing the cell bodies by filtration or centrifuge, and then by subjecting the culture filtrate or the supernatant of the culture broth to a well known chromatography. Chromatographic carriers which can be used favorably include compounds with which adsorbability difference is applied, such as activated charcoal, silica gel, fine crystalline cellulose and adsorptive resins, those with which functional group difference is applied, such as ion-exchange resin, ion-exchange cellulose and ion-exchange sephadex, and those with which a molecular weight difference is applied, such as molecular sieve carriers. Eluents which can be used in proper combination to elute object compounds from these carriers include an mixed solvent in an appropriate ratio of, for example, a water-miscible organic solvent (e.g. methanol, ethanol, acetone and acetonitrile) and water, an aqueous solution of alkali (e.g. sodium hydroxide, potassium hydroxide and sodium hydrogencarbonate), an aqueous solution of acid (e.g. hydrochloric acid, acetic acid, formic acid and phosphoric acid), and an aqueous solution containing salt (e.g. aqueous saline solution, acetic acid buffer solution and phosphate buffer solution).

To describe in more detail, use is advantageously made of, as the carriers, for example, activated charcoal for chromatographic use (manufactured by Takeda Chemical Industries, Ltd.), Kieselgel 60 (manufactured by Merck A. G., Germany), microcrystalline cellulose [Avicel (manufactured by Asahi Chemical Industries, Co., Ltd.), and Funacel (manufactured by Funakoshi Pharmaceutical Co., Ltd.)], adsorptive resin [e.g. Diaion HP-20 or SP-207 (manufactured by Mitsubishi Chemical Industries, Ltd.), Amberlite XAD-I or II (manufactured by Rohm & Haas, Co., U.S.A.)], cation-exchange resin [e.g. Amberlite IR-120, IRC-50 or CG-50 (manufactured by Rohm & Haas, Co., U.S.A.), Dowex 50W (manufactured by Dow Chemical Co., U.S.A.), Diaion SK1A (manufactured by Mitsubishi Chemical Industries, Ltd.)], anion-exchange resin [e.g. Amberlite IRA-402 or IRA-68 (manufactured by Rohm & Haas, Co., U.S.A.), Dowex 1 (manufactured by Dow Chemical, Co., U.S.A), Diaion SA10B, PA-404 or WA-30 (manufactured by Mitsubishi Chemical Industries, Ltd.)], ion-exchange sephadex [e.g. QAE or CM-Sephadex (manufactured by Pharmacia, Sweden)], and molecular sieve resin [e.g. Sephadex LH-20 (manufactured by Pharmacia, Sweden]. And, aziridin-2,3-dicarboxylic acid is dissolved in an adequate solvent for. crystallization, for example, acetone, methanol, ethanol, water or a mixture of them, then the solution is left standing under cooling to thereby give the compound as crystals.

The compound [I] of this invention can be used as a salt thereof, preferably, a pharmaceutically acceptable salt. As the salt, when the compound [I] has an acidic group such as carboxyl group, mention is made of basic salts, for example, salts with an alkali metal (e.g. sodium and potassium) and salts with an alkaline earth metal (e.g. calcium and magnesium). When the compound [I] has a basic group such as amino group, mention is made of acid addition salts including, for example, salts with an inorganic acid (e.g. hydrochloric acid, sulfuric acid and phosphoric acid) or those with an organic acid (e.g. acetic acid, propionic acid, citric acid, tartaric acid, malic acid, oxalic acid and methanesulfonic acid).

And, as salts of the compound [II]–[X], use is made of similar ones to those of the compound [I].

Structural formulae of the compounds produced by Working Examples described later are shown as follows.

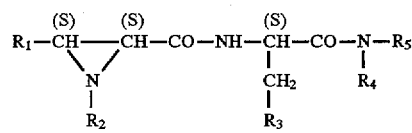

| Cpd. No. | $R_1$ | $R_2$ | $R_3$ | $R_4$ | $R_9$ |
|---|---|---|---|---|---|
| 2 | $COOC_2H_5$ | Z | H | $(CH_2)_2CH(CH_3)_2$ | Ph |
| 3 | $COOC_2H_5$ | H | H | $(CH_2)_2CH(CH_3)_2$ | Ph |
| 4 | COONa | H | H | $(CH_2)_2CH(CH_3)_2$ | Ph |
| 5 | $COOC_2H_5$ | Z | H | $(CH_2)_4NHZ$ | Ph |
| 6 | $COOC_2H_5$ | H | H | $(CH_2)_4NH_2 \cdot \frac{1}{2}H_2SO_4$ | Ph |
| 7 | COOH | H | H | $(CH_2)_4NH_2$ | Ph |
| 8 | $COOC_2H_5$ | Z | | $-(CH_2)_2O(CH_2)_2-$ | Ph |
| 9 | $COOC_2H_5$ | H | | $-(CH_2)_2O(CH_2)_2-$ | Ph |
| 10 | COONa | H | | $-(CH_2)_2O(CH_2)_2-$ | Ph |
| 11 | $COOC_2H_5$ | Z | H | $(CH_2)_2CH(CH_3)_2$ | i-Pr |
| 12 | $COOC_2H_5$ | H | H | $(CH_2)_2CH(CH_3)_2$ | i-Pr |
| 13 | COONa | H | H | $(CH_2)_2CH(CH_3)_2$ | i-Pr |
| 14 | $COOC_2H_5$ | Z | H | $(CH_2)_4NHZ$ | i-Pr |
| 15 | $COOC_2H_5$ | H | H | $(CH_2)_4NH_2 \cdot \frac{1}{2}H_2SO_4$ | i-Pr |
| 16 | COOH | H | H | $(CH_2)_4NH_2$ | i-Pr |
| 17 | $COOC_2H_5$ | Z | | $-(CH_2)_2O(CH_2)_2-$ | i-Pr |
| 18 | $COOC_2H_5$ | H | | $-(CH_2)_2O(CH_2)_2-$ | i-Pr |
| 19 | COONa | H | | $-(CH_2)_2O(CH_2)_2-$ | i-Pr |
| 20 | $COOC_2H_5$ | Z | H | $(CH_2)_3OCH_3$ | i-Pr |
| 21 | $COOC_2H_5$ | H | H | $(CH_2)_3OCH_3$ | i-Pr |
| 22 | COONa | H | H | $(CH_2)_3OCH_3$ | i-Pr |
| 23 | $COOC_2H_5$ | Z | | $-(CH_2)_5-$ | i-Pr |
| 24 | $COOC_2H_5$ | H | | $-(CH_2)_5-$ | i-Pr |
| 25 | COONa | H | | $-(CH_2)_5-$ | i-Pr |
| 26 | $COOC_2H_5$ | H | H | $(CH_2)_3OCH_3$ | Ph |
| 27 | COONa | H | H | $(CH_2)_3OCH_3$ | Ph |
| 28 | $COOC_2H_5$ | H | H | $(CH_2)_5CH_3$ | Ph |
| 29 | COONa | H | H | $(CH_2)_5CH_3$ | Ph |
| 30 | $COOC_2H_5$ | H | H | $CH_2CH=CH_2$ | Ph |
| 31 | COONa | H | H | $CH_2CH=CH_2$ | Ph |
| 32 | $COOC_2H_5$ | H | H | $(CH_2)_3OBu$ | Ph |
| 33 | COONa | H | H | $(CH_2)_3OBu$ | Ph |
| 34 | $COOC_2H_5$ | H | H | $CH_2CH(CH_3)_2$ | Ph |
| 35 | COONa | H | H | $CH_2CH(CH_3)_2$ | Ph |
| 36 | $COOC_2H_5$ | H | H | $(CH_2)_3O(i-Pr)$ | Ph |
| 37 | COONa | H | H | $(CH_2)_3O(i-Pr)$ | Ph |
| 38 | $COOC_2H_5$ | H | H | Furfuryl | Ph |
| 39 | COONa | H | H | Furfuryl | Ph |
| 40 | $COOC_2H_5$ | H | H | Cyclohexyl | Ph |
| 41 | COONa | H | H | Cyclohexyl | Ph |
| 42 | $COOC_2H_5$ | $CH_3$ | H | $(CH_2)_2CH(CH_3)_2$ | Ph |
| 43 | COONa | $CH_3$ | H | $(CH_2)_2CH(CH_3)_2$ | Ph |
| 44 | $COOC_2H_5$ | $C_2H_5$ | H | $(CH_2)_2CH(CH_3)_2$ | Ph |
| 45 | COONa | $C_2H_5$ | H | $(CH_2)_2CH(CH_3)_2$ | Ph |
| 46 | COONa | $COCH_3$ | H | $(CH_2)_2CH(CH_3)_2$ | Ph |
| 47 | $COOC_2H_5$ | H | | $-(CH_2)_5-$ | Ph |

-continued

| Cpd. No. | R₁ | R₂ | R₃ | R₄ | R₉ |
|---|---|---|---|---|---|
| 48 | COONa | H | | —(CH₂)₅— | Ph |
| 49 | COOC₂H₅ | H | H | Piperidino | Ph |
| 50 | COONa | H | H | Piperidino | Ph |
| 51 | COOC₂H₅ | H | H | 1-Pyrrolyl | Ph |
| 52 | COONa | H | H | 1-Pyrrolyl | Ph |
| 53 | COOC₂H₅ | H | H | Ph | Ph |
| 54 | COONa | H | H | Ph | Ph |
| 55 | COOC₂H₅ | H | H | CH₂Ph | Ph |
| 56 | COONa | H | H | CH₂Ph | Ph |
| 57 | COOC₂H₅ | H | H | (CH₂)₂Ph | Ph |
| 58 | COONa | H | H | (CH₂)₂Ph | Ph |
| 59 | COOC₂H₅ | H | H | 1-Adamantyl | Ph |
| 60 | COONa | H | H | 1-Adamantyl | Ph |
| 61 | COOC₂H₅ | H | H | (CH₂)₄Ph | Ph |
| 62 | COONa | H | H | (CH₂)₄Ph | Ph |
| 63 | COOC₂H₅ | H | H | (CH₂)₂(2-pyridyl) | Ph |
| 64 | COONa | H | H | (CH₂)₂(2-pyridyl) | Ph |
| 65 | COOC₂H₅ | H | H | 2-Thiazolyl | Ph |
| 66 | COONa | H | H | 2-Thiazolyl | Ph |
| 67 | COOC₂H₅ | H | H | (CH₂)₃Ph | Ph |
| 68 | COONa | H | H | (CH₂)₃Ph | Ph |
| 69 | COOC₂H₅ | H | CH₃ | CH₂Ph | Ph |
| 70 | COONa | H | CH₃ | CH₂Ph | Ph |
| 71 | COOC₂H₅ | H | H | CH₂(1-naphthyl) | Ph |
| 72 | COONa | H | H | CH₂(1-naphthyl) | Ph |
| 73 | COOC₂H₅ | H | H | CH₂(2-thienyl) | Ph |
| 74 | COONa | H | H | CH₂(2-thienyl) | Ph |
| 75 | COOC₂H₅ | H | H | Tetrahydrofurfuryl | Ph |
| 76 | COONa | H | H | Tetrahydrofurfuryl | Ph |
| 77 | COOC₂H₅ | H | H | 1-Naphthyl | Ph |
| 78 | COONa | H | H | 1-Naphthyl | Ph |
| 79 | COOC₂H₅ | H | H | (CH₂)₂(2-thienyl) | Ph |
| 80 | COONa | H | H | (CH₂)₂(2-thienyl) | Ph |
| 81 | COOC₂H₅ | H | H | CH₂CH(Ph)₂ | Ph |
| 82 | COONa | H | H | CH₂CH(Ph)₂ | Ph |
| 83 | COOC₂H₅ | H | H | (S)—CH(CH₃)Ph | Ph |
| 84 | COONa | H | H | (S)—CH(CH₃)Ph | Ph |
| 85 | COOC₂H₅ | H | H | (R)—CH(CH₃)Ph | Ph |
| 86 | COONa | H | H | (R)—CH(CH₃)Ph | Ph |
| 87 | COOC₂H₅ | H | H | CH₂-cyclohexyl | Ph |
| 88 | COONa | H | H | CH₂-cyclohexyl | Ph |
| 89 | COOC₂H₅ | CH₃ | H | Furfuryl | Ph |
| 90 | COONa | CH₃ | H | Furfuryl | Ph |
| 91 | COOC₂H₅ | CH₃ | H | CH₂Ph | Ph |
| 92 | COONa | CH₃ | H | CH₂Ph | Ph |
| 93 | COOC₂H₅ | CH₃ | H | (CH₂)₂Ph | Ph |
| 94 | COONa | CH₃ | H | (CH₂)₂Ph | Ph |
| 95 | COOC₂H₅ | CH₂Ph | H | CH₂Ph | Ph |
| 96 | COONa | CH₂Ph | H | CH₂Ph | Ph |
| 97 | COOC₂H₅ | CH₂Ph | H | (CH₂)₂Ph | Ph |
| 98 | COONa | CH₂Ph | H | (CH₂)₂Ph | Ph |
| 99 | COOC₂H₅ | CH₂Ph | H | CH₂(1-naphthyl) | Ph |
| 100 | COONa | CH₂Ph | H | CH₂(1-naphthyl) | Ph |
| 101 | COOC₂H₅ | CH₃ | H | CH₂(1-naphthyl) | Ph |
| 102 | COONa | CH₃ | H | CH₂(1-naphthyl) | Ph |
| 103 | COOC₂H₅ | CH₂CH=CH₂ | H | CH₂(1-naphthyl) | Ph |
| 104 | COONa | CH₂CH=CH₂ | H | CH₂(1-naphthyl) | Ph |
| 105 | COONa | CHO | H | (CH₂)₂CH(CH₃)₂ | Ph |
| 106 | COOC₂H₅ | Z | H | (CH₂)₂CH(CH₃)₂ | 2-Naphthyl |
| 107 | COOC₂H₅ | H | H | (CH₂)₂CH(CH₃)₂ | 2-Naphthyl |
| 108 | COOH | H | H | (CH₂)₂CH(CH₃)₂ | 2-Naphthyl |
| 109 | COOC₂H₅ | Z | H | CH₂Ph | 2-Naphthyl |
| 110 | COOC₂H₅ | H | H | CH₂Ph | 2-Naphthyl |
| 111 | COONa | H | H | CH₂Ph | 2-Naphthyl |
| 112 | COOC₂H₅ | H | CH₃ | (CH₂)₂Ph | Ph |
| 113 | COONa | H | CH₃ | (CH₂)₂Ph | Ph |
| 114 | COOC₂H₅ | H | H | (S)—CHCH₂Ph<br>\|<br>COOCH₂Ph | Ph |
| 115 | COONa | H | H | (S)—CHCH₂Ph<br>\|<br>COONa | Ph |
| 116 | CONHC₃H₇ | H | H | (CH₂)₂CH(CH₃)₂ | Ph |
| 117 | COOCH₂Ph | H | H | (CH₂)₂Ph | Ph |

-continued

| Cpd. No. | R₁ | R₂ | R₃ | R₄ | R₉ |
|---|---|---|---|---|---|
| 118 | COOPOM | H | H | (CH₂)₂Ph | Ph |
| 119 | COOC₂H₅ | H | H | CH₂Ph(p-Cl) | Ph |
| 120 | COONa | H | H | CH₂Ph(p-Cl) | Ph |
| 121 | COOC₂H₅ | H | H | (CH₂)₂Ph(p-Cl) | Ph |
| 122 | COONa | H | H | (CH₂)₂Ph(p-Cl) | Ph |
| 123 | COOC₂H₅ | H | H | (CH₂)₂Ph(p-OCH₃) | Ph |
| 124 | COONa | H | H | (CH₂)₂Ph(p-OCH₃) | Ph |
| 125 | COOC₂H₅ | H | H | CH₂Ph(p-CF₃) | Ph |
| 126 | COONa | H | H | CH₂Ph(p-CF₃) | Ph |
| 127 | COOC₂H₅ | H | CH₃ | (CH₂)₂(2-pyridyl) | Ph |
| 128 | COONa | H | CH₃ | (CH₂)₂(2-pyridyl) | Ph |
| 129 | COOC₂H₅ | H | CH₃ | CH₂(1-naphthyl) | Ph |
| 130 | COONa | H | CH₃ | CH₂(1-naphthyl) | Ph |
| 131 | COOC₂H₅ | H | CH₃ | (CH₂)₂Ph | (p-OH)Ph |
| 132 | COONa | H | CH₃ | (CH₂)₂Ph | (p-OH)Ph |
| 133 | COOC₂H₅ | H | CH₃ | CH₂(1-naphthyl) | (p-OH)Ph |
| 134 | COONa | H | CH₃ | CH₂(1-naphthyl) | (p-OH)Ph |

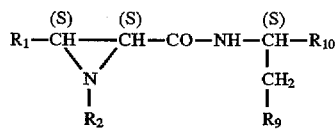

| Cpd. No. | R₁ | R₂ | R₁₀ | R₉ |
|---|---|---|---|---|
| 26a | COOC₂H₅ | Z | COOCH₂Ph | Ph |
| 26b | COOC₂H₅ | H | COOH | Ph |

(S) and (R) show that the carbon atoms bearing the symbols are S- and R-configuration, respectively; Ph represents phenyl group; i-Pr represents isopropyl group; Bu represents butyl group; POM represents pivaloyloxymethyl group.

The bioactivities of the compounds of this invention are described below. The compounds [I] or salts thereof have activities of inhibiting cathepsin L and cathepsin B, and of potently inhibiting thiol protease. Their inhibitory activities against cathepsin L were determined by the methods described below.

Determination of cathepsin L inhibitory activity

To 75 µl of a reaction mixture containing 1 ng of human recombinant cathepsin L (as produced in Reference Examples 1 through 7 below), 2 µM of dithiothreitol (hereinafter abbreviated as DTT), 1 mM of ethylenediamine tetraacetate disodium salt, a 0.1M sodium acetate buffer solution (pH 5.5) and various concentrations of test samples, 25 µl of 20 µM benzyloxycarbonyl-L-phenylalanyl-L-arginine-4-methylcoumaryl-7-amide (hereinafter abbreviated as Z-Phe-Arg-7MCA, manufactured by Peptide Institute) was added to initiate the reaction. After incubation at 37° C. for 20 minutes, 100 µl of a reaction stopper solution containing 100 mM sodium monochloroacetate was added. The amount of liberated 4-methyl-7-aminocoumarin was determined at an excitation wavelength of 365 nm and a fluorescence wavelength of 450 nm, using a fluorophotometer (FCA:manufactured by Baxter Travenol). The sample concentration required to cause 50% inhibition was expressed as the IC₅₀ value, with the fluorescence value obtained from the same reaction in the absence of the sample taken as 100%. The results are shown in Table 1.

TABLE 1

| Compound No. | Inhibitory activity potency IC₅₀ (ng/ml) Cathepsin L |
|---|---|
| 4 | 5 |
| 7 | 3 |
| 43 | 0.2 |
| 45 | 0.1 |

The compounds [I] or salts thereof of this invention show suppressive action against bone resorption as enhanced by PTH (parathyroid hormone), and the action was determined by method described below. The results are shown in Table 2. Determination of bone resorption suppressive activity Femurs were aseptically isolated from female BALB/c mice at 8–10 weeks of age. After the bone marrow cavity was washed with a Ham F12 medium containing 10 weight % thermally inactivated fetal calf serum, 100 unit/ml penicillin G and 100 unit/ml streptomycin (hereinafter referred to as culture broth), each femur was added to 1 ml of the culture broth and precultured for 3 hours at 37° C. in the presence of 5% carbon dioxide and 95% air. Each bone was transferred to 1 ml of the culture broth supplemented with PTH (manufactured by Peptide Institute, Inc., final concentration 1 µM) and the test compound (final concentration 10 µg/ml) and cultured for 7 more days, after which the total calcium content in the culture broth was determined using Calcium E-Test Wako (manufactured by Wako Pure Chemical Industries, Ltd.). The bone resorption suppressive activity of the test compound was calculated using the following equation.

Bone resorption suppressive activity (%)=100×(Cp-Cs)/(Cp-Cc)

Cc: Total calcium content in the culture broth containing neither PTH nor test compound Cp: Total calcium content in the culture broth containing PTH Cs: Total calcium content in the culture broth containing both PTH and test compound

TABLE 2

| Compound No. | Bone resorption suppressive activity (%) |
|---|---|
| 7 | 99 |

Toxicity study

Compound 4 caused no death in mice when it was intravenously or intraperitoneally administered at 1,000 mg/kg.

As described hereinbefore, the compounds [I] or salts thereof have an inhibitory activity against substances having a thiol group as an active center such as thiol protease [e.g. cathepsins (e.g. cathepsin L, cathepsin B, cathepsin K), calpains (e.g. calpain I, calpain II)], which can be used as thiol protease inhibitory agents being useful for prophylactic and therapeutic agents for diseases caused by thiol protease (e.g. muscular dystrophy, aerocystic distal myopathy, myocardial infarction, brain infarction, thrombosis, cataract, Alzheimer's disease, muscle atrophy, cancer metastasis). Besides, since substances inhibiting thiol protease show an anti-inflammatory activity, the thiol protease inhibitory agent of the present invention can be used as an anti-inflammatory agent as well.

Further, the compounds [I] or salts thereof have bone resorption suppressive activity, which are used as prophylactic and therapeutic agents for bone diseases such as osteoporosis, hypercalcemia in malignancy and Paget's diseases.

The compounds [I] or salts thereof are low in toxicity, which can be safely used for mammals (e.g. dogs, cats, horses, monkeys and man).

When the compound [I] or a salt thereof is administered to, for example, man, it can be safely administered orally or non-orally as such, or in a pharmaceutical composition along with an appropriate pharmacologically acceptable carrier, excipient and diluent.

The pharmaceutical compositions described above include, as oral preparations, for example, powdery preparations, granular preparation, capsules and tablets, and, as non-oral preparations, for example, injections, instillations, medicines for external application (e.g. nasal drops and transdermal preparations), suppositories (e.g. rectal suppositories and vaginal suppositories).

These preparations can be produced by per se known methods in common use for pharmaceutical formulation steps.

The compounds [I] or salts thereof can be formulated as an oral preparation by compressive shaping in the presence of an excipent (e.g. lactose, sucrose, starch and mannitol), a disintegrating agent (e.g. calcium carbonate and carboxymethyl cellulose calcium), a binder (e.g. α-starch, gum arabic, carboxymethyl cellulose, polyvinylpyrrolidone, hydroxypropyl cellulose) or a lubricant (e.g. talc, magnesium stearate and polyethylene glycol 6000) and other additives, followed by coating if necessary for the purpose of taste masking, enteric release or sustained release by a per se known method. Coating agents for this purpose include ethyl cellulose, hydroxymethyl cellulose, polyoxyethylene glycol, cellulose acetate phthalate, hydroxypropylmethyl cellulose phthalate and Eudragit (manufactured by Roehm Pharma GmbH, Germany, methacrylic acid acrylic acid copolymer).

The compounds [I] or salts thereof can be formulated into an aqueous injection along with a dispersing agent [e.g. Tween 80 (manufactured by Atlas Powder, U.S.A.), HCO 60 (manufactured by Nikko Chemicals), polyethylene glycol, carboxymethyl cellulose and sodium alginate], a preservative (e.g. methyl paraben, propyl paraben, benzyl alcohol and chlorobutanol), an isotonizing agent (e.g. sodium chloride, glycerol, sorbitol and glucose) and other additives, or into an injection in oil by dissolving, suspending or emulsifying in a vegetable oil (e.g. olive oil, sesame oil, cotton seed oil and corn oil and propylene glycol).

The compounds [I] or salts thereof can also be formulated into a medicine for external application by preparing into a solid, semi-solid or liquid composition. The solid composition, for example, is prepared by pulverizing the compound of this invention as it is, or after mixing with an excipient (e.g. lactose, mannitol, starch, microcrystalline cellulose and sucrose), a thickening agent (e.g. natural rubber, cellulose derivatives and acrylic acid polymers). The liquid composition can be prepared, by substantially the same process as in the case of injectable preparations, by formulating into an oil or aqueous suspension. The semi-solid composition is in the state of, preferably aqueous or oily gel form or cartilage-like. And, these compositions may contain, for example, a pH controlling agent (e.g. carbonic acid, phosphoric acid, citric acid, hydrochloric acid and sodium hydroxide) and a preservative (e.g. p-hydroxybenzoic acid esters, chlorobutanol and benzalkonium chloride).

The suppository can be prepared by formulating the compound [I] or a salt thereof into an oily or aqueous solid, semi-solid or liquid composition. Examples of the oleaginous base used for the said composition include glyceride of higher fatty acid [e.g. cacao butter and Witepsols (manufactured by Dynamite Nobel A.S.)], middle fatty acid [e.g. migtiols (manufactured by Dynamite Nobel A.S.)] or vegetable oil (e.g. sesame oil, soybean oil and cotton seed oil). Examples of the aqueous base include polyethylene glycols and propylene glycol. And, examples of the aqueous gel base include natural rubbers, cellulose derivatives, vinyl polymers and acrylic acid polymers.

When the compound [I] or a salt thereof is administered as a prophylactic and therapeutic agent of bone diseases in oral administration to an adult patient weighing 50 kg, the daily dose is normally 1 mg to 2 g, preferably about 10 mg to 2 g, more preferably about 20 mg to 1 g, based on active ingredient content, varying depending on the target disease, route of administration, age of individual subject patient and severity of disease.

When the compound [I] or a salt thereof is administered to man as an agent of inhibiting thiol protease, the dose is substantially the same as that in the case of using as prophylactic and therapeutic agent of above-mentioned bone diseases.

The present invention is hereinafter described in detail by means of, but not limited to, the following Reference Examples, Working Examples and Formulation Examples. Incidentally, percent (%) means, unless otherwise specified, percent by weight/volume. Numeral values for mixing ratios of mixed solvents are based on volume.

NMR spectra were taken using the Bruker AC-300 spectrometer ($^1$H NMR, 300 MHz; $^{13}$C NMR, 75 MHz) or Varian Gemini 200 spectrometer ($^1$H NMR, 200 MHz). As the internal standard, use is made of 3-(trimethylsilyl) propionic acid-$d_4$ sodium salt in heavy water, while tetramethylsilane in other solvents, and all δ values are expressed by ppm. The symbols used in the present specification have the following meanings: Q, quaternary carbon; s, singlet; d, doublet; t, triplet; q, quartet; dd, double doublet; dt, double triplet; m, multiplet; br., broad; CH, methine; $CH_2$, methylene; and $CH_3$, methyl.

REFERENCE EXAMPLE 1

(Cloning cathepsin L cDNA of human renal origin)

To amplify human cathepsin cDNA by the polymerase chain reaction (PCR) method, four primers were synthesized in accordance with a reported base sequence of cathepsin L of human renal origin [S. Gal and M. M. Gottesman, Biochemical Journal, Vol.253, p.303 (1988)] as follows.

Sense.primer No.1:
  5'-TTTTCAGGGGGCAGTAAGAT-3'
Sense.primer No.2:
  5'-pCCGGATCCGGCTTTTTAGGATTGGTCTA-3'
Antisense.primer No.3:
  5'-GGGGGCTGGTAGACTGAAGA-3'
Antisense.primer No.4
  5'-pCCGGATCCATTCCTCCCATGCATGCGCC-3'

Three µl of a solution of human renal cDNA library λ gt11 (CLONTECH Laboratories, Inc.) and 50 µl of distilled water were mixed. After incubation at 95° C. for 5 minutes, the mixture was immediately cooled in ice. Two primers (No. 1 and No. 3 above; 50 pmol each) were added, and reaction was carried out as directed in the instruction manual for the kit supplied by Cetus/Perkin-Elmer, in which a series of reactions at 94° C. for one minutes, 55° C. for two minutes and 72° C. for three minutes were repeated in 50 cycles. To the reaction mixture, two other primers (No. 2 and No. 4; 50 pmol each) were added, and the same reaction as above was conducted. The PCR product was separated by electrophoresis on 1.2% agarose gel; an amplified DNA fragment was detected at a position corresponding to the size (1132 bp) expected from the base sequence of cathepsin L of human renal origin. This DNA fragment was recovered from the gel and subcloned to the plasmid vector pBluescript® II SK+ (produced by STRATAGENE). The base sequence of the cDNA portion was determined by the dideoxynucleotide synthetic chain termination method [J. Messing et al., Nucleic Acid Research, Vol.9, p.309 (1981); it proved identical with the reported sequence. The plasmid containing this cDNA fragment was named pHCL-5.

REFERENCE EXAMPLE 2

(Expression of human cathepsin L in *Escherichia coli* MM294(DE3))

The cDNA of Reference Example 1 was cleaved with restriction enzyme EcoRI, and a 798 bp fragment (which encodes a part of the human cathepsin L precursor and the whole matured human cathepsin L) was recovered. To both ends of this fragment was ligated a BamHI linker (5'-pCCCGGATCCGGG-3'), and the ligation product was inserted to the plasmid vector pET-3c for expression in *Escherichia coli* [Methods in Enzymology, ed. D. V. Goeddel, Vol.185, p.68, Academic Press (1990)]. The thus-constructed plasmid was designated as pET-HClα. *Escherichia coli* MM294(DE3) was transformed with pET-HClα to express human cathepsin L in the presence of the T7 promoter [Methods in Enzymology, Vol.185, p.60 (1990)]. The thus-obtained *Escherichia coli* transformant [*Escherichia coli* JM109/pTBN-HClneo, harboring the plasmid pTBN-HClneo, has been deposited under accession number IFO 15341 at the Institute for Fermentation, Osaka (IFO) since Jun. 12, 1992, and under accession number FERM BP 3897 at the National Institute of Bioscience and Human-Technology (NIBH), Agency of Industrial Science and Technology, Ministry of International Trade and Industry, since Jun. 22, 1992] was cultured, and cells were disrupted by sonication and subjected to SDS-PAGE; a unique band appeared near 30 kDal, corresponding to human cathepsin L. Since the expressed product formed an inclusion body, human cathepsin L was roughly purified from the precipitate fraction of the ultrasonically disrupted transformant.

REFERENCE EXAMPLE 3

(Preparation of antiserum to recombinant human cathepsin L)

The roughly purified recombinant human cathepsin L described in Reference Example 2 was mixed with an equal amount of Freund's complete adjuvant, and about 1 ml was inoculated to a rabbit. Later, a mixture of a roughly purified human cathepsin L specimen and an equal amount of of Freund's incomplete adjuvant was injected 3 times at 10-day intervals, and blood was collected seven days after the final injection. The blood thus collected was left standing at 37° C. for 30 minutes and then at 4° C. overnight, which was then subjected to centrifugal separation to yield a human cathepsin L antiserum.

REFERENCE EXAMPLE 4

(Preparation of recombinant DNA for expression of human cathepsin L gene in animal cells)

After the plasmid pHCL-5, described in Reference Example 1, was digested with restriction enzyme BamHI, a fragment of human cathepsin L cDNA was recovered by agarose gel electrophoresis. Subsequently, this cDNA fragment was inserted to the restriction enzyme Bgl II site of the vector pTB551 for transient expression in animal cells [prepared by converting the EcoRI to Bgl II site in the plasmid pTB389 described by Ono et al. in Science, Vol.236, p.1116 (1989)] by the action of T4 DNA ligase and ATP, to yield the expression plasmid pTB-HCl. MuLV-LTR was inserted between the restriction enzyme HindIII and ClaI sites of pTB-HCl to yield the expression plasmid pTBN-HCL.

REFERENCE EXAMPLE 5

(Preparation of recombinant DNA for expression of human cathepsin L gene in animal cells)

To obtain an animal cell line that stably expresses human cathepsin L, the drug resistance marker neogene was inserted to the recombinant vector pTBN-HCL described in Reference Example 4 in the following manner: first, a fragment comprising the SV40 early promoter and the neogene was inserted between the restriction enzyme ClaI and Sal I sites of plasmid pTBN-HCL to yield the plasmid pTBN-HCLneo.

REFERENCE EXAMPLE 6

(Expression of human cathepsin L gene in animal cells)

Using the plasmid described in Reference Example 5 (pTBN-HCLneo), mouse myeloma Sp2/0 cells were transformed as follows: Sp2/0 cells, cultivated in an ASF104 medium supplemented with 5% fetal calf serum (FCS) (5% FCS/ASF medium), were suspended in phosphate-buffered saline (PBS) (−)[the same as Dulbecco's PBS but $CaCl_2$ and $MgCl_2$ were removed] to adjust $1\times10^7$ cells/ml. Five hundred µl of this cell suspension was injected to to a cuvette, 10 µg of said plasmid DNA was added, and the mixture was left standing on ice for 5 minutes. This liquid was pulsated at 125 μF and 300 V, using a gene pulser (manufactured by Bio-Rad Laboratories), and then again left standing on ice for 10 minutes. This liquid was transferred to 10 ml of a 5% FCS/ASF104 medium and cultured at 37° C. in the presence of 5% carbon dioxide. Forty-eight hours later, the culture was transferred to a selection medium (5% FCS/ASF104 medium containing 200 μg/ml G418) and cultured on a 24-well plate for two weeks. A number of colonies emerged, each of which was transferred to an ASF10 medium containing 200 μg/ml G418 and cultured, followed by Western blot analysis of the culture supernatant using the human cathepsin L antiserum prepared in Reference Example 3. In response to the antiserum, unique bands corresponding to molecular weights of about 40,000 to 30,000 and lower molecular weights appeared; they were identified as a precursor of human cathepsin L and a product processed therefrom, estimated from these molecular weights. The culture supernatant was assayed for cathepsin L activity, in accordance with the method of A. J. Barrett and H. Kirschke [Methods in Enzymology, Vol.80, p.535 (1981)]; human cathepsin L activity was detected.

These findings confirm that transformant mouse myeloma cells expressing cathepsin L were obtained, which were designated as the mouse myeloma Sp-HCL26.

REFERENCE EXAMPLE 7

(Purification of human cathepsin L)

The strain obtained in Reference Example 6, showing high expression of cathepsin L, (the mouse myeloma Sp-HCL26, transformed with the plasmid pTBN-HCLneo, has been deposited under accession number IFO 50371 at the Institute of Fermentation, Osaka (IFO) since Jun. 16, 1992, and under accession number FERM BP 3902 at the National Institute of Bioscience and Human-Technology (NIBH), Agency of Industrial Science and Technology, Ministry of International Trade and Industryl since Jun. 24, 1992) was cultured in 20 ml of an ASF104 medium supplemented with 10% FCS and 200 μg/ml G418, after which it was transferred to 50 ml of a serum-free selection medium (ASF104 medium supplemented with 200 μg/ml G418) and cultured for 5 days. After the culture supernatant was applied to a column of CM-Sephadex C-50 (25×4.4 cm), the column was washed with buffer A (20 mM sodium acetate, 1 mM EDTA, pH 5.5), followed by elation on a sodium chloride (NaCl) density gradient from 0 to 1M, to elute human cathepsin L near an NaCl concentration of about 0.4M. This fraction was applied to the Mono S column ($HR_{5/5}$) of an FPLC system (manufactured by Pharmacia), followed by column washing and human cathepsin L elution in the same manner as above. The human cathepsin L fraction, eluted near an NaCl concentration of about 0.36M, was concentrated to yield a purified standard preparation.

REFERENCE EXAMPLE 8

Preparation of culture broth containing (2S,3S)-aziridine-2,3-dicarboxylic acid

Streptomyces sp.116-20 (IFO 15746) strain grown on yeast extract.malt extract agar slant medium was inoculated to 40 ml of a seed medium (pH 7.0) containing 2% glucose, 3% soluble starch, 1% soybean flour, 1% corn steep liquor, 0.5% peptone, 0.3% NaCl and 0.5% $CaCO_3$ in a 200 ml Erlenmeyer flask, and cultured at 28° C. for 48 hours on a rotary shaker to give a pre-culture broth. Five ml of thus-prepared pre-culture was transplanted to 500 ml of a seed medium in a 2000 ml Sakaguchi's flask, which was cultured at 28° C. for 48 hours on a reciprocal shaker to give a seed culture broth. Five hundred ml of this seed culture medium was transplanted to 120 liters of a main culture medium (pH 7.0) containing 0.5% glucose, 5% dextrin, 3.5% defatted soybean, 0.0002% $CoCl_2$ and 0.7% $CaCO_3$ in a 200 liter stainless steel tank. The fermentation was carried out at 28° C. for 96 hours with aeration of 120 liters/min., agitation of 120 rpm and inner pressure of 1 $kg/cm^2$.

REFERENCE EXAMPLE 9

Purification of (2S,3S)-aziridine-2,3-dicarboxyl acid

The culture broth (100 liters) obtained in Reference Example 8 was filtered using a filter aid (Radiolite 600, manufactured by Showa Chemical Industry). After adjustment to pH 6.8, the filtrate (90 liters) was subjected to a column chromatography on activated carbon (10 liters), and the column was washed with water (10 liters). The effluent and the washing were combined, which was subjected to a column chromatography on Amberlite 120 (H type, 15 liters), and the column was washed with water (15 liters). The effluent and the washing were combined, which was concentrated to a volume of 4.3 liters. The concentrate was left standing at 4° C., then resulting precipitate was collected by filtration. Recrystallization of the crude crystals (128 g) afforded (2S,3S)-aziridine-2,3-dicarboxylic acid as crystals (94 g).

$[\alpha]_D^{28} +53°$ (c 0.47, $H_2O$) Elemental Analysis for $C_4H_5NO_4$: Calcd.: C; 36.65, H; 3.84, N; 10.68 (%) Found: C; 36.56, H; 3.87, N; 10.46 (%)

WORKING EXAMPLE 1

(2S,3S)-Ethyl hydrogen N-Z-aziridine-2,3-dicarboxylate (2S,3S)-aziridine-2,3-dicarboxylic acid (10.4 g), which is disclosed in JPA S52(1977)-38091 or Tetrahedron Vol.47 p.5287 (1991), was dissolved in a 4N aqueous solution of sodium hydroxide (40 ml). To the solution were added dropwise, under ice-cooling, a 4N aqueous solution of sodium hydroxide (24 ml) and Z-chloride (12.6 ml, manufactured by Wako Pure Chemical Industries, Ltd.), in the course of 40 minutes, then the mixture was stirred for 3 hours. To the reaction mixture were added dropwise, under ice-cooling, a 4N aqueous solution of sodium hydroxide (12 ml) and Z-chloride (6.3 ml), taking 40 minutes. The same process was conducted once more. The reaction mixture was stirred for 3 hours under ice-cooling, and then for 14 hours at room temperature. To the reaction mixture was added water (400 ml), which was washed with ether (150 ml×3). The aqueous layer was adjusted to pH 2.5, which was saturated with sodium chloride, followed by extraction with ethyl acetate (200 ml×4). The ethyl acetate layer was washed with a saturated aqueous saline solution, dried over anhydrous sodium sulfate, followed by concentration to dryness to give (2S,3S)-N-Z-aziridine-2,3-dicarboxylic acid (19.6 g) (yield 92%). The compound thus produced Was dissolved in N,N-dimethylformamide (DFLF, 200 ml), to which were added potassium carbonate (12.3 g) and ethyl iodide (14.2 ml), and then the mixture was stirred for 14 hours at room temperature. The reaction mixture was concentrated, to which was added ethyl acetate, followed by washing with water. The organic layer was dried over anhydrous sodium sulfate, which was subjected to a silica gel column chromatography (1000 ml). Elution was conducted with eluents prepared by adding ethyl acetate to hexane in sequence. From the fraction of eluate with 15% (V/V) ethyl acetate, (2S,3S)—N-Z-aziridine-2,3-dicarbioxylic acid diethyl ester (11.3 g) as a colorless oily product (yield 48%). The compound thus produced was dissolved in ethanol (380 ml). To the solution was added, Under ice-cooling, 1N aqueous solution of sodium hydroxide (35.2 ml), and the mixture was stirred for 30 minutes. The reaction mixture was adjusted to pH 7.5, which was then concentrated. To the concentrate was added water (150 ml), which was washed with ether (100 ml×3). The aqueous layer was adjusted to pH 2.5, followed by extraction with ethyl acetate (150 ml×2). The ethyl acetate layer was washed with a saturated aqueous saline solution, dried over anhydrous sodium sulfate, and concentrated to dryness to afford the above-titled compound (Compound 1; 9.23 g) (yield 89%).

$^1$H NMR δ ppm (300 MHz, CDCl$_3$) 1.27(3H,t,J=7.2 Hz), 3.41(1H,d,J=2.3 Hz), 3.44(1H,d,J=2.3 Hz), 4.20(2H,m), 5.14(1H,d,J=12.1 Hz), 5.20(1H,d,J=12.1 Hz), 7.34(5H,m)

WORKING EXAMPLE 2

N-[N-[(2S,3S)—N-Z-3-ethoxycarbonylaziridine-2-carbonyl]-L-phenylalanyl]isopentylamine Isopentylamine (3.00 ml, manufactured by Wako Pure Chemical Industries, Ltd.) and Boc-L-phenylalanine (7.52 g, manufactured by Peptide Institute, Inc.) were dissolved in dichloromethane (50 ml). To the solution were added, under ice-cooling, HOBT (3.84 g) and WSC (5.44 g). The mixture was stirred for 18 hours at room temperature. The reaction mixture was concentrated, to which was added ethyl acetate (300 ml). The mixture was washed with a 10% aqueous solution of citric acid, a 3% aqueous solution of sodium hydrogen carbonate and a saturated aqueous saline solution. The organic layer was dried over anhydrous sodium sulfate, which was then concentrated to dryness. The concentrate was treated with ether to give N-(Boc-L-phenylalanyl)isopentylamine (7.77 g) (yield 90%). The compound thus obtained (1.00 g) was dissolved in dichloromethane (5 ml), to which was added trifluoroacetic acid (TFA, 5 ml), and the mixture was left standing for one hour at room temperature. The reaction mixture was concentrated, to which was added chloroform, followed by washing with a saturated aqueous solution of sodium hydrogen carbonate, water and a saturated aqueous saline solution, successively. The organic layer was dried over anhydrous sodium sulfate, which was then concentrated to dryness. The residue was dissolved in dichloromethane (26 ml). To the solution were added, under ice-cooling, (2S,3S)-ethyl hydrogen N-Z-aziridine-2,3-dicarboxylate (Compound 1, 965 mg) obtained in Working Example 1, HOBT (445 mg) and WSC (631 mg). The mixture was stirred for 18 hours at room temperature. The reaction mixture was concentrated, to which was added ethyl acetate. The mixture was washed with a 10% aqueous solution of citric acid, water, a saturated aqueous solution of sodium hydrogen carbonate, a 2% aqueous solution of sodium hydrogen carbonate, water and a saturated aqueous saline solution, successively. The organic layer was dried over anhydrous sodium sulfate, which was subjected to a silica gel column chromatography (Kieselgel 60 (Merck A.G.), 200 ml). The column was subjected to elution with eluents prepared by adding methanol to chloroform in sequence. From the fraction of chloroform containing 1% (V/V) methanol, the above-titled compound (Compound 2; 1.15 g) was obtained as a white powdery product (yield 76%).

$[α]_D^{21}$+26° (c 0.45, CHCl$_3$) Elemental Analysis for C$_{28}$H$_{35}$N$_3$O$_6$: Calcd.: C; 65.99, H; 6.92, N; 8.25 (%) Found: C; 66.10, H; 6.95, N; 8.38 (%) $^1$H NMR δ ppm (300 MHz, CDCl$_3$) 0.83(3H,d,J=6.6 Hz), 0.84(3H,d,J=6.6 Hz), 1.22 (2H,dt,J=7.3,7.3 Hz), 1.24(3H,t,J=7.1 Hz), 1.42(1H,m), 2.96 (1H,d,J=2.5 Hz), 2.98(1H,d,J=8.0 Hz), 3.15(2H,m), 3.37 (1H,d,J=2.4 Hz), 4.15(2H,m), 4.50(1H,dt,J=7.7,7.7 Hz), 5.10(1H,d,J=12.0 Hz), 5.19(1H,d,J=12.0 Hz), 5.53(1H,t,J= 5.7 Hz), 6.90(1H,d,J=8.0 Hz), 7.16(2H,m), 7.20–7.38(8H, m)

WORKING EXAMPLE 3

N-[N-[(2S,3S)-3-Ethoxycarbonylaziridine-2-carbonyl]-L-phenylalanyl]isopentylamine The compound 2 produced in Working Example 2 (1.00 g) was dissolved in ethanol (35 ml). To the solution were added water (15 ml), 1N sulfuric acid (0.98 ml) and Pd-C (10%(w/w), manufactured by Engelhard A.G., 100 mg). The mixture was stirred for one hour at room temperature under the atmosphere of hydrogen gas. The catalyst was filtered off, and the filtrate was adjusted to pH 3, which was then concentrated. Resulting precipitate was collected by filtration, washed with water and dried to afford the above-titled compound (Compound 3; 610 mg) as a white powdery product (yield 83%).

$[α]_D^{21}$+33° (c 0.61, CHCl$_3$) Elemental Analysis for C$_{20}$H$_{29}$N$_3$O$_4$: Calcd.: C; 63.98, H; 7.79, N; 11.19 (%) Found : C; 63.77, H; 7.58, N; 11.29 (%) $^1$H NMR δ ppm (300 MHz, CDCl$_3$) 0.85(3H,d,J=6.5 Hz), 0.86(3H,d,J=6.5 Hz), 1.26 (2H,m), 1.30(3H,t,J=7.2 Hz), 1.45(1H,m), 1.74(1H,t,J=8.4 Hz), 2.22(1H,dd,J=2.2,7.8 Hz), 2.78(2H,dd,J=2.2,9.0 Hz), 2.96(1H,dd,J=7.7,13.8 Hz), 3.07(1H,dd,J=7.4,13.8 Hz), 3.18(2H,m), 4.21(2H,q,J=7.1 Hz), 4.51(1H,dt,J=8.2,7.7 Hz), 5.88(1H,t,J=4.8 Hz), 6.96(1H,d,J=8.3 Hz), 7.17(2H,m), 7.28 (3H,m)

WORKING EXAMPLE 4

N-[N-[(2S,3S)-3-Carboxyaziridine-2-carbonyl]-L-phenylalanyl]isopentylamine sodium salt The compound 3 produced in Working Example 3 (500 mg) was dissolved in methanol (25 ml). To the solution was added, under ice-cooling, 1N aqueous solution of sodium hydroxide (2.66 ml). The mixture was stirred for one hour under ice-cooling, and for one hour at room temperature. The reaction mixture was adjusted to pH 6.0, which was then concentrated. The concentrate was subjected to a column chromatography using Diaion HP-20 (manufactured by Mitsubishi Chemical Industries, Ltd., 50 ml). The column was washed with water, then elution was conducted with 50% (V/V) methanolic water to give the above-titled compound (Compound 4; 475 mg) as a white powdery product (yield 97%).

$[α]_D^{21}$+70° (c 0.59, H$_2$O) Elemental Analysis for C$_{18}$H$_{24}$N$_3$O$_4$Na.H$_2$O: Calcd.: C; 55.80, H; 6.76, N; 10.85, Na; 5.94 (%) Found: C; 55.74, H; 6.64, N; 11.08, Na; 5.67 (%) $^1$NMR δ ppm (300 MHz, D$_2$O) 0.80(3H,d,J=6.4 Hz), 0.81(3H,d,J=6.5 Hz), 1.20(2H,m), 1.30(1H,m), 2.44(1H,d, J=2.5 Hz), 2.72(1H,d,J=2.5 Hz), 3.05(2H,m), 3.13(2H,m), 4.49(1H,t,J=7.7 Hz), 7.26(2H,m), 7.36(3H,m)

WORKING EXAMPLE 5

N-Z—N'-[N-[(2S,3S)-N-Z-3-Ethoxycarbonylaziridine-2-carbonyl]-L-phenylalanyl]-1,4-diaminobutane In substantially the same manner as Working Example 2, N-Z-1,4-diaminobutane (1.00 g) disclosed in Hoppe-Seylers Z. Physiol. Chem. 349, p.251 (1968) was condensed with Boc-L-phenylalanine (1.31 g) to yield N-Z-N'-(Boc-L-phenylalanyl)-1,4-diaminobutane (1.89 g) as a white powdery product (yield 90%). The Boc group was deprotected with TFA, and 506 mg of thus-obtained compound was condensed with (2S,3S)-ethyl hydrogen N-Z-aziridine-2,3-dicarboxylate (Compound 1,400 mg) to afford the above-titled compound (Compound 5; 647 mg) as a white powdery product (yield 73%).

$[\alpha]_D^{21}$+3.7° (c 0.52, $CHCl_3$) Elemental Analysis for $C_{35}H_{40}N_4O_8$: Calcd.: C; 65.20, H; 6.25, N; 8.69 (%) Found: C; 64.99, H; 6.20, N; 8.82 (%) $^1$H NMR δ ppm (300 MHz, $CDCl_3$) 1.23(3H,t,J=7.2 Hz), 1.37(4H,m), 2.95(1H,d,J=2.5 Hz), 2.99(1H,m), 3.11(1H,m), 3.15(4H,m), 3.38(1H,d,J=2.5 Hz), 4.14(2H,m), 4.53(1H,m), 4.86(1H,br s), 5.09(2H,s), 5.09(1H,d,J=11.9 Hz), 5.18(1H,d,J=12.0 Hz), 5.92(1H,br s), 6.93(1H,d,J=8.1 Hz), 7.15(2H,m), 7.18–7.38(13H,m)

WORKING EXAMPLE 6

N-[N-[(2S,3S)-3-Ethoxycarbonylaziridine-2-carbonyl]-L-phenylalanyl]-1,4-diaminobutane ½ sulfate In substantially the same manner as Working Example 3, Compound 5 (500 mg) was subjected to catalytic reduction to thereby deprotect the Z group. The resultant compound was subjected to a column chromatography using Diaion HP-20 (50 ml). The column was washed with water. Elution was then conducted with a 50% (V/V) methanolic water to afford the above-titled compound (Compound 6; 270 mg) as a white powdery product (yield 73%).

$[\alpha]_D^{22}$+89° (c 0.59, $H_2O$) Elemental Analysis for $C_{19}H_{28}N_4O_4 \cdot 0.5H_2SO_4 \cdot H_2O$: Calcd.: C; 51.45, H; 7.05, N; 12.63, S; 3.61 (%) Found: C; 51.23, H; 6.84, N; 13.05, S; 3.76 (%) $^1$H NMR δ ppm (300 MHz, $D_2O$) 1.28(3H,t,J=7.2 Hz), 1.42(4H,m), 2.92(2H,m), 3.10(5H,m), 3.28(1H,d,J=3.3 Hz), 4.27(2H,q,J=7.2 Hz), 4.53(1H,t,J=7.9 Hz), 7.35(5H,m)

WORKING EXAMPLE 7

N-[N-[(2S,3S)-3-carboxyaziridine-2-carbonyl]-L-phenylalanyl]-1,4-diaminobutane In substantially the same manner as Working Example 4, Compound 6 (220 mg) was subjected to alkali hydrolysis to give the above-titled compound (Compound 7; 162 mg) as a white powdery product (yield 88%)

$[\alpha]_D^{22}$+79° (c 0.59, $H_2O$) Elemental Analysis for $C_{17}H_{24}N_4O_4 \cdot H_2O$: Calcd.: C; 55.73, H; 7.15, N; 15.29 (%) Found: C; 55.62, H; 7.25, N; 15.32 (%) $^1$H NMR δ ppm (300 MHz, $D_2O$) 1.47(4H,m), 2.39(1H, br s), 2.74(1H, br s), 2.95(2H,m), 3.11(4H,m), 4.50(1H,t,J=7.7 Hz), 7.36(5H,m)

WORKING EXAMPLE 8

N-[N-[(2S,3S)-N-Z-3-Ethoxycarbonylaziridine-2-carbonyl]-L-phenylalanyl]morpholine In substantially the same manner as Working Example 2, morpholine (1.64 ml, manufactured by Tokyo Kasei) was condensed with Boc-L-phenylalanine (5.00 g) to give Boc-L-phenylalanylmorpholine (6.00 g) as a white powdery product (yield 95%). Taking a portion (2.00 g) of this product, the Boc group was deprotected with TFA, followed by concentration to dryness. The concentrate was dissolved in water, and the solution was allowed to pass through IRA-402 (Cl type, 250 ml, manufactured by Amberlite Inc.), and the solution was concentrated and lyophilized to give L-phenylalanylmorpholine hydrochloride (1.68 g) as a white powdery product (yield: quantitative). A portion (923 mg) of this product was dissolved in dichloromethane (23 ml). To the solution were added, under ice-cooling, (2S,3S)-ethyl hydrogen N-Z-aziridine-2,3-dicarboxylate produced in Working Example 1 (Compound 1, 1.00 g), HOBT (507 mg), WSC (719 mg) and triethylamine (1.02 ml). The mixture was stirred for 14 hours at room temperature. The reaction mixture was concentrated, to which was added ethyl acetate. The mixture was washed with a 10% aqueous solution of citric acid, water, a saturated aqueous solution of sodium hydrogen carbonate, a 2% aqueous solution of sodium hydrogen carbonate, water and a saturated aqueous saline solution, respectively, followed by drying over anhydrous sodium sulfate, which was concentrated. The concentrate was subjected to a silica gel column chromatography (100 ml). The column was subjected to elution with solutions prepared by adding ethyl acetate to hexane in sequence. The eluate with 60% to 70% (v/v) ethyl acetate was concentrated to give the above-titled compound (Compound 8; 940 mg) as a white powdery product (yield 54%).

$[\alpha]_D^{25}$+17° (c 0.55, $CHCl_3$) Elemental Analysis for $C_{27}H_{31}N_3O_7 \cdot 0.5H_2O$: Calcd.: C; 62.54, H; 6.22, N; 8.10 (%) Found: C; 62.56, H; 6.16, N; 7.95 (%) $^1$H NMR δ ppm (300 MHz, $CDCl_3$) 1.25(3H,t,J=7.2 Hz), 2.92(4H,m), 3.16(1H,d,J=2.4 Hz), 3.26(1H,m), 3.40(1H,d,J=2.5 Hz), 3.45(3H,m), 3.59(2H,m), 4.16(2H,m), 5.08(1H,dt,J=8.4,6.1 Hz), 5.10(1H,d,J=11.9 Hz), 5.20(1H,d,J=12.0 Hz), 7.16(2H,m), 7.27(4H,m), 7.35(5H,m)

WORKING EXAMPLE 9

N-[N-[(2S,3S)-3-Ethoxycarbonylaziridine-2-carbonyl]-L-phenylalanyl]morpholine In substantially the same manner as Working Example 3, Compound 8 (840 mg) was subjected to catalytic reduction to deprotect the Z group, then the pH was adjusted to 4.0, followed by extraction with ethyl acetate (30 ml×3). The ethyl acetate layer was washed with a saturated aqueous saline solution, which was dried over anhydrous sodium sulfate, followed by concentration to dryness to afford the above-titled compound (Compound 9; 520 mg) as a white powdery product (yield 84%).

$[\alpha]_D^{25}$+58° (c 0.55, $CHCl_3$) Elemental Analysis for $C_{19}H_{23}N_3O_5$: Calcd.: C; 60.79, H; 6.71, N; 11.19 (%) Found: C; 60.51, H; 6.85, N; 10.99 (%) $^1$H NMR δ ppm (300 MHz, $CDCl_3$) 1.31(3H,t,J=7.1 Hz), 2.47(1H,dd,J=2.1,7.8 Hz), 2.80(1H,dd,J=2.2,8.8 Hz), 2.97(4H,m), 3.33(1H,m), 3.46(2H,m), 3.57(3H,m), 4.23(2H,q,J=7.1 Hz), 5.08(1H,m), 7.18(2H,m), 7.29(3H,m)

WORKING EXAMPLE 10

N-[N-[(2S,3S)-3-Carboxylaziridine-2-carbonyl]-L-phenylalanyl]morpholine sodium salt In substantially the same manner as Working Example 4, Compound 9 (100 mg) was subjected to alkali hydrolysis to produce the above-titled compound (Compound 10; 92 mg) as a white powdery product (yield 94%).

$[\alpha]_D^{26}$+92° (c 0.56, $H_2O$) Elemental Analysis for $C_{17}H_{20}N_3O_5Na \cdot H_2O$: Calcd.: C; 52.71, H; 5.72, N; 10.85, Na; 5.93 (%) Found: C; 52.51, H; 5.92, N; 10.95, Na; 6.15 (%) $^1$H NMR δ ppm (300 MHz, $D_2O$) 2.43(1H,br s), 2.75(1H,br s), 2.91(1H,m), 3.02(1H,m), 3.08(1H,m), 3.23(1H,m), 3.42(3H,m), 3.55(2H,m), 3.65(1H,m), 5.03(1H,dd, J=6.9,8.6 Hz), 7.27(2H,m), 7.37(3H,m)

WORKING EXAMPLE 11

N-[N-[(2S,3S)-N-Z-3-Ethoxycarbonylaziridine-2-carbonyl]-L-leuycyl]isopentylamine In substantially the same manner as working Example 2, isopentylamine (2.33 ml) was condensed with Boc-L-leucine monohydrate (5.00 g, manufactured by Peptide Institute, Inc.) to give N-(Boc-L-leucyl)isopentylamine (5.73 g) as a white powdery product (yield 95%). The Boc group was deprotected with TFA, and 667 mg of thus-produced compound was condensed, in substantially the same manner as Working Example 2, with (2S,3S)-ethyl hydrogen N-Z-aziridine-2,3-dicarboxylate (Compound 1, 1.00 g) to afford the above-titled compound (Compound 11; 920 mg) as a colorless oily product (yield 58%).

$[\alpha]_D^{26}$ −16° (c 1.01, $CHCl_3$) Elemental Analysis for $C_{25}H_{37}N_3O_6$: Calcd.: C; 63.14, H; 7.84, N; 8.84 (%) Found: C; 62.99, H; 7.70, N; 8.94 (%) $^1H$ NMR δ ppm (300 MHz, $CDCl_3$) 0.90(12H,d,J=6.6 Hz), 1.25(3H,t,J=7.2 Hz), 1.38 (2H,m), 1.56(4H,m), 3.21(1H,d,J=2.5 Hz), 3.25(2H,m), 3.44 (1H,d,J=2.5 Hz), 4.17(2H,m), 4.36(1H,dt,J=6.0,8.4 Hz), 5.08(1H,d,J=12.1 Hz), 5.22(1H,d,J=12.0 Hz), 6.12(1H,t,J=5.6 Hz), 6.90(1H,d,J=8.6 Hz), 7.35(5H,m)

WORKING EXAMPLE 12

N-[N-[(2S,3S)-3-Ethoxycarbonylaziridine-2-carbonyl]-L-leucyl]isopentylamine

In substantially the same manner as Working Example 3, Compound 11 (800 mg) was subjected to catalytic reduction to deprotect the Z group, and the resultant compound was concentrated to give precipitate. The precipitate was collected by filtration, washed with water and dried to afford the above-titled compound (Compound 12; 458 mg) as a white powdery product (yield 80%).

$[\alpha]_D^{25}$ +6.1° (c 0.61, $CHCl_3$) Elemental Analysis for $C_{17}H_{31}N_3O_4$·0.1 $H_2O$: Calcd.: C; 59.48, H; 9.16, N; 12.24 (%) Found: C; 59.41, H; 9.08, N; 12.39 (%) $^1H$ NMR δ ppm (300 MHz, $CDCl_3$) 0.90(3H,d,J=6.5 Hz), 0.91(6H,d,J=6.6 Hz), 0.92(3H,d,J=6.5 Hz), 1.32(3H,t,J=7.1 Hz), 1.39(2H,m), 1.52(1H,m), 1.62(2H,m), 1.80(2H,m), 2.56(1H,dd,J=2.3,7.7 Hz), 2.85(1H,dd,J=2.3,9.0 Hz), 3.25(2H,m), 4.25(2H,m), 4.31(1H,dt,J=8.7,6.0 Hz), 6.13(1H,t,J=4.2 Hz), 6.80(1H,d,J=8.7 Hz)

WORKING EXAMPLE 13

N-[N-[(2S,3S)-3-carboxyaziridine-2-carbonyl]-L-leucyl]isopentylamine sodium salt In substantially the same manner as Working Example 4, Compound 12 (100 mg) was subjected to alkali hydrolysis to produce the above-titled compound (Compound 13; 87 mg) as a white powdery product (yield 89%).

$[\alpha]_D^{26}$ +38° (c 0.55, $H_2O$) Elemental Analysis for $C_{15}H_{26}N_3O_4Na \cdot H_2O$: Calcd.: C; 50.98, H; 7.99, N; 11.89 (%) Found: C; 51.02, H; 8.18, N; 11.68 (%) $^1H$ NMR δ ppm (300 MHz, $D_2O$) 0.86(3H,d,J=6.6 Hz), 0.87(3H,d,J=6.6 Hz), 0.88(3H,d,J=5.8 Hz), 0.92(3H,d,J=6.0 Hz), 1.37(2H,m), 1.59(4H,m) r 2.52(1H,d,J=2.4 Hz), 2.76(1H,d,J=2.4 Hz), 3.15(1H,dt,J=13.6,7.0 Hz), 3.26(1H,dt,J=13.6,7.0 Hz), 4.24 (1H,dd,J=5.5,9.1 Hz)

WORKING EXAMPLE 14

N-Z—N'-[N-[(2S,3S)-N-Z-3-Ethoxycarbonylaziridine-2-carbonyl]-L-leucyl]-1,4-diaminobutane In substantially the same manner as Working Example 2, N-Z-1,4-diaminobutane (3–33 g) was condensed with Boc-L-leucine monohydrate (4.11 g) to give N-Z—N'-(Boc-L-leucyl)-1,4-diaminobutane (5.40 g) as a white powdery product (yield 83%). The Boc group was deprotected with TFA, and 3.80 g of the resultant compound was subjected to condensation, in substantially the same manner as Working Example 2, with (2S,3S)-ethyl hydrogen N-Z-aziridine-2,3-dicarboxylate (Compound 1, 3.65 g) to give the above-titled compound (Compound 14; 3.90 g) as a white powdery product (yield 57%).

$[\alpha]_D^{26}$ −10° (c 0.56, $CHCl_3$) Elemental Analysis for $C_{32}H_{42}N_4O_8$: Calcd.: C; 62.94, H; 6.93, N; 9.17 (%) Found: C; 62.65, H; 6.77, N; 9.24 (%) $^1H$ NMR δ ppm (300 MHz, $CDCl_3$) 0.88(3H,d,J=6.0 Hz), 0.90(3H,d,J=6.0 Hz), 1.24 (3H,t,J=7.2 Hz), 1.52(5H,m), 1.62(2H,m), 3.19(1H,d,J=2.5 Hz), 3.22(4H,m) r 3.42(1H,d,J=2.5 Hz), 4.16(2H,m), 4.36 (1H,m), 4.95(1H,t,J=4.8 Hz), 5.07(1H,d=12.1 Hz), 5.10(2H, s), 5.20(1H,d,J=12.0 Hz), 6.30(1H,br s), 6.72(1H,d,J=8.4 Hz), 7.35(10H,m)

WORKING EXAMPLE 15

N-[N-[(2S,3S)-3-Ethoxycarbonylaziridine-2-carbonyl]-L-leuycyl]-1,4-diaminobutane ½ sulfate In substantially the same manner as Working Example 3, Compound 14 (2.44 g) was subjected to catalytic reduction to deprotect the Z group. The resultant compound was subjected to a Diaion HP-20 (100 ml) column chromatography. The column was washed with water, then elution was conducted by the use of 50% (v/v) mathanolic water. The eluate was concentrated, and the concentrate was lyophilized to give the above-titled compound (Compound 15; 1.24 g) as a white powdery product (yield 79%).

$[\alpha]_D^{26}$ +65° (c 0.55, $H_2O$) Elemental Analysis for $C_{16}H_{30}N_4O_4 \cdot 0.5H_2SO_4 \cdot 0.5H_2O$: Calcd.: C; 47.99, H; 8.05, N; 13.99, S; 4.00 (%) Found : C; 47.85, H; 8.09, N; 14.17, S; 4.18 (%) $^1H$ NMR δ ppm (300 MHz, $D_2O$) 0.88(3H,d, J=6.1 Hz), 0.93(3H,d,J=6.0 Hz), 1.27(3H,t,J=7.2 Hz), 1.61 (7H,m), 2.83(1H,d,J=2.3 Hz), 2.96(1H,d,J=2.3 Hz), 3.00 (2H,m), 3.22(2H,m), 4.23(2H,q,J=7.2 Hz), 4.27(1H,m)

WORKING EXAMPLE 16

N-[N-[(2S,3S)-3-carboxyaziridine-2-carbonyl]-L-leucyl]-1,4-diaminobutane

In substantially the same manner as Working Example 4, Compound 15 (200 mg) was subjected to alkali hydrolysis to give the above-titled compound (Compound 16; 159 mg) as a white powdery product (yield 99%).

$[\alpha]_D^{26}$ +51° (c 0.56, $H_2O$) Elemental Analysis for $C_{14}H_{26}N_4O_4 \cdot 0.5H_2O$: Calcd.: C; 52.00, H; 8.42, N; 17.32 (%) Found: C; 52.01, H; 8.62, N; 17.37 (%) $^1H$ NMR δ ppm (300 MHz, $D_2O$) 0.88(3H,d,J=6.1 Hz), 0.93(3H,d,J=6.1 Hz), 1.60(7H,m), 2.51(1H,br s), 2.78(1H,br s), 2.99(2H,m), 3.22 (2H,m), 4.23(1H,dd,J=5.2,9.4 Hz)

WORKING EXAMPLE 17

N-[N-[(2S,3S)-N-Z-3-Ethoxycarbonylaziridine-2-carbonyl]-L-leucyl]morpholine

In substantially the same manner as Working Example 2, morpholine (1.76 ml) was condensed with Boc-L-leucine monohydrate (5.00 g) to give Boc-L-leucylmorpholine (5.76 g) as a colorless oily product (yield 95%). A portion (2.00 g) of this product was taken, and the Boc group was deprotected by using TFA. The resultant compound was treated in substantially the same manner as Working Example 8 to afford L-leucylmorpholine hydrochloride (1.52 g) as a white powdery product (yield 96%). A portion (807 mg) of this product was condensed, in substantially the same manner as Working Example 8, with (2S,3S)-ethyl hydrogen N-Z-aziridine-2,3-dicarboxylate (Compound 1, 100 g) to afford the above-titled compound (Compound 17; 1.06 g) as a white powdery product (yield 65%).

$[\alpha]_D^{25}$+16° (c 0.54, CHCl$_3$) Elemental Analysis for C$_{24}$H$_{33}$N$_3$O$_7$: Calcd.: C; 60.62, H; 6.99, N; 8.84 (%) Found: C; 60.38, H; 7.07, N; 8.97 (%) $^1$H NMR δ ppm (300 MHz, CDCl$_3$) 0.88(3H,d,J=6.4 Hz), 0.94(3H,d,J=6.4 Hz), 1.25 (3H,t,J=7.2 Hz), 1.40(1H,m), 1.52(2H,m), 3.24(1H,d,J=2.4 Hz), 3.43(1H,d,J=2.4 Hz), 3.54(3H,m), 3.69(5H,m), 4.17 (2H,m), 4.96(1H,dt,J=4.2,9.0 Hz), 5.06(1H,d,J=12.1 Hz), 5.23(1H,d,J=12.1 Hz), 7.17(2H,d,J=8.7 Hz), 7.35(5H,m)

WORKING EXAMPLE 18

N-[N-[(2S,3S)-3-Ethoxycarbonylaziridine-2-carbonyl]-L-leucyl]morpholine

In substantially the same manner as Working Example 3, Compound 17 (950 mg) was subjected to catalytic reduction to deprotect the Z group, which was treated in substantially the same manner as Working Example 9 to afford the above-titled compound (Compound 18; 540 mg) as a colorless oily product (yield 79%).

$[\alpha]_D^{26}$+53° (c 0.75, CHCl$_3$) Elemental Analysis for C$_{16}$H$_{27}$N$_3$O$_5$.0.25H$_2$O: Calcd.: C; 55.56, H; 8.01, N; 12.15 (%) Found: C; 55.44, H; 7.98, N; 11.68 (%) $^1$H NMR δ ppm (300 MHz, CDCl$_3$) 0.91(3H,d,J=6.4 Hz), 0.96(3H,d,J=6.4 Hz), 1.32(3H,t,J=7.2 Hz), 1.43(1H,m), 1.53(2H,m), 1.81(1H,t,J=8.4 Hz), 2.59(1H,dd,J=2.2,7.8 Hz), 2.84(1H,dd,J=2.1,9.2 Hz), 3.55(3H,m), 3.69(5H,m), 4.24(2H,m), 4.92(1H,dt,J=4.3,9.2 Hz), 7.11(1H,d,J=8.8 Hz)

WORKING EXAMPLE 19

N-[N-[(2S,3S)-3-Carboxyaziridine-2-carbonyl]-L-leucyl]morpholine sodium salt

In substantially the same manner as Working Example 4, Compound 18 (100 mg) was subjected to alkali hydrolysis to give the above-titled compound (Compound 19; 85 mg) as a white powdery product (yield 87%).

$[\alpha]_D^{26}$+55° (c 0.56, H$_2$O) Elemental Analysis for C$_{14}$H$_{22}$N$_3$O$_5$Na.0.5 H$_2$O: Calcd.: C; 48.83, H; 6.73, N; 12.20, Na; 6.68 (%) Found: C; 48.94, H; 6.88, N; 12.37, Na; 6.71 (%) $^1$H NMR δ ppm (300 MHz, D$_2$O) 0.99(3H,d,J=5.9 Hz), 1.02(3H,d,J=6.0 Hz), 1.58(1H,m), 1.73(2H,m), 2.58 (1H,br s), 2.88(1H,br s), 3.64(1H,m), 3.81(7H,m), 4.90(1H, dd,J=4.1,9.5 Hz)

WORKING EXAMPLE 20

N-[N-[(2S,3S)-N-Z-3-Ethoxycarbonylaziridine-2-carbonyl]-L-leucyl]-3-methoxypropylamine In substantially the same manner as Working Example 2, 3-methoxypropylamine (6.1 ml, Wako Pure Chemical Industries, Ltd.) was condensed with Boc-L-leucine monohydrate (5.00 g, manufactured by Peptide Institute, Inc.) to afford N-(Boc-L-leucyl)methoxypropylamine (17.5 g) as a colorless waxy product (yield 89%). The Boc group was deprotected by using TFA, and 1.21 g of the resultant compound was condensed, in substantially the same manner as Working Example 2, with (2S,3S)-ethyl hydrogen N-Z-aziridine-2,3-dicarboxylate (Compound 1, 1.93 g) to afford the above-titled compound (Compound 20; 2.55 g) as a white crystalline product (yield 89%).

Elemental Analysis for C$_{24}$H$_{35}$N$_3$O$_7$: Calcd.: C; 60.36, H; 7.38, N; 8.80 (%) Found: C; 60.24, H; 7.10, N; 8.95 (%) $^1$H NMR δ ppm (200 MHz, CDCl$_3$) 0.91(3H,d), 0.92(3H, d), 1.25(3H,t,J=7.2Hz), 1.53(2H,m), 1.68(1H,m), 1.77(2H, m), 3.20(1H,d,J=2.5Hz), 3.34(3H,s), 3.37(2H,m), 3.43(1H, d,J=2.5Hz), 3.48(2H,t), 4.17(2H,m), 4.37(1H,m), 5.08(1H, d), 5.22(1H,d), 6.50(1H,t), 6.77(1H,d), 7.35(5H,m)

Working Example 21

N-[N-[(2S,3S)-3-Ethoxycarbonylaziridine-2-carbonyl]-L-leucyl]-3-methoxypropylamine In substantially the same manner as Working Example 3, Compound 20 (2.2 g) was subjected catalytic reduction to deprotect the Z group, which was concentrated to dryness. The concentrate was recrystallized, when hot, from a small quantity of water to afford the above-titled compound (Compound 21; 1.31 g) as a white cubic crystalline product (yield 83%).

Elemental Analysis for C$_{16}$H$_{29}$N$_3$O$_5$: Calcd.: C; 55.96, H; 8.51, N; 12.24 (%) Found: C; 55.88, H; 8.35, N; 12.49 (%) $^1$H NMR δ ppm (200 MHz, CDCl$_3$) 0.89(3H,d), 0.92(3H, d), 1.31(3H,t,J=7.2Hz), 1.53(2H,m), 1.68(1H,m), 1.80(2H, m), 2.55(1H,d), 2.86(1H,d), 3.35(3H,s), 3.37(2H,m), 3.47 (2H,m), 3.47(2H,t,J=5.7Hz), 4.25(2H,q,J=7.2Hz), 4.34(1H, m), 6.54(1H,br s), 6.82(1H,d)

Working Example 22

N-[N-[(2S,3S)-3-carboxyaziridine-2-carbonyl]-L-leucyl]-3-methoxypropylamine Sodium Salt In substantially the same manner as Working Example 4, Compound 21 (700 mg) was subjected to alkali hydrolysis to afford the above-titled compound (Compound 22; 590 mg) as a white powdery product (yield 85%).

Elemental Analysis for C$_{14}$H$_{24}$N$_3$O$_5$Na.0.5H$_2$O: Calcd.: C; 48.55, H; 7.28, N; 12.13 (%) Found: C; 48.79, H; 7.46, N; 12.21 (%) $^1$H NMR δ ppm (200 MHz, D$_2$O) 0.88(3H,d,J=5.8Hz), 0.92(3H,d,J=5.7Hz), 1.60(2H,m), 1.66(1H,m), 1.75(2H,m), 2.53(1H,d), 2.77(1H,d,J=2.2Hz), 3.24(2H,m), 3.32(3H,s), 3.46(2H,t,J=6.3Hz), 4.26(1H,m)

Working Example 23

N-[N-[(2S,3S)-N-Z-3-Ethoxycarbonylaziridine-2-carbonyl]-L-leucyl]piperidine

In substantially the same manner as Working Example 2, piperidine (0.86 g, manufactured by Wako Pure Chemical Industries, Ltd.).was condensed with Boc-L-leucine (2.74 g, manufactured by Peptide Institute, Inc.) to give N-(Boc-L-leucyl)piperidine (3.34 g) as white needles (yield 80%). The Boc group of the product was deprotected by using TFA, and 1.20 g of thus-deprotected compound was condensed, in substantially the same manner as Working Example 2, with (2S,3S)-ethyl hydrogen N-Z-aziridine-2,3-dicarboxylate (Compound 1, 1.93 g) to give the above-titled compound (Compound 23; 1.10 g) as a pale yellow oily product (yield 39%).

Elemental Analysis for C$_{25}$H$_{35}$N$_3$O$_6$: Calcd.: C; 63.40, H; 7.45, N; 8.87 (%) Found: C; 63.16, H; 7.76, N; 8.99 (%) $^1$H NMR δ ppm (200 MHz, CDCl$_3$) 0.85(3H,d,J=6.4Hz), 0.95(3H,d,J=6.3Hz), 1.25(3H,t,J=7.2Hz), 1.32–1.72(9H,m), 3.25(1H,d,J=2.5Hz), 3.40(1H,d,J=2.5Hz), 3.42(2H,m), 3.55 (2H,m), 4.16(2H,m), 4.98(1H,m), 5.05(1H,d), 5.24(1H,d), 7.18(1H,d), 7.35(5H,m)

Working Example 24

N-[N-[(2S,3S)-3-Ethoxycarbonylaziridine-2-carbonyl)-L-leuycyl]piperidine

In substantially the same manner as Working Example 3, Compound 23 (2.78 g) was subjected to catalytic reduction to deprotect the Z group, which was subjected to a silica gel column chromatography (200 ml). Elution was conducted with eluents prepared by adding methanol to chloroform in sequence. From the fraction eluted with 2% (v/v) methanol-containing-chloroform, the above-titled compound (Compound 24; 1.26 g) was obtained as white crystals (yield 45%)

Elemental Analysis for $C_{17}H_{29}N_3O_4 \cdot 2H_2O$: Calcd.: C; 54.38, H; 8.85, N; 11.19 (%) Found: C; 54.29, H; 7.83, N; 11.03 (%)

$^1$H NMR δ ppm (200 MHz, CDCl$_3$) 0.91(3H,d,J=6.3Hz), 0.98(3H,d,J=6.2Hz), 1.31(3H,t,J=7.2Hz), 1.37–1.90(9H,m), 2.63(1H,br s), 2.81(1H,br s), 3.45(2H,m), 3.55(2H,m), 4.23 (2H,q,J=7.3Hz), 4.98(1H,m), 7.15(1H,d)

Working Example 25

N-[N-[(2S,3S)-3-Carboxyaziridine-2-carbonyl]-L-leucyl]piperidine Sodium Salt In substantially the same manner as Working Example 4, Compound 24 (760 mg) was subjected to alkali hydrolysis to afford the above-titled compound (Compound 25; 162 mg) as a white powdery product (yield 73%).

Elemental Analysis for $C_{15}H_{24}N_3O_4Na \cdot 0.5H_2O$: Calcd.: C; 52.62, H; 7.36, N; 12.26 (%) Found: C; 52.77, H; 7.67, N; 12.31 (%)

$^1$H NMR δ ppm (200 MHz, D$_2$O) 0.92(6H,d,J=5.8Hz), 1.40–1.75(9H,m), 2.51(1H,d), 2.77(1H,d,J=2.7Hz), 3.37–3.62(4H,m), 4.88(1H,m)

Working Example 26

N-[(2S,3S)-3-Ethoxycarbonylaziridine-2-carbonyl]-L-phenylalanyl]-3-methoxypropylamine L-Phenylalanine benzylester tosylate (80.5 g, manufactured by Peptide Institute, Inc.) was dissolved in dichloromethane (2200 ml). To the solution was added, under ice-cooling, triethylamine (20 g). To the mixture was added (2S,3S)-ethyl hydrogen N-Z-aziridine-2,3-dicarboxylate (Compound 1; 61.3 g) produced in Working Example 1, HOBT (26.7 g), WSC (37.9 g), which was stirred for 3 hours at room temperature. The reaction mixture was concentrated, to which was added ethyl acetate (1500 ml). The mixture was washed with a 10% aqueous solution of citric acid, a 3% aqueous solution of sodium hydrogen carbonate and a saturated aqueous saline solution, successively. The organic layer was dried over anhydrous sodium sulfate, followed by concentration to dryness. The concentrate was pulverized by adding n-hexane to give N-[(2S,3S)-N-Z-3-ethoxycarbonylaziridine-2-carbonyl]-L-phenylalanine benzylester (compound 26a; 98 g) (yield 98%).

Elemental Analysis for $C_{30}H_{30}N_2O_7$: Calcd.: C; 67.91, H; 5.69, N; 5.28 (%) Found: C; 68.13, H; 5.54, N; 5.36 (%)

$^1$H NMR δ ppm (200 MHz, CDCl$_3$) 1.24(3H,t,J=7.2Hz), 2.98(1H,d,J=2.4Hz), 3.08(2H,m), 3.34(1H,d,J=2.4Hz), 4.15 (2H,m), 4.87(1H,m), 5.09(1H,d), 5.16(2H,s), 5.20(1H,d), 6.55(1H,d), 6.93(2H,m), 7.20(3H,m), 7.34(10H,m)

The whole amount (98 g) of the above product was dissolved in a mixture of ethanol (640 ml) and ethyl acetate (160 ml). To the solution was added Pd-C (10% (w/w), 4.5 g), and the mixture was stirred for 3 hours at room temperature under hydrogen gas atmosphere. The catalyst was filtered off, and the filtrate was concentrated to dryness under reduced pressure to give white amorphous crystals. The crystalline product was recrystallized, when hot, from tetrahydrofuran to afford N-[(2S,3S)-3-ethoxycarbonylaziridine-2-carbonyl]-L-phenylalanine (compound 26b; 45.3 g) as white fine needles (yield 80%).

Elemental Analysis for $C_{15}H_{18}N_2O_5$: Calcd.: C; 58.82, H; 5.92, N; 9.15 (%) Found: C; 58.82, H; 5.77, N; 9.36 (%)

$^1$H NMR δ ppm (200 MHz, CDCl$_3$) 1.25(3H,t,J=7.3Hz), 2.28(1H,m), 2.80(1H,m), 3.17(2H,m), 3.73(2H,q,J=7.0Hz), 4.22(1H,m), 6.74(1H,m), 7.13(2H,m), 7.28(3H,m)

Further, in dichloromethane (40 ml) was dissolved the N-[(2S,3S)-3-ethoxycarbonylaziridine-2-carbonyl]-L-phenylalanine (1.22 g). To the solution were added, under ice-cooling, 3-methoxypropylamine (0.39 g, manufactured by Wako Pure Chemical Industries, Ltd.), HOBT (0.59 g) and WSC (0.84 g), then the mixture was stirred for 16 hours at room temperature. The reaction mixture was concentrated, to which was added ethyl acetate (150 ml). The mixture was washed with a 10% aqueous solution of citric acid, a 3% aqueous solution of sodium hydrogen carbonate and a saturated aqueous saline solution, successively. The organic layer was dried over anhydrous sodium sulfate, which was concentrated and, then subjected to a silica gel column chromatography (200 ml). Elution was conducted by using eluents prepared by adding methanol to chloroform in sequence. From the fraction of chloroform containing 2% (v/v) methanol, the above-titled compound (Compound 26; 1.18 g) was obtained as white crystals (yield 78%).

Elemental Analysis for $C_{19}H_{27}N_3O_5$: Calcd.: C; 60.46, H; 7.21, N; 11.13 (%) Found: C; 60.21, H; 7.02, N; 11.17 (%)

$^1$H NMR δ ppm (200 MHz, CDCl$_3$) 1.30(3H,t,J=7.2Hz), 1.60(2H,m), 2.20(1H,dd,J=2.2,7.7Hz), 2.79(1H,dd,J=2.1, 9.0Hz), 3.02(2H,m), 3.26(3H,s), 3.32(4H,m), 4.20(2H,q,J= 7.2Hz), 4.50(1H,m), 6.27(1H,br s), 6.90(1H,d), 7.18(2H,m), 7.32(3H,m)

Working Example 27

N-[N-[(2S,3S)-3-Carboxyaziridine-2-carbonyl]-L-phenylalanyl]-3-methoxypropylamine Sodium Salt In substantially the same manner as Working Example 4, Compound 26 (670 mg) was subjected to alkali hydrolysis to produce the above-titled compound (Compound 27; 510 mg) as a white powdery product (yield 81%).

Elemental Analysis for $C_{17}H_{22}N_3O_5Na \cdot 0.5H_2O$: Calcd.: C; 53.68, H; 6.09, N; 11.05 (%) Found: C; 53.49, H; 6.36, N; 11.03 (%)

$^1$H NMR δ ppm (200 MHz, D$_2$O) 1.58(2H,m), 2.40(1H,br s), 2.71(1H,d,J=2.6Hz), 3.05(2H,m), 3.18(2H,m), 3.23(2H, m), 3.28(3H,s), 4.49(1H,m), 7.26(2H,m), 7.37(3H,m)

Working Example 28

N-[N-[(2S,3S)-3-Ethoxycarbonylaziridine-2-carbonyl]-L-phenylalanyl]hexylamine In substantially the same manner as Working Example 26, N-[(2S,3S)-3-ethoxycarbonylaziridine-2-carbonyl]-L-phenylalanine (1.22 g) was condensed with hexylamine (0.44 g, manufactured by Wako Pure Chemical Industries, Ltd.) to give the above-titled compound (Compound 28; 0.84 g) as white crystals (yield 54%).

Elemental Analysis for $C_{21}H_{31}N_3O_4$: Calcd.: C; 64.76, H; 8.02, N; 10.79 (%) Found: C; 64.61, H; 8.05, N; 10.85 (%)

$^1$H NMR δ ppm (200 MHz, $CDCl_3$) 0.87(3H,t,J=6.6Hz), 1.22(8H,m), 1.30(3H,t,J=7.2Hz), 1.72(1H,m), 2.20(1H,dd), 2.78(1H,dd,J=2.2,9.0Hz), 3.01(2H,m), 3.15(2H,m), 4.22 (2H,q,J=7.2Hz), 4.48(1H,m), 5.72(1H,t), 6.90(1H,d), 7.18 (2H,m), 7.30(3H,m)

Working Example 29

N-[N-[(2S,3S)-3-carboxyaziridine-2-carbonyl]-L-phenylalanyl]hexylamine Sodium Salt In substantially the same manner as Working Example 4, Compound 28 (440 mg) was subjected to alkali hydrolysis to give the above-titled compound (Compound 29; 330 mg) as a white powdery product (yield 73%).

Elemental Analysis for $C_{19}H_{26}N_3O_4Na \cdot H_2O$: Calcd.: C; 56.85, H; 7.03, N; 10.47 (%) Found: C; 57.50, H; 7.04, N; 10.46 (%)

$^1$H NMR δ ppm (200 MHz, $D_2O$) 0.84(3H,t,J=6.7Hz), 1.20(8H,m), 2.42(1H,br s), 2.71(1H,d,J=2.6Hz), 3.04(4H, m), 4.49(1H,t,J=7.7Hz), 7.25(2H,m), 7.34(3H,m)

Working Example 30

N-[N-[(2S,3S)-3-Ethoxycarbonylaziridine-2-carbonyl]-L-phenylalanyl]allylamine

In substantially the same manner as Working Example 26, N-[(2S,3S)-3-ethoxycarbonylaziridine-2-carbonyl]-L-phenylalanine (1.22 g) was condensed with allylamine (0.25 g, manufactured by Wako Pure Chemical Industries, Ltd.) to give the above-titled compound (Compound 30; 1.25 g) as white crystals (yield 91%).

Elemental Analysis for $C_{18}H_{23}N_3O_4$: Calcd.: C; 62.59, H; 6.71, N; 12.17 (%) Found: C; 62.12, H; 6.48, N; 12.13 (%)

$^1$H NMR δ ppm (200 MHz, $CDCl_3$) 1.29(3H,t,J=7.2Hz), 1.73(1H,m), 2.17(1H,dd,J=2.5,7.9Hz), 2.77(1H,dd), 3.04 (2H,m), 3.81(2H,m), 4.21(2H,q,J=7.2Hz), 4.52(1H,m), 5.08 (2H,m), 5.07(1H,m), 5.95(1H,t), 6.98(1H,d), 7.17(2H,m), 7.28(3H,m)

Working Example 31

N-[N-[(2S,3S)-3-carboxyaziridine-2-carbonyl]-L-phenylalanyl]allylamine Sodium Salt In substantially the same manner as Working Example 4, Compound 30 (570 mg) was subjected to alkali hydrolysis to give the above-titled compound (Compound 31; 480 mg) as a white powdery product (yield 79%)

Elemental Analysis for $C_{16}H_{18}N_2O_4Na \cdot H_2O$: Calcd.: C; 53.78, H; 5.64, N; 11.76 (%) Found: C; 53.27, H; 5.99, N; 11.47 (%)

$^1$H NMR δ ppm (200 MHz, $D_2O$) 2.33(1H,br s), 2.70(1H, d), 3.09(2H,m), 3.71(2H,d,J=5.0Hz), 4.56(1H,t,J=7.7Hz), 5.00(1H,dd,J=1.5,17.2Hz), 5.07(1H,dd,J=1.5,10.4Hz), 5.70 (1H,m), 7.27(2H,m), 7.35(3H,m)

Working Example 32

N-[N-[(2S,3S)-3-ethoxycarbonylaziridine-2-carbonyl-L-phenylalanyl]-3-butoxypropylamine In substantially the same manner as Working Example 26, N-[(2S,3S)-3-ethoxycarbonylaziridine-2-carbonyl]-L-phenylalanine (1.22 g) was condensed with 3-butoxypropylamine (0.58 g, manufactured by Wako Pure Chemical Industries, Ltd.) to give the above-titled compound (Compound 32; 1.20 g) as white crystals (yield 72%).

Elemental Analysis for $C_{22}H_{33}N_3O_5$: Calcd.: C; 62.98, H; 7.92, N; 10.01 (%) Found: C; 62.83, H; 7.73, N;10.18 (%)

$^1$H NMR δ ppm (200 MHz, $CDCl_3$) 0.93(3H,t,J=7.2Hz), 1.30(3H,t,J=7.2Hz), 1.33–1.80(7H,m), 2.19(1H,dd), 2.77 (1H,dd), 3.01(1H,m), 3.34(6H,m), 4.21(2H,q,J=7.2Hz), 4.49(1H,m), 6.28(1H,t), 6.90(1H,d), 7.16(2H,m), 7.28(3H, m)

Working Example 33

N-[N-[(2S,3S)-3-carboxyaziridine-2-carbonyl]-L-phenylalanyl]- 3-butoxypropylamine Sodium Salt In substantially the same manner as Working Example 4, Compound 32 (600 mg) was subjected to alkali hydrolysis to give the above-titled compound (Compound 33; 370 mg) as a white powdery product (yield 58%).

Elemental Analysis for $C_{20}H_{28}N_3O_5Na \cdot 2H_2O$: Calcd.: C; 53.44, H; 7.18, N; 9.35 (%) Found: C; 53.52, H; 6.84, N; 9.31 (%)

$^1$H NMR δ ppm (200 MHz, $D_2O$) 0.89(3H,t,J=7.3Hz), 1.32(2H,m), 1.53(4H,m), 2.36(1H,d), 2.73(1H,d,J=2.6Hz), 3.00–3.33(6H,m), 3.46(2H,t,J=6.6Hz), 4.50(1H,t,J=7.7Hz), 7.24(2H,m), 7.36(3H,m)

Working Example 34

N-[N-[(2S,3S)-3-Ethoxycarbonylaziridine-2-carbonyl]-L-phenylalanyl]isobutylamine In substantially the same manner as Working Example 26, N-[(2S,3S)-3-ethoxycarbonylaziridine-2-carbonyl]-L-phenylalanine (1.53 g) was condensed with isobutylamine (0.40 g, manufactured by Wako Pure Chemical Industries, Ltd.) to give the above-titled compound (Compound 34; 1.14 g) as white crystals (yield 55%).

Elemental Analysis for $C_{19}H_{27}N_3O_4$: Calcd.: C; 63.14, H; 7.53, N; 11.63 (%) Found: C; 63.01, H; 7.27, N; 11.53 (%)

$^1$H NMR δ ppm (200 MHz, $CDCl_3$) 0.79(3H,d,J=6.6Hz), 0.86(3H,d,J=6.6Hz), 1.30(3H,t,J=7.2Hz), 1.62(1H,m), 1.72 (1H,m), 2.00(1H,dd), 2.77(1H,dd), 2.88–3.16(4H,m), 4.22 (2H,q,J=7.1Hz), 4.51(1H,m), 5.85(1H,br s), 6.90(1H,d), 7.19(2H,m), 7.29(3H,m)

Working Example 35

N-[N-[(2S,3S)-3-Carboxyaziridine-2-carbonyl]-L-phenylalanyl]isobutylamine Sodium Salt In substantially the same manner as Working Example 4, Compound 34 (580 mg) was subjected to alkali hydrolysis to give the above-titled compound (Compound 35; 380 mg) as a white powdery product (yield 58%)

Elemental Analysis for $C_{17}H_{22}N_3O_4Na \cdot 3H_2O$: Calcd.: C; 49.87, H; 6.89, N; 10.26 (%) Found: C; 49.59, H; 6.27, N; 9.98 (%)

$^1$H NMR δ ppm (200 MHz, $D_2O$) 0.73(3H,d,J=5.9Hz), 0.76(3H,d,J=6.2Hz), 1.62(1H,m), 2.34(1H,d,J=2.6Hz), 2.72 (1H,d), 2.91(2H,m), 3.06(2H,m), 4.53(1H,t,J=7.6Hz), 7.31 (5H,m)

Working Example 36

N-[N-[(2S,3S)-3-Ethoxycarbonylaziridine-2-carbonyl]-L-phenylalanyl]-3-isopropoxypropylamine In substantially the Same manner as Working Example 26, N-[(2S,3S)-3-ethoxycarbonylaziridine-2-carbonyl]-L- phenylalanine (1.22 g) was condensed with 3-isopropoxypropylamine (0.64 g, manufactured by Tokyo Kasei Co., Ltd.) to give the above-titled compound (Compound 36; 1.20 g) as white crystals (yield 74%).

Elemental Analysis for $C_{21}H_{31}N_3O_5$: Calcd.: C; 62.20, H; 7.71, N; 10.36 (%) Found: C; 62.13, H; 7.55, N; 10.54 (%)

$^1$H NMR δ ppm (200 MHz, CDCl$_3$) 1.11(3H,d,J=5.9Hz), 1.12(3H,d,J=6.1Hz), 1.30(3H,t,J=7.2Hz), 1.68(3H,m), 2.18 (1H,dd), 2.77(1H,dd), 3.02(2H,m), 3.25–3.56(5H,m), 4.21 (2H,q,J=7.2Hz), 4.48(1H,m), 6.35(1H,t), 6.89(1H,d), 7.16 (2H,m), 7.28(3H,m)

Working Example 37

N-[N-[(2S,3S)-3-carboxyaziridine-2-carbonyl]-L-phenylalanyl]-3-isopropoxypropylamine Sodium Salt In substantially the same manner as Working Example 4, Compound 36 (710 mg) was subjected to alkali hydrolysis to give the above-titled compound (Compound 37; 490 mg) as a white powdery product (yield 66%)

Elemental Analysis for $C_{19}H_{26}N_3O_5Na.1.5H_2O$: Calcd.: C; 53.51, H; 6.85, N; 9.85 (%) Found: C; 53.32, H; 6.78, N; 9.60 (%)

$^1$H NMR δ ppm (200 MHz, D$_2$O) 1.12(6H,d,J=6.2Hz), 1.56(2H,m), 2.35(1H,br s), 2.71(1H,d), 3.00–3.37(6H,m), 3.60(1H,m), 4.50(1H,m), 7.27(2H,m), 7.35(3H,m)

Working Example 38

N-[N-[(2S,3S)-3-Ethoxycarbonylaziridine-2-carbonyl]-L-phenylalanyl]furfurylamine In substantially the same manner as Working Example 26, N-[(2S,3S)-3-ethoxycarbonylaziridine-2-carbonyl]-L-phenylalanine (1.22 g) was condensed with furfurylamine (0.43 g, manufactured by Wako Pure Chemical Industries, Ltd.) to give the above-titled compound (Compound 38; 1.14 g) as white crystals (yield 74%).

Elemental Analysis for $C_{20}H_{23}N_3O_5$: Calcd.: C; 62.33, H; 6.01, N; 10.90 (%) Found: C; 61.95, H; 6.13, N; 10.93 (%)

$^1$H NMR δ ppm (200 MHz, CDCl$_3$) 1.30(3H,t,J=7.2Hz), 1.69(1H,br s), 2.16(1H,br s), 2.75(1H,br s), 3.04(2H,m), 4.20(2H,q,J=7.1Hz), 4.37(2H,dd,J=2.9,5.5Hz), 4.56(1H,m), 6.14(1H,m), 6.21(1H,m), 6.29(1H,m), 6.89(1H,d,J=8.5Hz), 7.08–7,37(6H,m)

Working Example 39

N-[N-[(2S,3S)-3-Carboxyaziridine-2-carbonyl]-L-phenylalanyl]furfurylamine Sodium Salt In substantially the same manner as Working Example 4, Compound 38 (606 mg) was subjected to alkali hydrolysis to give the above-titled compound (Compound 39; 560 mg) as a white powdery product (yield 88%).

Elemental Analysis for $C_{18}H_{18}N_3O_5Na.1.5\ H_2O$: Calcd.: C; 53.20, H; 5.21, N; 10.34 (%) Found: C; 53.44, H; 5.44, N; 10.45 (%)

$^1$H NMR δ ppm (200 MHz, D$_2$O) 2.35(1H,d,J=2.6Hz), 2.69(1H,d,J=2.3Hz), 2.98(1H,dd,J=8.0,13.7Hz), 3.10(1H, dd,J=7.2,13.7Hz), 4.24(1H,d,J=15.8Hz), 4.36(1H,d,J= 15.8Hz), 4.53(1H,t,J=7.3Hz), 6.19(1H,m), 6.40(1H,m), 7.20 (2H,m), 7.31(3H,m), 7.47(1H,m)

Working Example 40

N-[N-(2S,3S)-3-Ethoxycarbonylaziridine-2-carbonyl]-L-phenylalanyl]cyclohexylamine In substantially the same manner as Working Example 26, N-[(2S,3S)-3-ethoxycarbonylaziridine-2-carbonyl]-L-phenylalanine (1.22 g) was condensed with cyclohexylamine (0.44 g, manufactured by Wako Pure Chemical Industries, Ltd.) to give the above-titled compound (Compound 40; 0.92 g) as white crystals (yield 60%).

Elemental Analysis for $C_{21}H_{29}N_3O_4$: Calcd.: C; 65.10, H; 7.54, N; 10.84 (%) Found: C; 64.29, H; 7.41, N; 10.74 (%)

$^1$H NMR δ ppm (200 MHz, CDCl$_3$) 1.03(4H,m), 1.22 (2H,m), 1.30(3H,t,J=7.2Hz), 1.48–1.88(5H,m), 2.28(1H,br s), 2.77(1H,br s), 2.99(2H,d,J=7.2Hz), 3.66(1H,m), 4.22 (2H,q,J=7.1Hz), 4.48(1H,m), 5.54(1H,br s), 6.99(1H,d,J= 7.7Hz), 7.18(2H,m), 7.28(3H,m)

Working Example 41

N-[N-[(2S,3S)-3-carboxyaziridine-2-carbonyl]-L-phenylalanyl]cyclohexylamine Sodium Salt In substantially the same manner as Working Example 4, Compound 40 (308 mg) was subjected to alkali hydrolysis to give the above-titled compound (Compound 41; 280 mg) as a white powdery product (yield 84%).

Elemental Analysis for $C_{19}H_{24}N_3O_4Na.2H_2O$: Calcd.: C; 54.67, H; 6.76, N; 10.01 (%) Found: C; 54.30, H; 6.74, N; 10.10 (%)

$^1$H NMR δ ppm (200 MHz, D$_2$O) 0.83–1.41(6H,m), 1.45–1.83(6H,m), 2.41(1H,d,J=2.6Hz), 2.71(1H,d,J= 2.5Hz), 3.03(2H,d,J=7.4Hz), 3.47(2H,m), 4.46(1H,t,J= 7.0Hz), 7.32(5H,m)

Working Example 42

N-[N-[(2S,3S)-N-Methyl-3-ethoxycarbonylaziridine-2-carbonyl]-L-phenylalanyl]isopentylamine (2S,3S)-N-Z-Aziridine-2,3-dicarboxylic acid diethyl ester produced in Working Example 1 (2.00 g) was dissolved in ethanol (67 ml). To the solution was added Pd-C (10% (w/w), 200 mg), and the mixture was stirred for two hours at room temperature under the atmosphere of hydrogen gas. The catalyst was filtered off, and the filtrate was condensed to give diethyl ester of (2S,3S)-aziridine-2,3-dicarboxylic acid (1.05 g) as a colorless oily product (yield 90%).

Further, the product was dissolved in ethanol (50 ml), to which were added potassium carbonate (369 mg), sodium hydrogen carbonate (449 mg) and methyl p-toluenesulfonate (1.49 ml). The mixture was stirred for 14 hours at room temperature. The reaction mixture was poured into ice-water, which was subjected to extraction with ethyl acetate (100 ml×2). The ethyl acetate layer was washed with water and a saturated aqueous saline solution, which was dried over anhydrous sodium sulfate and subjected to a silica gel column chromatography. Elution was conducted with eluents prepared by adding ethyl acetate to hexane in sequence. The fractions eluted with 15% (v/v) ethyl acetate were combined and concentrated to dryness to give diethyl ester of (2S,3S)-N-methylaziridine-2,3-dicarboxylic acid (56 mg) as a colorless oily product (yield 5.2%). Further, from the fraction eluted with 40% (v/v) ethylacetate, the starting material (740 mg) was recovered, which was subjected to substantially the same reaction. The reaction time was prolonged to 64 hours, and the reaction mixture was subjected to post-treatment to give diethyl ester of (2S,3S)-N-methylaziridine- 2,3-dicarboxylic acid (116 mg) (yield 15%). The diethyl ester of (2S,3S)-N-methyl-aziridine-2,3-dicarboxylic acid thus obtained (172 mg) was dissolved in ethanol (8.5 ml). To the solution was added, under ice-cooling, 1N aqueous solution of sodium hydroxide (845 μl). The mixture was stirred for one hour and for further 30 minutes at room temperature. The reaction mixture was adjusted to pH 7, to which was added water, and the mixture was concentrated. The concentrate was adjusted to pH 7, followed by washing with ether. The aqueous layer was adjusted to pH 3, to which was added sodium chloride, followed by extraction with ethyl acetate. The ethyl acetate layer was washed with a saturated aqueous saline solution, dried over anhydrous sodium sulfate, followed by concentration to give monoethyl ester of (2S,3S)-N-methylaziridine-2,3-dicarboxylic acid (68 mg) as a white powdery product (yield 46%). This product was condensed, in substantially the same manner as Working Example 2, with N-(L-phenylalanyl)isopentylamine (100 mg) to afford the above-titled compound (Compound 42; 112 mg) as a white powdery product (yield 77%).

Elemental Analysis for $C_{21}H_{31}N_3O_4$: Calcd.: C; 64.76, H; 8.02, N; 10.79 (%) Found: C; 64.72, H; 7.81, H; 11.02 (%)

$^1$H NMR δ ppm (300 MHz, $CDCl_3$) 0.86(3H,d,J=6.6Hz), 0.87(3H,d,J=6.6Hz), 1.27(2H,m), 1.29(3H,t,J=7.2Hz), 1.46 (1H,m), 2.33(1H,d,J=2.3Hz), 2.62(3H,s), 2.66(1H,d,J= 2.3Hz), 2.94(1H,dd,J=7.6,13.8Hz), 3.05(1H,dd,J=7.5, 13.6Hz), 3.17(2H,m), 4.19(2H,m), 4.46(1H,dt,J=8.1,7.8Hz), 5.78(1H,br s), 6.93(1H,d,J=8.0Hz), 7.17(2H,m), 7.27(3H,m)

Working Example 43

N-[N-[(2S,3S)-N-Methyl-3-carboxyaziridine-2-carbonyl]-L-phenylalanyl]isopentylamine Sodium Salt In substantially the same manner as Working Example 4, Compound 42 (70 mg) was subjected to alkali hydrolysis to give the above-titled compound (Compound 43; 57 mg) as a white powdery product (yield 83%).

Elemental Analysis for $C_{19}H_{26}N_3O_4Na \cdot 1.5H_2O$: Calcd.: C; 55.60, H; 7.12, N; 10.24 (%) Found: C; 55.59, H; 7.19, N; 10.37 (%)

$^1$H NMR δ ppm (300 MHz, $D_2O$) 0.80(3H,d,J=6.2Hz), 0.81(3H,d,J=6.4Hz), 1.23(2H,m), 1.32(1H,m), 2.19–2.78 (5H,m), 2.95–3.22(4H,m), 4.46–4.61(1H,m), 7.23–7.42(5H, m)

$^1$H NMR δ ppm (75 MHz, $D_2O$): Compound 43 occurs as a mixture of two conformers in heavy water; the signal for the main conformer is shown. 24.5($CH_3$), 24.5($CH_3$), 27.7 (CH), 39.9($CH_2$), 40.2($CH_2$), 40.5($CH_2$), 40.9($CH_3$), 47.6 (CH), 48.7 (CH), 58.1 (CH), 130.1(CH), 131.7(CH)x2, 132.3(CH)x2, 139.1(Q), 173.9(Q), 175.3(Q), 175.8(Q)

Working Example 44

N-[N-[(2S,3S)-N-Ethyl-3-ethoxycarbonylaziridine-2-carbonyl]-L-phenylalanyl]isopentylamine In dichloromethane (37 ml) was dissolved diethyl ester of (2S,3S)-aziridine-2,3-dicarboxylic acid (1.10 g) obtained in Working Example 42. To the solution were added dropwise, under ice-cooling, triethylamine (4.10 ml) and ethyl trifluoromethanesulfonate (3.80 ml). The mixture was stirred for one hour. The reaction mixture was poured into ice-water, whose pH was adjusted to 7, followed by extraction with ethylacetate (100 ml×2). The ethyl acetate was washed with water and a saturated aqueous saline solution, which was dried over anhydrous sodium sulfate, followed by concentration. The concentrate was subjected to a silica gel column chromatography. Elution was conducted with eluents prepared by adding ethyl acetate to hexane in sequence. From the fraction eluted with 15% (v/v) ethyl acetate, diethyl ester of (2S,3S)-N-ethylaziridine-2,3-dicarboxylic acid (60 mg) was obtained as a colorless oily product (yield 4.7%). Further, from the fraction eluted with 30% (v/v) ethyl acetate, the starting material (780 mg) was recovered, which was subjected to substantially the same reaction as above to produce diethyl ester of (2S,3S)-N-ethyl-aziridine-2,3-dicarboxylic acid (25 mg) (yield 2.8%). The diethyl ester of (2S,3S)-N-ethylaziridine-2,3-dicarboxylic acid (85 mg) was dissolved in ethanol (4.2 ml). To the solution was added, under ice-cooling, a 1N aqueous solution of sodium hydroxide (390 μl). The mixture was processed in the same manner as in Working Example 42 to give monoethyl ester of (2S,3S)-N-ethyl-aziridine-2,3-dicarboxylic acid (65 mg) as a white powdery product (yield 89%). This product was condensed, in substantially the same manner as in Working Example 2, with N-(L-phenylalanyl)isopentylamine (92 mg) to give the above-titled compound (Compound 44; 96 mg) as a white powdery product (yield 68%).

Elemental Analysis for $C_{22}H_{33}N_3O_4$: Calcd.: C; 65.48, H; 8.24, N; 10.41 (%) Found: C; 65.19, H; 8.27, N; 10.83 (%)

$^1$H NMR δ ppm (300 MHz, $CDCl_3$) 0.85(3H,d,J=6.6Hz), 0.86(3H,d,J=6.6Hz), 1.03(3H,t,J=7.1Hz), 1.26(2H,m), 1.29 (3H,t,J=7.2Hz), 1.45(1H,m), 2.37(1H,d,J=2.3Hz), 2.71(1H, d,J=2.3Hz), 2.76(1H,m), 2.91(1H,m), 3.00(2H,m), 3.18(2H, m), 4.19(2H,q,J=7.0Hz), 4.46(1H,dt,J=8.1,7.6Hz), 5.73(1H, br s), 6.98(1H,d,J=8.1Hz), 7.18(2H,m), 7.28(3H,m)

Working Example 45

N-[N-[(2S,3S)-N-Ethyl-3-Carboxyaziridine-2-carbonyl]-L-phenylalanyl]isopentylamine Sodium Salt In substantially the same manner as Working Example 4, Compound 44 (70 mg) was subjected to alkali hydrolysis to give the above-titled compound (Compound 45; 44 mg) as a white powdery product (yield 64%).

Elemental Analysis for $C_{20}H_{28}N_3O_4Na \cdot H_2O$: Calcd.: C; 57.82, H; 7.28, N; 10.11 (%) Found: C; 57.75, H; 7.08, N; 10.19 (%)

$^1$H NMR δ ppm (300 MHz, $D_2O$) 0.80(6H,d,J=6.3Hz), 0.83–1.03(3H,m), 1.23(2H,m), 1.33(1H,m), 2.33–2.82(4H, m), 2.95–3.22(4H,m), 4.47–4.59(1H,m), 7.23–7.41(5H,m)

Working Example 46

N-[N-[(2S,3S)-N-Acetyl-3-carboxyaziridine-2-carbonyl]-L-phenylalanyl]isopentylamine Sodium Salt Compound 4 obtained in Working Example 4 (100 mg) was dissolved in N,N-dimethylformamide (2 ml), to which were added, under ice-cooling, pyridine (44 μl) and acetyl chloride (39 μl). The mixture was stirred for 1.5 hour under ice-cooling. To the reaction mixture was added water (50 ml), which was adjusted to pH 6.8. The mixture was then subjected to a Diaion HP-20 (10 ml) column chromatography, followed by elution with 50% (v/v) methanolic water. The eluent was concentrated and lyophilized to give the above-titled compound (Compound 46; 98 mg) as a white powdery product (yield 88%).

Elemental Analysis for $C_{20}H_{26}N_3O_5Na \cdot 2H_2O$: Calcd.: C; 53.68, H; 6.76, N; 9.39 (%) Found: C; 53.99, H; 6.56, N; 9.21 (%)

$^1$H NMR δ ppm (300 MHz, $D_2O$) 0.82(3H,d,J=6.5Hz), 0.83(3H,d,J=6.5Hz), 1.24(2H,m), 1.34(1H,m), 2.06(3H,s), 2.97–3.26(4H,m), 3.08(1H,d,J=2.0Hz), 3.32(1H,d,J= 2.0Hz), 4.56(1H,t,J=8.0Hz), 7.24–7.45(5H,m)

Working Example 47

N-[N-[(2S,3S)-3-ethoxycarbonylaziridine-2-carbonyl]-L-phenylalanyl]piperidine

In substantially the same manner as Working Example 26, Compound 26b (1.22 g) was condensed with piperidine (0.38 g, manufactured by Wako Pure Chemical Industries, Ltd.) to give the above-titled compound (Compound 47; 1.20 g) as a colorless oily product (yield 80%).

Elemental Analysis for $C_{20}H_{27}N_3O_4 \cdot 0.2H_2O$: Calcd.: C; 63.71, H; 7.32, N; 11.14 (%) Found: C; 63.78, H; 7.36, N; 11.00 (%)

$^1$H NMR δ ppm (200 MHz, CDCl$_3$) 1.11(1H,m), 1.30 (3H,t,J=7.1Hz), 1.47–1.79(6H,m), 2.42(1H,m), 2.78(1H,m), 2.85–3.16(3H,m), 3.27(1H,m), 3.50(2H,m), 4.22(2H,q,J=7.2Hz), 5.14(1H,m), 7.10–7.36(6H,m)

Working Example 48

N-[N-[(2S,3S)-3-carboxyaziridine-2-carbonyl]-L-phenylalanyl]piperidine Sodium Salt In substantially the same manner as Working Example 4, Compound 47 (610 mg) was subjected to alkali hydrolysis to give the above-titled compound (Compound 48; 460 mg) as a white powdery product (yield 77%).

Elemental Analysis for $C_{18}H_{22}N_3O_4Na \cdot 0.8H_2O$: Calcd.: C; 56.63, H; 6.23, N; 11.01 (%) Found: C; 56.65, H; 6.18, N; 11.05 (%)

$^1$H NMR δ ppm (300 MHz, D$_2$O) 0.95(1H,m), 1.18–1.50 (5H,m), 2.29(1H,d,J=2.6Hz), 2.58(1H,d,J=2.6Hz), 2.87(2H,d,J=7.6Hz), 3.02–3.35(4H,m), 4.93(1H,t,J=7.6Hz), 7.07–7.30(5H,m)

Working Example 49

N-[N-[(2S,3S)-3-ethoxycarbonylaziridine-2-carbonyl]-L-phenylalanyl]-1-aminopiperidine In substantially the same manner as Working Example 26, Compound 26b (1.22 g) was condensed with 1-aminopiperidine (0.45 g, manufactured by Wako Pure Chemical Industries, Ltd.) to give the above-titled compound (Compound 49; 0.83 g) as white crystals (yield 54%).

Elemental Analysis for $C_{20}H_{28}N_4O_4 \cdot 0.5H_2O$: Calcd.: C; 60.44, H; 7.35, N; 14.10 (%) Found: C; 60.43, H; 7.07, N; 14.12 (%)

Working Example 50

N-[N-[(2S,3S)-3-carboxyaziridine-2-carbonyl]-L-phenylalanyl]-1-aminopiperidine Sodium Salt In substantially the same manner as Working Example 4, Compound 49 (388 mg) was subjected to alkali hydrolysis to give the above-titled compound (Compound 50; 380 mg) as a white powdery product (yield 99%).

Elemental Analysis for $C_{18}H_{23}N_4O_4Na \cdot 1.4H_2O$: Calcd.: C; 53.04, H; 6.38, N; 13.75 (%) Found: C; 53.06, H; 6.58, N; 13.80 (%)

$^1$H NMR δ ppm (300 MHz, D$_2$O) 1.35(2H,m), 1.55(4H,m), 2.44(5H,m), 2.74(1H,s), 3.05(2H,m), 4.39(1H,m), 7.27 (2H,m), 7.39(3H,m)

Working Example 51

N-[N-[(2S,3S)-3-ethoxycarbonylaziridine-2-carbonyl]-L-phenylalanyl]-1-aminopyrrole In substantially the same manner as Working Example 26, Compound 26b (1.22 g) was condensed with 1-aminopyrrole (0.37 g, manufactured by Tokyo Kasei Co., Ltd.) to give the above-titled compound (Compound 51; 0.88 g) as white crystals (yield 60%).

Elemental Analysis for $C_{19}H_{22}N_4O_4$: Calcd.: C; 61.61, H; 5.99, N; 15.13 (%) Found: C; 61.28, H; 5.97, N; 15.05 (%)

$^1$H NMR δ ppm (200 MHz, CDCl$_3$) 1.30(3H,t,J=7.2Hz), 1.78(1H,t,J=8.2Hz), 2.21(1H,dd,2.2,7.7Hz), 2.79(1H,dd,J=2.2,8.8Hz), 3.04(1H,dd,J=8.0,13.8Hz), 3.17(1H,dd,J=7.5,13.8Hz), 4.22(1H,q,J=7.2Hz), 4.65(1H,m), 6.12(2H,m), 6.48(2H,m), 6.96(1H,d,J=8.1Hz), 7.23(2H,m), 7.32(3H,m), 8.88(1H,s)

Working Example 52

N-[N-[(2S,3S)-3-carboxyaziridine-2-carbonyl]-L-phenylalanyl]-1-aminopyrrole Sodium Salt In substantially the same manner as Working Example 4, Compound 51 (370 mg) was subjected to alkali hydrolysis to give the above titled compound (Compound 52; 280 mg) as a white powdery product (yield 77%).

Elemental Analysis for $C_{17}H_{17}N_4O_4Na \cdot 2.0H_2O$: Calcd.: C; 51.00, H; 5.29, N; 13.99 (%) Found: C; 50.99, H; 5.08, N; 13.94 (%)

$^1$H NMR δ ppm (300 MHz, D$_2$O) 2.50(1H,s), 2.70(1H,s), 3.20(2H,m), 4.70(1H,m), 6.13(2H,m), 6.47(2H,m), 7.34 (2H,m), 7.43(3H,m)

Working Example 53

N-[N-[(2S,3S)-3-ethoxycarbonylaziridine-2-carbonyl]-L-phenylalanyl]aniline

In substantially the same manner as Working Example 26, Compound 26b (1.22 g) was condensed with aniline (0.44 g, manufactured by Wako Pure Chemical Industries, Ltd.) to give the above-titled compound (Compound 53; 1.05 g) as white crystals (yield 69%).

Elemental Analysis for $C_{21}H_{23}N_3O_4$: Calcd.: C; 66.13, H; 6.08, N; 11.02 (%) Found: C; 65.61, H; 6.06, N; 11.05 (%)

$^1$H NMR δ ppm (200 MHz, CDCl$_3$) 1.30(3H,t,J=7.2Hz), 1.76(1H,dd,J=8.1,8.7Hz), 2.16(1H,dd,J=2.2,7.7Hz), 2.81(1H,dd,J=2.2,9.0Hz), 3.05(1H,dd,J=8.3,13.9Hz), 3.22(1H,dd,J=7.0,13.9Hz), 4.22(2H,q,J=7.2Hz), 4.66(1H,m), 6.97(1H,d,J=8.7Hz), 7.08–7.46(10H,m), 7.92(1H,s)

Working Example 54

N-[N-[(2S,3S)-3-carboxyaziridine-2-carbonyl]-L-phenylalanyl]aniline Sodium Salt

In substantially the same manner as Working Example 4, Compound 53 (572 mg) was subjected to alkali hydrolysis to give the above-titled compound (Compound 54; 500 mg) as a white powdery product (yield 89%).

Elemental Analysis for $C_{19}H_{18}N_3O_4Na \cdot 1.4H_2O$: Calcd.: C; 56.97, H; 5.23, N; 10.49 (%) Found: C; 56.95, H; 5.32, N; 10.50 (%)

$^1$H NMR δ ppm (300 MHz, D$_2$O) 2.50(1H,d,J=2.7Hz), 2.78(1H,d,J=2.7Hz), 3.20(2H,m), 4.65(1H,m), 7.21–7.42 (10H,m)

Working Example 55

N-[N-[(2S,3S)-3-ethoxycarbonylaziridine-2-carbonyl]-L-phenylalanyl]benzylamine

In substantially the same manner as Working Example 26, Compound 26b (1.22 g) was condensed with benzylamine (0.48 g, manufactured by Wako Pure Chemical Industries, Ltd.) to give the above-titled compound (Compound 55; 1.25 g) as white crystals (yield 79%).

Elemental Analysis for $C_{22}H_{25}N_3O_4$: Calcd.: C; 66.82, H; 6.37, N; 10.63 (%) Found: C; 66.66, H; 6.42, N; 10.67 (%)

$^1$H NMR δ ppm (200 MHz, CDCl$_3$) 1.30(3H,t,J=7.2Hz), 1.72(1H,m), 2.20(1H,dd,J=2.3,7.7Hz), 2.75(1H,dd,J=2.3, 9.0Hz), 2.99(1H,dd,J=7.7,13.8Hz), 3.13(1H,dd,J=7.5, 13.7Hz), 4.21(2H,q,J=7.1Hz), 4.37(2H,m), 4.56(1H,dt,J= 8.3,7.6Hz), 6.16(1H,m), 6.91(1H,d,J=8.4Hz), 7.02–7.36 (10H,m)

Working Example 56

N-[N-[(2S,3S)-3-carboxylaziridine-2-carbonyl]-L-phenylalanyl]benzylamine Sodium Salt In substantially the same manner as Working Example 4, Compound 55 (593 mg) was subjected to alkali hydrolysis to give the above-titled compound (Compound 56; 540 mg) as a white powdery product (yield 93%).

Elemental Analysis for $C_{20}H_{20}N_2O_4Na \cdot H_2O$: Calcd.: C; 58.96, H; 5.44, N; 10.31 (%) Found: C; 58.85, H; 5.44, N; 10.36 (%)

$^1$H NMR δ ppm (300 MHz, D$_2$O) 2.45(1H,m), 2.70(1H, m), 3.10(2H,m), 4.30(2H,m), 4.60(1H,m), 7.10(2H,m), 7.25 (2H,m), 7.35(6H,m)

Working Example 57

N-[N-[(2S,3S)-3-ethoxycarbonylaziridine-2-carbonyl]-L-phenylalanyl]-2-phenylethylamine In substantially the same manner as Working Example 26, Compound 26b (1.22 g) was condensed with 2-phenylethylamine (0.53 g, manufactured by Wako Pure Chemical industries, Ltd.) to give the above-titled compound (Compound 57; 1.20 g) as white crystals (yield 74%).

Elemental Analysis for $C_{23}H_{27}N_3O_4$: Calcd.: C; 67.46, H; 6.65, N; 10.26 (%) Found: C; 67.15, H; 6.54, N; 10.29 (%)

$^1$H NMR δ ppm (200 MHz, CDCl$_3$) 1.30(3H,t,J=7.2Hz), 1.70(1H,m), 2.17(1H,dd,J=2.2,7.8Hz), 2.71(2H,m), 2.74 (1H,dd,J=2.3,9.0Hz), 2.93(1H,dd,J=7.6,13.9Hz), 3.07(1H, dd,J=7.2,13.8Hz), 3.44(2H,m), 4.21(2H,q,J=7.1Hz), 4.45 (1H,m), 5.82(1H,m), 6.83(1H,d,J=8.3Hz), 7.00–7.35(10H, m)

Working Example 58

N-[N-[(2S,3S)-3-carboxyaziridine-2-carbonyl]-L-phenylalanyl]-2-phenylethylamine Sodium Salt In substantially the same manner as Working Example 4, Compound 57 (614 mg) was subjected to alkali hydrolysis to give the above-titled compound (Compound 58; 580 mg) as a white powdery product (yield 97%).

Elemental Analysis for $C_{21}H_{22}N_2O_4Na \cdot 1.4H_2O$: Calcd.: C; 58.85, H; 5.83, N; 9.80 (%) Found: C; 58.80, H; 5.68, N; 9.82 (%)

$^1$H NMR δ ppm (300 MHz, D$_2$O) 2.37(1H,m), 2.65(1H, m), 2.72(2H,m), 2.95(2H,m), 3.39(2H,m), 4.45(1H,m), 7.17–7.38(10H,m)

Working Example 59

N-[N-[(2S,3S)-3-ethoxycarbonylaziridine-2-carbonyl]-L-phenylalanyl]-1-adamantanamine In substantially the same manner as Working Example 26, Compound 26b (1.22 g) was condensed with 1-adamantanamine hydrochloride (0.83 g, manufactured by Wako Pure Chemical Industries, Ltd.) to give the above-titled compound (Compound 59; 0.14 g) as white crystals (yield 8.0%).

Elemental Analysis for $C_{25}H_{33}N_3O_4$: Calcd.: C; 68.31, H; 7.57, N; 9.56 (%) Found: C; 68.02, H; 7.34, N; 9.57 (%)

Working Example 60

N-[N-[(2S,3S)-3-carboxyaziridine-2-carbonyl]-L-phenylalanyl]-1-adamantanamine Sodium Salt In substantially the same manner as Working Example 4, Compound 59 (66 mg) was subjected to alkali hydrolysis to give the above-titled compound (Compound 60; 42 mg) as a white powdery product (yield 66%).

Elemental Analysis for $C_{23}H_{28}N_3O_4Na \cdot 2.2H_2O$: Calcd.: C; 58.39, H; 6.90, N; 8.88 (%) Found: C; 58.41, H; 6.64, N; 8.85 (%)

$^1$H NMR δ ppm (300 MHz, D$_2$O) 1.62(6H,m), 1.79(6H, m), 1.99(3H,m), 2.45(1H,m), 2.74(1H,m), 3.01(2H,m), 4.45 (1H,m), 7.26–7.39(5H,m)

Working Example 61

N-[N-[(2S,3S)-3-ethoxycarbonylaziridine-2-carbonyl]-L-phenylalanyl]-4-phenylbutylamine In substantially the same manner as Working Example 26, Compound 26b (1.22 g) was condensed with 4-phenylbutylamine (0.67 g, manufactured by Aldrich Chemical Company, Inc.) to give the above-titled compound (Compound 61; 0.90 g) as white crystals (yield 51%).

Elemental Analysis for $C_{25}H_{31}N_3O_4$: Calcd.: C; 68.63, H; 7.14, N; 9.60 (%) Found: C; 68.69, H; 7.03, N; 9.62 (%)

$^1$H NMR δ ppm (300 MHz, CDCl$_3$) 1.31(3H,t,J=7.1Hz), 1.43(2H,m), 1.53(2H,m), 1.73(1H,m), 2.21(1H,dd,J=2.3, 7.7Hz), 2.59(2H,m), 2.78(1H,dd,J=2.3,9.2Hz), 3.02(2H,m), 3.20(2H,m), 4.25(2H,q,J=7.2Hz), 4.49(1H,m), 5.79(1H,t,J= 5.7Hz), 6.91(1H,d,J=8.4Hz), 7.13–7.33(10H,m)

Working Example 62

N-[N-[(2S,3S)-3-carboxyaziridine-2-carbonyl]-L-phenylalanyl]-4-phenylbutylamine Sodium Salt In substantially the same manner as Working Example 4, Compound 61 (438 mg) was subjected to alkali hydrolysis to give the above-titled compound (Compound 62; 389 mg) as a white powdery product (yield 90%).

Elemental Analysis for $C_{23}H_{26}N_3O_4Na \cdot 1.4H_2O$: Calcd.: C; 60.49, H; 6.36, N; 9.20 (%) Found: C; 60.59, H; 6.22, N; 9.19 (%)

$^1$H NMR δ ppm (300 MHz, D$_2$O) 1.32(4H,m), 2.43(1H, m), 2.48(2H,m), 2.71(1H,d,J=2.4Hz), 2.98(2H,d,J=7.5Hz), 3.13(2H,m), 4.45(1H,t,J=7.8Hz), 7.14–7.32(10H,m)

Working Example 63

N-[N-[(2S,3S)-3-ethoxycarbonylaziridine-2-carbonyl]-L-phenylalanyl]-2-(2-pyridyl)ethylamine In substantially the same manner as Working Example 26, Compound 26b (1.22 g) was Condensed with 2-(2-aminoethyl)pyridine (0.56 g, manufactured by Aldrich Chemical Company, Inc.) to give the above-titled compound (Compound 63; 0.53 g) as white crystals (yield 32%).

Elemental Analysis for $C_{22}H_{26}N_4O_4$: Calcd.: C; 64.38, H; 6.38, N; 13.65 (%) Found: C; 64.30, H; 6.25, N; 13.63 (%)

¹H NMR δ ppm (300 MHz, CDCl₃) 1.30(3H,t,J=6.9Hz), 1.72(1H,t,J=8.4Hz), 2.21(1H,dd,J=2.3,7.7Hz), 2.76(1H,dd, J=2.3,9.2Hz), 2.87(2H,m), 3.00(2H,m), 3.60(2H,m), 4.21 (2H,q,J=7.2Hz), 4.53(1H,m), 6.90(2H,m), 7.04–7.24(7H, m), 7.59(1H,m), 8.45(1H,m)

Working Example 64

N-[N-[(2S,3S)-3-carboxyaziridine-2-carbonyl]-L-phenylalanyl]- 2-(2-pyridyl)ethylamine Sodium Salt In substantially the same manner as Working Example 4, Compound 63 (328 mg) was subjected to alkali hydrolysis to give the above-titled compound (Compound 64; 295 mg) as a white powdery product (yield 91%).

Elemental Analysis for $C_{20}H_{21}N_4O_4Na \cdot 1.5H_2O$: Calcd.: C; 55.68, H; 5.61, N; 12.99 (%) Found: C; 55.95, H; 5.66, N; 12.97 (%)

¹H NMR δ ppm (300 MHz, D₂O) 2.37(1H,br s), 2.66(1H, d,J=2.1Hz), 2.85(2H,m), 2.93(2H,m), 3.50(2H,m), 4.45(1H, m), 7.20(3H,m), 7.32(4H,m), 7.76(1H,m), 8.41(1H,m)

Working Example 65

N-[N-[(2S,3S)-3-ethoxycarbonylaziridine-2-carbonyl]-L-phenylalanyl]-2-thiazolylamine In substantially the same manner as Working Example 26, Compound 26b (1.22 g) was condensed with 2-aminothiazole (0.45 g, manufactured by Aldrich Chemical Company, Inc.) to give the above-titled compound (Compound 65; 0.77g) as white crystals (yield 50%).

Elemental Analysis for $C_{18}H_{20}N_4O_4S \cdot 0.3H_2O$: Calcd.: C; 54.89, H; 5.27, N; 14.23 (%) Found: C; 54.81, H; 5.07, N; 14.10 (%)

¹H NMR δ ppm (300 MHz, CDCl₃) 1.28(3H,t,J=6.9Hz), 1.85(1H,dd,J=7.8,8.4Hz), 2.32(1H,d,J=6.3Hz), 2.86(1H,d, J=8.4Hz), 3.10(2H,m), 4.20(2H,q,J=6.9Hz), 5.26(1H,m), 7.06(3H,m), 7.18(3H,m), 7.32(1H,d,J=8.4Hz), 7.62(1H,d,J= 3.6Hz), 12.31(1H,br s)

Working Example 66

N-[N-[(2S,3S)-3-carboxyaziridine-2-carbonyl]-L-phenylalanyl]-2-thiazolylamine Sodium Salt In substantially the same manner as Working Example 4, Compound 65 (210 mg) was subjected to alkali hydrolysis to give the above-titled compound (Compound 66; 169 mg) as a white powdery product (yield 82%).

Elemental Analysis for $C_{16}H_{15}N_4O_4SNa \cdot 1.6H_2O$: Calcd.: C; 46.74, H; 4.46, N; 13.63 (%) Found: C; 46.89, H; 4.50, N; 13.38 (%)

¹H NMR δ ppm (300 MHz, D₂O) 2.46(1H,br s), 2.76(1H, d,J=2.7Hz), 3.18(2H,m), 4.81(1H,m), 7.20(1H,d,J=3.9Hz), 7.25(2H,m), 7.32(3H,m), 7.44(1H,d,J=3.9Hz)

Working Example 67

N-[N-[(2S,3S)-3-ethoxycarbonylaziridine-2-carbonyl]-L-phenylalanyl]-3-phenyl-1-propylamine In substantially the same manner as Working Example 26, Compound 26b (1.17 g) was condensed with 3-phenyl-1-propylamine (0.57 g, manufactured by Aldrich Chemical Company, Inc.) to give the above-titled compound (Compound 67; 1.29 g) as white crystals (yield 80%).

Elemental Analysis for $C24H_{29}N_2O_4 \cdot 0.1H_2O$: Calcd.: C; 67.78, H; 6.92, N; 9.88 (%) Found: C; 67.53, H; 6.95, N; 9.99 (%)

¹H NMR δ ppm (300 MHz, CDCl₃) 1.29(3H,t,J=7.2Hz), 1.73(3H,m), 2.19(1H,dd,J=2.3,7.7Hz), 2.53(2H,m), 2.77 (1H,dd,J=2.3,9.2Hz), 3.00(2H,m), 3.22(2H,m), 4.20(2H,q, J=7.2Hz), 4.48(1H,m), 5.90(1H,t,J=5.4Hz), 6.90(1H,d,J= 7.8Hz), 7.07–7.33(10H,m)

Working Example 68

N-[N-[(2S,3S)-3-carboxyaziridine-2-carbonyl]-L-phenylalanyl]-3-phenyl-1-propylamine Sodium Salt In substantially the same manner as Working Example 4, Compound 67 (423 mg) was subjected to alkali hydrolysis to give the above-titled compound (Compound 68; 310 mg) as a white powdery product (yield 75%).

Elemental Analysis for $C_{22}H_{24}N_3O_4Na \cdot 2.0H_2O$: Calcd.: C; 58.27, H; 6.22, N; 9.27 (%) Found: C; 58.14, H; 6.22, N; 9.25 (%)

¹H NMR δ ppm (300 MHz, D₂O) 1.67(2H,m), 2.43(3H, m)., 2.72(1H,d,J=2.4Hz), 3.02(2H,d,J=8.1Hz), 3.13(2H,m), 4.47(1H,t,J=7.8Hz), 7.18–7.38(10H,m)

Working Example 69

N-[N-[(2S,3S)-3-ethoxycarbonylaziridine-2-carbonyl]-L-phenylalanyl]-N-methylbenzylamine In substantially the same manner as Working Example 26, Compound 26b (0.92 g) was condensed with N-methylbenzylamine (0.41 g, manufactured by Wako Pure Chemical Industries, Ltd.) to give the above-titled compound (Compound 69; 0.69 g) as an oily product (yield 57%).

Elemental Analysis for $C_{23}H_{27}N_3O_4 \cdot 0.3H_2O$: Calcd.: C; 66.58, H; 6.71, N; 10.13 (%) Found: C; 66.65, H; 6.89, N; 10.00 (%)

¹H NMR δ ppm (300 MHz, CDCl₃); Compound 69 occurs as a mixture of two conformers in CDCl₃; the signal for the main conformer is shown. 1.31(3H,t,J=6.9Hz), 2.40(1H,m), 2.71(3H,s), 2.71–3.10(3H,m), 4.22(2H,m), 4.40(1H,m), 4.66(1H,m), 5.13(1H,m), 7.00–7.35(11H,m)

Working Example 70

N-[N-[(2S,3S)-3-carboxyaziridine-2-carbonyl]-L-phenylalanyl]-N-methylbenzylamine Sodium Salt In substantially the same manner as Working Example 4, Compound 69 (387 mg) was subjected to alkali hydrolysis to give the above-titled compound (Compound 70; 304 mg) as a white powdery product (yield 80%).

Elemental Analysis for $C_{21}H_{22}N_3O_4Na \cdot 1.2H_2O$: Calcd.: C; 59.34, H; 5.79, N; 9.89 (%) Found: C; 59.36, H; 5.63, N; 9.87 (%)

¹H NMR δ ppm (300 MHz, D₂O); Compound 70 occurs as a mixture of two conformers in heavy water; the signal for the main conformer is shown. 2.32(1H,br s), 2.50(1H,br s), 2.77(3H,s), 3.03(2H,d,J=7.5Hz), 4.28(1H,d,J=15.0Hz), 4.63 (1H,d,J=15.0Hz), 5.08(1H,t,J=7.7Hz), 7.02(1H,m), 7.11 (2H,m), 7.23(1H,m), 7.31(6H,m)

Working Example 71

N-[N-[(2S,3S)-3-ethoxycarbonylaziridine-2-carbonyl]-L-phenylalanyl]-1-naphthalenemethylamine In substantially the same manner as Working Example 26, Compound 26b (0.92 g) was condensed with 1-naphthalenemethylamine (0.52 g, manufactured by Aldrich Chemical Company, Inc.) to give the above-titled compound (Compound 71; 0.47 g) as white crystals (yield 35%).

Elemental Analysis for $C_{26}H_{27}N_3O_4 \cdot 0.4H_2O$: Calcd.: C; 68.98, H; 6.19, N; 9.28 (%) Found: C; 68.85, H; 6.15, N; 9.26 (%)

$^1$H NMR δ ppm (300 MHz, CDCl$_3$) 1.28(3H,t,J=7.2Hz), 2.18(1H,d,J=6.6Hz), 2.65(1H,d,J=8.1Hz), 3.03(2H,m), 4.19 (2H,q,J=7.2Hz), 4.56(1H,m), 4.80(2H,m), 6.22(1H,br s), 6.94(1H,d,J=7.5Hz), 7.05–7.27(6H,m), 7.37(1H,m), 7.50 (2H,m), 7.76–7.88(3H,m)

Working Example 72

N-[N-[(2S,3S)-3-carboxyaziridine-2-carbonyl]-L-phenylalanyl]-1-naphthalenemethylamine Sodium Salt In substantially the same manner as Working Example 4, Compound 71 (356 mg) was subjected to alkali hydrolysis to give the above-titled compound (Compound 72; 248 mg) as a white powdery product (yield 71%).

Elemental Analysis for $C_{24}H_{22}N_3O_4Na \cdot 2.0H_2O$: Calcd.: C; 60.63, H; 5.51, N; 8.84 (%) Found: C; 60.58, H; 5.48, N; 8.80 (%)

$^1$H NMR δ ppm (300 MHz, D$_2$O) 2.44(1H,br s), 2.71(1H, br s), 2.93(2H,m), 4.45–4.70(3H,m), 6.99(2H,m), 7.06(4H, m), 7.30(1H,m), 7.43(2H,m), 7.72(3H,m)

Working Example 73

N-[N-[(2S,3S)-3-ethoxycarbonylaziridine-2-carbonyl]-L-phenylalanyl]-2-thiophenemethylamine In substantially the same manner as Working Example 26, Compound 26b (0.92 g) was condensed with 2-thiophenemethylamine (0.37 g, manufactured by Lancaster Synthesis Ltd.) to give the above-titled compound (Compound 73; 0.83 g) as white crystals (yield 69%).

Elemental Analysis for $C_{20}H_{23}N_3O_4S$: Calcd.: C; 59.83, H; 5.77, N; 10.47, S; 7.99 (%) Found: C; 59.92, H; 5.71, N; 10.47, S; 7.95 (%)

$^1$H NMR δ ppm (300 MHz, CDCl$_3$) 1.30(3H,t,J=7.2Hz), 1.69(1H,m), 2.16(1H,dd,J=1.8,7.5Hz), 2.73(1H,dd,J=1.8, 9.0Hz), 3.04(2H,m), 4.20(2H,q,J=7.2Hz), 4.56(3H,m), 6.43 (1H,br s), 6.87(3H,m), 7.21(6H,m)

Working Example 74

N-[N-[(2S,3S)-3-carboxyaziridine-2-carbonyl]-L-phenylalanyl]-2-thiophenemethylamine Sodium Salt In substantially the same manner as Working Example 4, Compound 73 (401 mg) was subjected to alkali hydrolysis to give the above-titled compound (Compound 74; 353 mg) as a white powdery product (yield 89%).

Elemental Analysis for $C_{18}H_{18}N_3O_4SNa \cdot 0.9H_2O$: Calcd.: C; 52.51, H; 4.85, N; 10.21, S; 7.79 (%) Found: C; 52.59, H; 4.97, N; 10.16, S; 8.06 (%)

$^1$H NMR δ ppm (300 MHz, D$_2$O) 2.42(1H,s), 2.70(1H, d,J=2.4Hz), 3.06(2H,m), 4.45(3H,m), 6.89(1H,m), 6.99(1H, m), 7.17–7.35(6H,m)

Working Example 75

N-[N-[(2S,3S)-3-ethoxycarbonylaziridine-2-carbonyl]-L-phenylalanyl]tetrahydrofurfurylamine In substantially the same manner as Working Example 26, Compound 26b (0.92 g) was condensed with tetrahydrofurfurylamine (0.33 g, manufactured by Tokyo Kasei Co., Ltd.) to give the above-titled compound (Compound 75; 0.48 g) as white crystals (yield 41%).

Elemental Analysis for $C_{20}H_{27}N_3O_5$: Calcd.: C; 61.68, H; 6.99, N; 10.79 (%) Found: C; 61.52, H; 6.84, N; 10.78 (%)

$^1$H NMR δ ppm (300 MHz, CDCl$_3$) 1.30(3H,t,J=7.2Hz), 1.73(1H,m), 1.88(4H,m), 2.18(1H,d,J=7.5Hz), 2.78(1H,dd, J=2.1,10.2Hz), 3.00(1H,m), 3.09(3H,m), 3.44(1H,m), 3.69 (1H,m), 3.81(1H,m), 4.20(2H,q,J=7.2Hz), 4.57(1H,m), 6.20 (1H,m), 6.91(1H,d,J=8.4Hz), 7.17(2H,m), 7.30(3H,m)

Working Example 76

N-[N-[(2S,3S)-3-carboxyaziridine-2-carbonyl]-L-phenylalanyl]tetrahydrofurfurylamine Sodium Salt In substantially the same manner as Working Example 4, Compound 75 (273 mg) was subjected to alkali hydrolysis to give the above-titled compound (Compound 76; 188 mg) as a white powdery product (yield 70%).

Elemental Analysis for $C_{18}H_{22}N_3O_5Na \cdot 1.0H_2O$: Calcd.: C; 53.86, H; 6.03, N; 10.40 (%) Found: C; 53.73, H; 6.04, N; 10.66 (%)

$^1$H NMR δ ppm (300 MHz, D$_2$O) 2.41(1H,s), 2.71(1H,s), 3.07(2H,m), 3.22(2H,m), 3.71(2H,m), 3.88(1H,m), 4.56 (1H,m), 7.27(2H,m), 7.37(3H,m)

Working Example 77

N-[N-[(2S,3S)-3-ethoxycarbonylaziridine-2-carbonyl]-L-phenylalanyl]-1-naphtylamine In substantially the same manner as Working Example 26, Compound 26b (0.92 g) was condensed with 1-naphtylamine (0.47 g, manufactured by Aldrich Chemical Company, Inc.) to give the above-titled compound (Compound 77; 0.40 g) as white crystals (yield 31%).

Elemental Analysis for $C_{25}H_{25}N_3O_4$: Calcd.: C; 69.59, H; 5.84, N; 9.74 (%) Found: C; 69.42, H; 6.00, N; 9.48 (%)

$^1$H NMR δ ppm (300 MHz, CDCl$_3$) 1.30(3H,t,J=7.2Hz), 1.77(1H,t,J=8.4Hz), 2.23(1H,dd,J=2.3,7.7Hz), 2.82(1H,dd, J=2.3,8.7Hz), 3.12(1H,dd,J=8.0,14.0Hz), 3.30(1H,dd,J=7.4, 14.0Hz), 4.21(2H,q,J=7.0Hz), 4.91(1H,m), 7.09(1H,d,J= 8.4Hz), 7.30(5H,m), 7.43(3H,m), 7.58(1H,d,J=7.2Hz), 7.65 (1H,d,J=8.4Hz), 7.81(1H,d,J=7.2Hz), 7.90(1H,d,J=7.2Hz), 8.60(1H,s)

Working Example 78

N-[N-[(2S,3S)-3-carboxyaziridine-2-carbonyl]-L-phenylalanyl]-1-naphtylamine Sodium Salt In substantially the same manner as Working Example 4, Compound 77 (200 mg) was subjected to alkali hydrolysis to give the above-titled compound (Compound 77; 194 mg) as a white powdery product (yield 99%).

Elemental Analysis for $C_{23}H_{20}N_3O_4Na \cdot 1.7H_2O$: Calcd.: C; 60.58, H; 5.17, N; 9.21 (%) Found: C; 60.26, H; 5.23, N; 9.63 (%)

$^1$H NMR δ ppm (300 MHz, D$_2$O) 2.53(1H,s), 2.82(1H,s), 3.23(2H,m), 4.89(1H,m), 7.20–7.65(10H,m), 7.70–7.95(2H, m)

Working Example 79

N-[N-[(2S,3S)-3-ethoxycarbonylaziridine-2-carbonyl]-L-phenylalanyl]-2-(2-thienyl)ethylamine In substantially the same manner as Working Example 26, Compound 26b (0.92 g) was condensed with 2-(2-thienyl)

ethylamine (0.42 g, manufactured by Maybridge Chemical Co., Ltd.) to give the above-titled compound (Compound 79; 1.04 g) as white crystals (yield 84%).

Elemental Analysis for $C_{21}H_{25}N_3O_4S$: Calcd.: C; 60.70, H; 6.06, N; 10.11, S;7.72 (%) Found: C; 60.67, H; 5.91, N; 10.01, S;7.68 (%)

$^1$H NMR δ ppm (300 MHz, CDCl$_3$) 1.30(3H,t,J=7.1Hz), 1.72(1H,m), 2.18(1H,d,J=6.3Hz), 2.74(1H,d,J=7.8Hz), 2.93 (3H,m), 3.06(1H,m), 3.46(2H,m), 4.21(2H,q,J=7.2Hz), 4.50 (1H,m), 6.06(1H,br s), 6.70(1H,m), 6.87(1H,d,J=8.4Hz), 6.91(1H,m), 7.14(3H,m), 7.30(3H,m)

Working Example 80

N-[N-[(2S,3S)-3-carboxyaziridine-2-carbonyl]-L-phenylalanyl]-2-(2-thienyl)ethylamine Sodium Salt In substantially the same manner as Working Example 4, Compound 79 (415 mg) was subjected to alkali hydrolysis to give the above-titled compound (Compound 80; 181 mg) as a white powdery product (yield 44%).

Elemental Analysis for $C_{19}H_{20}N_3O_4SNa.1.0H_2O$: Calcd.: C; 53.39, H; 5.19, N; 9.83, S; 7.50 (%) Found: C; 53.54, H; 5.13, N; 9.99, S; 7.51 (%)

$^1$H NMR δ ppm (300 MHz, D$_2$O) 2.39(1H,d,J=2.7Hz), 2.66(1H,d,J=2.4Hz), 2.93(3H,m), 3.04(1H,m), 3.41(2H,m), 4.50(1H,m), 6.83(1H,d,J=3.6Hz), 6.98(1H,dd,J=3.6,5.1Hz), 7.21(2H,m), 7.27(1H,d,J=4.8Hz), 7.35(3H,m)

Working Example 81

N-[N-[(2S,3S)-3-ethoxycarbonylaziridine-2-carbonyl]-L-phenylalanyl]-2,2-diphenylethylamine In substantially the same manner as Working Example 26, Compound 26b (0.92 g) was condensed with 2,2-diphenylethylamine (0.68 g, manufactured by Aldrich Chemical Company, Inc.) to give the above-titled compound (Compound 81; 0.43 g) as white crystals (yield 30%).

Elemental Analysis for $C_{29}H_{31}N_3O_4$: Calcd.: C; 71.73, H; 6.43, N; 8.65 (%) Found: C; 71.33, H; 6.45, N; 8.64 (%)

$^1$H NMR δ ppm (300 MHz, CDCl$_3$) 1.29(3H,t,J=7.1Hz), 1.64(1H,m), 2.13(1H,dd,J=2.4,7.5Hz), 2.62(1H,dd,J=2.3, 8.9Hz), 2.86(1H,dd,J=7.8,13.5Hz), 3.00(1H,dd,J=7.4, 13.7Hz), 3.82(2H,m), 4.03(1H,m), 4.20(2H,q,J=7.1Hz), 4.38(1H,m), 5.84(1H,t,J=5.4Hz), 6.75(1H,d,J=8.4Hz), 7.05–7.31(15H,m)

Working Example 82

N-[N-[(2S,3S)-3-carboxyaziridine-2-carbonyl]-L-phenylalanyl]-2,2-diphenylethylamine Sodium Salt In substantially the same manner as Working Example 4, Compound 81 (243 mg) was subjected to alkali hydrolysis to give the above-titled compound (Compound 82; 176 mg) as a white powdery product (yield 74%).

Elemental Analysis for $C_{27}H_{26}N_3O_4Na.1.3H_2O$: Calcd.: C; 64.48, H; 5.73, N; 8.36 (%) Found: C; 64.40, H; 5.60, N; 8.56 (%)

$^1$H NMR δ ppm (300 MHz, D$_2$O) 2.34(1H,br s), 2.61(1H, d,J=2.4Hz), 2.74(2H,m), 3.60(1H,dd,J=8.6,13.4Hz), 3.74 (1H,dd,J=7.8,12.9Hz), 4.00(1H,dd,J=7.8,8.4Hz), 4.37(1H, m), 6.90–7.20(15H,m)

Working Example 83

N-[N-[(2S,3S)-3-ethoxycarbonylaziridine-2-carbonyl]-L-phenylalanyl]-(S)-1-phenylethylamine In substantially the same manner as Working Example 26, Compound 26b (1.07 g) was condensed with (S)-1-phenylethylamine (0.46 g, manufactured by Aldrich Chemical Company, Inc.) to give the above-titled compound (Compound 83; 0.60 g) as white crystals (yield 42%).

Elemental Analysis for $C_{23}H_{27}N_3O_4.0.5H_2O$: Calcd.: C; 66.01, H; 6.74, N; 10.04 (%) Found: C; 66.00, H; 6.64, N; 9.91 (%)

$^1$H NMR δ ppm (300 MHz, CDCl$_3$) 1.30(3H,t,J=7.1Hz), 1.42(3H,d,J=6.9Hz), 1.74(1H,m), 2.22(1H,dd,J=2.2,7.7Hz), 2.79(1H,dd,J=2.4,9.0Hz), 2.99(2H,m), 4.22(2H,q,J=7.2Hz), 4.52(1H,m), 5.00(1H,m), 6.07(1H,d,J=8.1Hz), 6.94(1H,d,J= 8.1Hz), 7.09(4H,m), 7.24(6H,m)

Working Example 84

N-[N-[(2S,3S)-3-carboxyaziridine-2-carbonyl]-L-phenylalanyl]-(S)-1-phenylethylamine Sodium Salt In substantially the same manner as Working Example 4, Compound 83 (430 mg) was subjected to alkali hydrolysis to give the above-titled compound (Compound 84; 320 mg) as a white powdery product (yield 72%).

Elemental Analysis for $C_{21}H_{22}N_3O_4Na.1.0H_2O$: Calcd.: C; 59.85, H; 5.74, N; 9.97 (%) Found: C; 59.73, H; 5.85, N; 9.92 (%)

$^1$H NMR δ ppm (300 MHz, D$_2$O) 1.37(3H,d,J=7.0Hz), 2.46(1H,br s), 2.73(1H,d,J=2.5Hz), 3.01(2H,d,J=7.8Hz), 4.59(1H,t,J=7.7Hz), 4.83(1H,m), 7.00(2H,m), 7.15(2H,m), 7.31(6H,m)

Working Example 85

N-[N-[(2S,3S)-3-ethoxycarbonylaziridine-2-carbonyl]-L-phenylalanyl]-(R)-1-phenylethylamine In substantially the same manner as Working Example 26, Compound 26b (1.22 g) was condensed with (R)-1-phenylethylamine (0.53 g, manufactured by Aldrich Chemical Company, Inc.) to give the above-titled compound (Compound 85; 0.96 g) as white crystals (yield 59%).

Elemental Analysis for $C_{23}H_{27}N_3O_4$: Calcd.: C; 67.46, H; 6.65, N;.10.26 (%) Found: C; 67.19, H; 6.52, N; 10.28 (%)

$^1$H NMR δ ppm (300 MHz, CDCl$_3$) 1.30(3H,t,J=7.1Hz), 1.30(3H,d,J=6.9Hz), 1.71(1H,m), 2.24(1H,dd,J=2.3,7.7Hz), 2.76(1H,dd,J=2.1,8.7Hz), 3.02(2H,m), 4.21(2H,q,J=7.0Hz), 4.52(1H,m), 4.99(1H,m), 5.95(1H,d,J=6.9Hz), 6.93(1H,d,J= 8.4Hz), 7.10–7.40(10H,m)

Working Example 86

N-[N-[(2S,3S)-3-carboxyaziridine-2-carbonyl]-L-phenylalanyl]-(R)-1-phenylethylamine Sodium Salt In substantially the same manner as Working Example 4, Compound 85 (870 mg) was subjected to alkali hydrolysis to give the above-titled compound (Compound 86; 650 mg) as a white powdery product (yield 74%).

Elemental Analysis for $C_{21}H_{22}N_3O_4Na.0.7H_2O$: Calcd.: C; 60.62, H; 5.67, N; 10.10 (%) Found: C; 60.54, H; 5.88, N; 10.07 (%)

$^1$H NMR δ ppm (300 MHz, D$_2$O) 1.21(3H,d,J=7.0Hz), 2.43(1H,s), 2.69(1H,d,J=2.5Hz), 3.07(2H,m), 4.54(1H,m), 4.77(1H,m), 7.20–7.40(10H,m)

Working Example 87

N-[N-[(2S,3S)-3-ethoxycarbonylaziridine-2-carbonyl]-L-phenylalanyl]cyclohexanemethylamine In substantially the same manner as Working Example 26, Compound 26b (1.22 g) was condensed with cyclohexanemethylamine (0.50 g, manufactured by Wako Pure Chemical Industries, Ltd.) to give the above-titled compound. (Compound 87; 0.85 g) as white crystals (yield 53%).

Elemental Analysis for $C_{22}H_{31}N_3O_4$: Calcd.: C; 65.65, H; 8.01, N; 10.44 (%) Found: C; 65.51, H; 7.74, N; 10.68 (%)

$^1$H NMR δ ppm (300 MHz, CDCl$_3$) 0.79(2H,m), 1.14 (3H,m), 1.30(1H,m), 1.30(3H,t,J=7.2Hz), 1.52(2H,m), 1.65 (2H,m), 1.74(1H,m), 2.23(1H,dd,J=2.1,7.8Hz), 2.78(1H,dd, J=2.1,9.3Hz), 2.90–3.15(4H,m), 4.21(2H,q,J=7.1Hz), 4.51 (1H,m), 5.87(1H,t,J=5.9Hz), 6.94(1H,d,J=8.4Hz), 7.15–7.34(5H,m)

Working Example 88

N-[N-[(2S,3S)-3-carboxyaziridine-2-carbonyl]-L-phenylalanyl]cyclohexanemethylamine Sodium Salt In substantially the same manner as Working Example 4, Compound 87 (740 mg) was subjected to alkali hydrolysis to give the above-titled compound (Compound 88; 650 mg) as a white powdery product (yield 87%).

Elemental Analysis for $C_{20}H_{26}N_3O_4Na\cdot0.7H_2O$: Calcd.: C; 58.87, H; 6.76, N; 10.29 (%) Found: C; 58.58, H; 6.98, N; 10.19 (%)

$^1$H NMR δ ppm (300 MHz, D$_2$O) 0.72(2H,m), 1.10(3H, m), 1.24(1H,m), 1.40(2H,m), 1.60(3H,m), 2.44(1H,s), 2.72 (1H,d,J=2.5Hz), 2.79(1H,m), 3.01(1H,m), 3.05(2H,d,J= 7.8Hz), 4.51(1H,t,J=7.7Hz), 7.26(2H,m), 7.37(3H,m)

Working Example 89

N-[N-[(2S,3S)-N-methyl-3-ethoxycarbonylaziridine-2-carbonyl]-L-phenylalanyl]furfurylamine In substantially the same manner as Working Example 2, furfurylamine (2.91 g) was condensed with Boc-L-phenylalanine (8.75 g) to give N-(Boc-L-phenylalanyl) furfurylamine (9.14 g) (yield 89%). The Boc group of the product was deprotected by using TFA, and 0.43 g of thus-deprotected compound was condensed, in substantially the same manner as Working Example 42, with monoethyl ester of (2S,3S)-N-methylaziridine-2,3-dicarboxylic acid (0.28 g) to give the above-titled compound (Compound 89; 0.23 g) as white crystals (yield 36%).

Elemental Analysis for $C_{21}H_{25}N_3O_5$: Calcd.: C; 63.15, H; 6.31, N; 10.52 (%) Found: C; 62.99, H; 6.23, N; 10.48 (%)

$^1$H NMR δ ppm (300 MHz, CDCl$_3$) 1.30(3H,t,J=7.2Hz), 2.28(1H,d,J=2.4Hz), 2.62(3H,s), 2.64(1H,d,J=1.8Hz), 3.03 (2H,m), 4.18(2H,m), 4.37(2H,m), 4.52(1H,m), 6.15(1H,d, J=3.3Hz), 6.30(1H,dd,J=2.3,3.2Hz), 6.31(1H,m), 6.91(1H, d,J=8.4Hz), 7.12(2H,m), 7.22(3H,m), 7.33(1H,d,J=1.2Hz)

Working Example 90

N-[N-[(2S,3S)-N-methyl-3-carboxyaziridine-2-carbonyl]-L-phenylalanyl]furfurylamine Sodium Salt In substantially the same manner as Working Example 4, Compound 89 (100 mg) was subjected to alkali hydrolysis to give the above-titled compound (Compound 90; 56 mg) as a white powdery product (yield 52%).

Elemental Analysis for $C_{19}H_{20}N_3O_5Na\cdot2.0H_2O$: Calcd.: C; 53.15, H; 5.63, N; 9.76 (%) Found: C; 53.34, H; 5.50, N; 9.61 (%)

$^1$H NMR δ ppm (300 MHz, D$_2$O) 2.48(3H,s), 2.60(2H,m), 3.07(2H,m), 4.30(2H,m), 4.54(1H,m), 6.19(1H,m), 6.39 (1H,m), 7.15–7.38(5H,m), 7.44(1H,m)

Working Example 91

N-[N-[(2S,3S)-N-methyl-3-ethoxycarbonylaziridine-2-carbonyl]-L-phenylalanyl]benzylamine In substantially the same manner as Working Example 2, benzylamine (3.53 g) was condensed with Boc-L-phenylalanine (7.96 g) to give N-(Boc-L-phenylalanyl) benzylamine (9.30 g) (yield 87%). The compound thus obtained (7.08 g) was dissolved in ethyl acetate (100 ml), to which was added 4N hydrochloric acid/ethyl acetate solution (80 ml, manufactured by Kokusan Chemical Works, Ltd.), and the mixture was left standing for a half hour at room temperature. The reaction mixture was treated with ethylether to give N-(L-phenylalanyl)benzylamine hydrochloride (3.51 g) (yield 60%). The compound thus obtained (0.96 g) was condensed, in substantially the same manner as Working Example 8, with monoethyl ester of (2S,3S)-N-methylaziridine-2,3-dicarboxylic acid (0.52 g) obtained in Working Example 42 to give the above-titled compound (Compound 91; 0.86 g) as white crystals (yield 71%).

Elemental Analysis for $C_{23}H_{27}N_3O_4\cdot0.3H_2O$: Calcd.: C; 66.58, H; 6.70, N; 10.12 (%) Found: C; 66.50, H; 6.57, N; 10.16 (%)

$^1$H NMR δ ppm (300 MHz, CDCl$_3$) 1.29(3H,t,J=7.2Hz), 2.31(1H,d,J=2.1Hz), 2.62(3H,s), 2.64(1H,d,J=2.4Hz), 3.03 (2H,m), 4.19(2H,m), 4.36(2H,m), 4.53(1H,m), 6.19(1H,br s), 6.93(1H,d,J=8.1Hz), 7.13(4H,m), 7.26(6H,m)

Working Example 92

N-[N-[(2S,3S)-N-methyl-3-carboxyaziridine-2-carbonyl]-L-phenylalanyl]benzylamine Sodium Salt In substantially the same manner as Working Example 4, Compound 91 (740 mg) was subjected to alkali hydrolysis to give the above-titled compound (compound 92; 460 mg) as a white powdery product (yield 61%).

Elemental Analysis for $C_{21}H_{22}N_2O_4Na\cdot1.0H_2O$: Calcd.: C; 59.85, H; 5.74, N; 9.97 (%) Found: C; 59.93, H; 5.80, N; 9.81 (%)

$^1$H NMR δ ppm (300 MHz, D$_2$O) 2.48(3H,s), 2.59(2H,m), 3.06(2H,m), 4.33(2H,m), 4.60(1H,m), 7.11(2H,m), 7.24(2H, m), 7.32(6H,m)

Working Example 93

N-[N-[(2S,3S)-N-methyl-3-ethoxycarbonylaziridine-2-carbonyl]-L-phenylalanyl]-2-phenylethylamine In substantially the same manner as Working Example 2, 2-phenylethylamine (4.00 g) was condensed with Boc-L-phenylalanine (7.96 g) to give N-(Boc-L-phenylalanyl)-2-phenylethylamine (9.65 g) (yield 87%). The Boc group of the product was deprotected, in substantially the same manner as Working Example 91, to give N-(L-phenylalanyl) -2-phenylethylamine hydrochloride (4.93 g) (yield 81%). The compound thus obtained (1.00 g) was condensed, in substantially the same manner as Working Example 8, with monoethyl ester of (2S,3S)-N-methylaziridine-2,3-dicarboxylic acid (0.52 g) obtained in Working Example 42 to give the above-titled compound (Compound 93; 1.05 g) as white crystals (yield 83%).

Elemental Analysis for $C_{24}H_{29}N_3O_4\cdot0.5H_2O$: Calcd.: C; 66.64, H; 6.99, N; 9.71 (%) Found: C; 66.86, H; 6.85, N; 9.61 (%)

$^1$H NMR δ ppm (300 MHz, CDCl$_3$) 1.29(3H,t,J=7.1Hz), 2.80(1H,d,J=2.4Hz), 2.60(3H,s), 2.62(1H,d,J=2.7Hz), 2.71

(2H,m), 3.00(2H,m), 3.43(2H,m), 4.18(2H,m), 4.43(1H,m), 5.89(1H,br s), 6.85(1H,d,J=7.5Hz), 7.00–7.33(10H,m)

Working Example 94

N-[N-[(2S,3S)-N-methyl-3-carboxyaziridine-2-carbonyl]-L-phenylalanyl]-2-phenylethylamine Sodium Salt In substantially the same manner as Working Example 4, Compound 93 (890 mg) was subjected to alkali hydrolysis to give the above-titled compound (Compound 94; 760 mg) as a white powdery product (yield 83%).

Elemental Analysis for $C_{22}H_{24}N_3O_4Na \cdot 1.0H_2O$: Calcd.: C; 60.68, H; 6.02, N; 9.65 (%) Found: C; 60.98, H; 5.95, N; 9.54 (%)

$^1$H NMR δ ppm (300 MHz, $D_2O$) 2.45(3H,s), 2.52(2H,m), 2.73(2H,m), 2.96(2H,m), 3.45(2H,m), 4.45(1H,m), 7.15–7.40(10H,m)

Working Example 95

N-[N-[(2S,3S)-N-benzyl-3-ethoxycarbonylaziridine-2-carbonyl]-L-phenylalanyl]benzylamine Diethyl ester of (2S,3S)-aziridine-2,3-dicarboxylic acid (10.3 g) obtained in Working Example 42 was dissolved in DMF (155 ml). To the solution was added sodium carbonate (4.4 g) and benzyl bromide (14.1 g), and the mixture was stirred for 15 hours at 60° C. The reaction mixture was poured into ice-cooling water, which was subjected to extraction with ethyl acetate (100 ml×2). The ethyl acetate layer was washed with water and a saturated aqueous saline solution, which was dried over anhydrous sodium sulfate and subjected to a slica gel column chromatography. Elution was conducted with eluents prepared by adding ethyl acetate to hexane in sequence. The fractions eluted with 10% (v/v) ethyl acetate were combined and concentrated to dryness to give diethyl ester of (2S,3S)-N-benzylaziridine-2,3-dicarboxylic acid (12.3 g) as a colorless oily product (yield 81%). The whole amount of the product was dissolved in ethanol (300 ml). To the solution was added, under ice-cooling, 1N aqueous solution of sodium hydroxide (44 ml). The mixture was stirred for one hour and for further 30 minutes at room temperature. The reaction mixture was adjusted to pH7, to which was added water, and the mixture was concentrated. The concentrate was adjusted to pH7, followed by washing with ether. The aqueous layer was adjusted to pH 3, to which was added sodium chloride, followed by extraction with ethyl acetate. The ethyl acetate layer was washed with a saturated aqueous saline solution, dried over anhydrous sodium sulfate, followed by concentration to give monoethyl ester of (2S,3S)-N-benzylaziridine-2,3-dicarboxylic acid (2.0 g) as a white powdery product (yield 18%). The compound thus obtained (0.50 g) was condensed, in substantially the same manner as Working Example 8, with N-(L-phenylalanyl) benzylamine hydrochloride (0.64 g) obtained in Working Example 91 to give the above-titled compound (Compound 95; 0.91 g) as a white powdery product (yield 94%).

Elemental Analysis for $C_{29}H_{31}N_3O_4$: Calcd.: C; 71.73, H; 6.43, N; 8.65 (%) Found: C; 71.37, H; 6.32, N; 8.72 (%)

$^1$H NMR δ ppm (300 MHz, $CDCl_3$) 1.21(3H,t,J=7.2Hz), 2.46(1H,d,J=2.4Hz), 2.88(1H,d,J=2.4Hz), 3.06(2H,d,J=6.9Hz), 3.75(1H,d,J=13.2Hz), 4.06(1H,d,J=13.2Hz), 4.13 (2H,m), 4.33(2H,m), 4.56(1H,m), 5.92(1H,br s), 6.95(1H,d), 7.05–7.30(15H,m)

Working Example 96

N-[N-[(2S,3S)-N-benzyl-3-carboxyaziridine-2-carbonyl]-L-phenylalanyl]benzylamine Sodium Salt In substantially the same manner as Working Example 4, Compound 95 (496 mg) was subjected to alkali hydrolysis to give the above-titled compound (Compound 96; 320 mg) as a white powdery product (yield 59%).

Elemental Analysis for $C_{27}H_{26}N_3O_4Na \cdot 3.0H_2O$: Calcd.: C; 60.78, H; 6.05, N; 7.88 (%) Found: C; 60.56, H; 5.45, N; 8.04 (%)

$^1$H NMR δ ppm (300 MHz, $D_2O$) 2.76(1H,s), 2.84(1H,s), 2.91(2H,m), 3.80(1H,m), 3.99(1H,m), 4.30(2H,m), 4.54 (1H,m), 7.05–7.45(15H,m)

Working Example 97

N-[N-[(2S,3S)-N-benzyl-3-ethoxycarbonylaziridine-2-carbonyl]-n-phenylalanyl]-2-phenylethylamine In substantially the same manner as Working Example 8, monoethyl ester of (2S,3S)-N-benzylaziridine-2,3-dicarboxylic acid (0.50 g) obtained in Working Example 95 was condensed with N-(L-phenylalanyl)-2-phenylethylamine hydrochloride (0.67 g) obtained in Working Example 93 to give the above-titled compound (Compound 97; 0.67 g) as white powdery product (yield 67%).

Elemental Analysis for $C_{30}H_{33}N_3O_4$: Calcd.: C; 72.12, H; 6.66, N; 8.41 (%) Found: C; 71.68, H; 6.50, N; 8.51 (%)

$^1$H NMR δ ppm (300 MHz, $CDCl_3$) 1.20(3H,t,J=7.1Hz), 2.45(1H,d,J=2.1Hz), 2.65(2H,m), 2.86(1H,d,J=1.8Hz), 3.01 ((2H,d,J=7.5Hz), 3.38(2H,m), 3.93(1H,m), 4.04(1H,m), 4.12(2H,m), 4.44(1H,m), 5.67(1H,m), 6.88(1H,d,J=7.5Hz), 7.00–7.40(15H,m)

Working Example 98

N-[N-[(2S,3S)-N-benzyl-3-carboxyaziridine-2-carbonyl]-L-phenylalanyl]-2-phenylethylamine Sodium Salt In substantially the same manner as Working Example 4, Compound 97 (415 mg) was subjected to alkali hydrolysis to give the above-titled compound (Compound 98; 330 mg) as a white powdery product (yield 73%).

Elemental Analysis for $C_{28}H_{28}N_3O_4Na \cdot 1.5H_2O$: Calcd.: C; 64.60, H; 6.00, N; 8.07 (%) Found: C; 64.53, H; 5.89, N; 8.09 (%)

$^1$H NMR δ ppm (300 MHz, $D_2O$) 2.65–2.95(6H,m), 3.39(2H,m), 3.72(1H,d,J=13.2Hz), 3.97(1H,d,J=14.1Hz), 4.40(1H,m), 7.05–7.40(15H,m)

Working Example 99

N-[N-[(2S,3S)-N-benzyl-3-ethoxycarbonylaziridine-2-carbonyl]-L-phenylalanyl]-1-naphthalenemethylamine In substantially the same manner as Working Example 2, 1-naphthalenemethylamine (4.32 g) was condensed with Boc-L-phenylalanine (6.63 g) to give N-(Boc-L-phenylalanyl)-1-naphthalenemethylamine (7.92 g) (yield 91%). The Boc group of the product was deprotected in substantially the same manner as Working Example 91 to give N-(L-phenylalanyl)-1-naphthalenemethylamine hydrochloride (4.24 g) (yield 64%). The compound thus obtained (0.75 g) was condensed, in substantially the same manner as Working Example 8, with monoethyl ester of (2S,3S)-N-benzylaziridine-2,3-dicarboxylic acid (0.50 g) obtained in Working Example 95 to give the above-titled compound (Compound 99; 0.79 g) as white crystals (yield 74%).

Elemental Analysis for $C_{33}H_{33}N_3O_4$: Calcd.: C; 74.00, H; 6.21, N; 7.84 (%) Found: C; 73.70, H; 6.21, N; 7.90 (%)

¹H NMR δ ppm (300 MHz, CDCl₃) 1.20(3H,t,J=7.4Hz), 2.45(1H,d,J=2.4Hz), 2.85(1H,d,J=1.8Hz), 3.04(2H,d,J=6.6Hz), 3.91(1H,d,J=14.4Hz), 4.04(1H,d,J=12.9Hz), 4.13(2H,m), 4.52(1H,m), 4.80(2H,m), 5.96(1H,br s), 6.97(1H,d,J=8.4Hz), 7.11(2H,m), 7.21(9H,m), 7.38(1H,m), 7.51(2H,m), 7.86(3H,m)

Working Example 100

N-[N-[(2S,3S)-N-benzyl-3-carboxyaziridine-2-carbonyl]-L-phenylalanyl]-1-naphthalenemethylamine Sodium Salt In substantially the same manner as Working Example 4, Compound 99 (535 mg) was subjected to alkali hydrolysis to give the above-titled compound (Compound 100; 290 mg) as a white powdery product (yield 49%).

Elemental Analysis for C₃₁H₂₈N₂O₄Na.3.8H₂O: Calcd.: C; 62.26, H; 5.99, N; 7.02 (%) Found: C; 61.86, H; 5.10, N; 6.60 (%)

¹H NMR δ ppm (300 MHz, DMSO-d₆) 2.30(1H,m), 2.49(1H,m), 2.90(2H,m), 3.95(1H,d,J=14.5Hz), 4.13(1H,d,J=14.5Hz), 4.57(1H,m), 4.73(2H,m), 7.05–7.35(10H,m), 7.41(1H,m), 7.54(3H,m), 7.85(1H,m), 7.95(1H,m), 8.02(1H,m)

Working Example 101

N-[N-[(2S,3S)-N-methyl-3-ethoxycarbonylaziridine-2-carbonyl]-L-phenylalanyl]-1-naphthalenemethylamine In substantially the same manner as Working Example 8, N-(L-phenylalanyl)-1-naphthalenemethylamine hydrochloride (0.63 g) obtained in Working Example 99 was condensed with monoethyl ester of (2S,3S)-N-methylaziridine-2,3-dicarboxylic acid (0.29 g) obtained in Working Example 42 to give the above-titled compound (Compound 101; 0.19 g) as white crystals (yield 24%).

Elemental Analysis for C₂₇H₂₉N₃O₄: Calcd.: C; 70.57, H; 6.36, N; 9.14 (%) Found: C; 70.33, H; 6.29, N; 8.95 (%)

¹H NMR δ ppm (300 MHz, CDCl₃) 1.29(3H,t,J=7.3Hz), 2.31(1H,d,J=2.3Hz), 2.60(3H,s), 2.60(1H,m), 2.95(1H,m), 3.08(1H,m), 4.18(2H,m), 4.50(1H,m), 4.77(1H,m), 4.88(1H,m), 6.07(1H,m), 6.93(1H,d,J=5.9Hz), 7.10(2H,m), 7.18(3H,m), 7.28(1H,m), 7.39(1H,m), 7.51(2H,m), 7.82(3H,m)

Working Example 102

N-[N-[(2S,3S)-N-methyl-3-carboxyaziridine-2-carbonyl]-L-phenylalanyl]-1-naphthalenemethylamine Sodium Salt In substantially the same manner as Working Example 4, Compound 101 (140 mg) was subjected to alkali hydrolysis to give the above-titled compound (Compound 102; 100 mg) as a white powdery product (yield 67%).

Elemental Analysis for C₂₅H₂₄N₃O₄Na.2.5H₂O: Calcd.: C; 60.23, H; 5.86, N; 8.43 (%) Found: C; 59.89, H; 5.52, N; 8.34 (%)

¹H NMR δ ppm (300 MHz, DMSO-d₆) 2.10(1H,m), 2.29(1H,m), 2.50(3H,s), 2.92(2H,m), 4.52(1H,m), 4.75(2H,m), 7.13(2H,m), 7.22(3H,m), 7.33(1H,m), 7.43(2H,m), 7.54(1H,m), 7.81(1H,m), 7.95(1H,m), 8.05(1H,m), 8.70(1H,m)

Working Example 103

N-[N-[(2S,3S)-N-allyl-3-ethoxycarbonylaziridine-2-carbonyl]-L-phenylalanyl]-1-naphthalenemethylamine Diethyl ester of (2S,3S)-aziridine-2,3-dicarboxylic acid (9.36 g) obtained in Working Example 42 was dissolved in DMF (230 ml). To the solution was added sodium carbonate (5.3 g) and allyl iodide (12.6 g), and the mixture was stirred for 15 hours at 45° C. The reaction mixture was treated in substantially the same manner as Working Example 95 to give diethyl ester of (2S,3S)-N-allylaziridine-2,3-dicarboxylic acid (5.2 g) as a colorless oily product (yield 46%). 2.27 g of thus-obtained compound was subjected to alkali hydrolysis in substantially the same manner as Working Example 95 to give monoethyl ester of (2S,3S)-N-allylaziridine-2,3-dicarboxylic acid (1.21 g) as a white powdery product (yield 48%). The compound thus obtained (0.34 g) was condensed, in substantially the same manner as Working Example 8, with N-(L-phenylalanyl)-1-naphthalenemethylamine hydrochloride (0.64 g) obtained in Working Example 99 to give the above-titled compound (Compound 103; 0.34 g) as a white powdery product (yield 41%).

Elemental Analysis for C₂₉H₃₁N₃O₄: Calcd.: C; 71.73, H; 6.43, N; 8.65 (%) Found: C; 71.53, H; 6.54, N; 8.72 (%)

¹H NMR δ ppm (300 MHz, CDCl₃) 1.26(3H,t,J=7.4Hz), 2.36(1H,m), 2.69(1H,m), 3.03(2H,m), 3.34(1H,m), 3.49(1H,m), 4.14(2H,m), 4.53(1H,m), 4.83(2H,m), 5.03(1H,d,J=10.3Hz), 5.12(1H,d,J=18.1Hz), 5.79(1H,m), 6.11(1H,m), 6.97(1H,d,J=9.2Hz), 7.10(2H,m), 7.18(3H,m), 7.28(1H,m), 7.38(1H,m), 7.51(2H,m), 7.86(3H,m)

Working Example 104

N-[N-[(2S,3S)-N-allyl-3-carboxyaziridine-2-carbonyl]-L-phenylalanyl]-1-naphthalenemethylamine Sodium Salt In substantially the same manner as Working Example 4, Compound 103 (240 mg) was subjected to alkali hydrolysis to give the above-titled compound (Compound 104; 177 mg) as a white powdery product (yield 71%).

Elemental Analysis for C₂₇H₂₆N₃O₄Na.1.5H₂O: Calcd.: C; 64.02, H; 5.77, N; 8.30 (%) Found: C; 64.43, H; 5.65, N; 8.43 (%)

¹H NMR δ ppm (300 MHz, DMSO-d₆) 2.18(1H,m), 2.29(1H,m), 2.89(2H,m), 3.44(2H,m), 4.57(1H,m), 4.72(2H,m), 4.95(1H,m), 5.13(1H,dd,J=2.3,19.3Hz), 5.81(1H,m), 7.11(2H,m), 7.18(3H,m), 7.34(1H,m), 7.45(2H,m), 7.56(2H,m), 7.87(1H,m), 7.96(1H,m), 8.04(1H,m), 8.65(1H,m)

Working Example 105

N-[N-[(2S,3S)-N-formyl-3-carboxyaziridine-2-carbonyl]-L-phenylalanyl]isopentylamine Sodium Salt To Compound 4 (103 mg) obtained in Working Example 4 were added formic acid (1.0 ml) and acetic anhydride (0.2 ml), and the mixture was stirred for one hour at room temperature. To the reaction mixture was added an ice-cooled 2% aqueous solution of sodium hydrogen carbonate (50 ml), which was subjected to a Diaioin HP-20 (10 ml) column chromatography after adjustment to pH 6.6. Elution was conducted by the use of 50% (v/v) methanolic water. The eluate was concentrated, and the concentrate was lyophilized to give a powdery product. The powdery product was purified with analytical HPLC [column, YMC-Pack D-ODS-5, manufactured by YMC Co., Ltd; mobile phase, 25% acetonitrile/0.01M phosphate buffer (pH 6.3); flow rate, 10 ml/min.]. Fractions which give a single peak in the analytical HPLC were collected and concentrated, which was subjected to a Diaioin HP-20 (5 ml) column chromatography. Elution was conducted by the use of 50% (v/v)

methanolic water. The eluate was concentrated, and the concentrate was lyophilized to give the above-titled compound (Compound 105; 34 mg) as a white powdery product (yield 31%).

Elemental Analysis for $C_{19}H_{24}N_3O_5Na \cdot 1.5H_2O$: Calcd.: C; 53.77, H; 6.41, N; 9.90, Na; 5.42 (%) Found: C; 53.84, H; 6.20, N; 10.04, Na; 5.21 (%)

$^1$H NMR δ ppm (300 MHz, $D_2O$) 0.81(3H,d,J=6.5Hz), 0.83(3H,d,J=6.5Hz), 1.15–1.42(3H,m), 2.98–3.24(4H,m), 3.08(1H,d,J=2.5Hz), 3.34(1H,d,J=2.5Hz), 4.55(1H,t,J=8.0Hz), 7.23–7.46(5H,m), 8.59(1H,s)

Working Example 106

N-[N-[(2S,3S)-N-Z-3-ethoxycarbonylaziridine-2-carbonyl]-3-(2-naphthyl)-L-alanyl]isopentylamine In substantially the same manner as Working Example 2, isopentylamine (232 μl) was condensed with Boc-3-(2-naphthyl)-L-alanine (631 mg, manufactured by BACHEM Fein Chemikalien AG., Switzerland) to give N-(Boc-3-(2-naphthyl)-n-alanyl)isopentylamine (560 mg) as a white powdery product (yield 73%). The Boc group of the product was deprotected by using TFA, and 364 mg of thus-obtained compound was condensed, in substantially the same manner as Working Example 2, with Compound 1 (419 mg) to give the above-titled compound (Compound 106; 470 mg) as a white powdery product (yield 66%).

Elemental Analysis for $C_{32}H_{37}N_3O_6 \cdot 0.25H_2O$: Calcd.: C; 68.13, H; 6.70, N; 7.45 (%) Found: C; 68.10, H; 6.57, N; 7.37 (%)

$^1$H NMR δ ppm (300 MHz, $CDCl_3$) 0.72(3H,d,J=6.6Hz), 0.75(3H,d,J=6.6Hz), 1.10(2H,m), 1.22(3H,t,J=7.1Hz), 1.26 (1H,m), 2.97(1H,d,J=2.5Hz), 3.00–3.24(4H,m), 3.36(1H,d,J=2.5Hz), 4.13(2H,m), 4.57(1H,dt,J=6.4,8.1Hz), 5.10(1H,d,J=12.0Hz), 5.20(1H,d,J=12.0Hz), 5.35(1H,t,J=5.8Hz), 6.90 (1H,d,J=7.9Hz), 7.34(6H,m), 7.47(2H,m), 7.60(1H,m), 7.79 (3H,m)

Working Example 107

N-[N-[(2S,3S)-3-ethoxycarbonylaziridine-2-carbonyl]-3-(2-naphthyl)-L-alanyl]isopentylamine In substantially the same manner as Working Example 3, Compound 106 (400 mg) was subjected to catalytic reduction to thereby deprotect the Z group, followed by concentration. The resulting precipitate was collected by filtration, washed with water and then dried. The dry product was subjected to a silica gel column chromatography (50 ml). Elution was conducted with eluents prepared by adding ethyl acetate to hexane in sequence. The eluate with 50% (v/v) ethyl acetate was concentrated to dryness Go give the above-titled compound (Compound 107; 166 mg) as a white powdery product (yield 55%).

Elemental Analysis for $C_{24}H_{31}N_3O_4$: Calcd.: C; 67.74, H; 7.34, N; 9.87 (%) Found: C; 67.58, H; 7.35, N; 10.10 (%)

$^1$H NMR δ ppm (300 MHz, $CDCl_3$) 0.75(3H,d,J=6.4Hz), 0.78(3H,d,J=6.4Hz), 1.16(2H,m), 1.26(3H,t,J=7.1Hz), 1.33 (1H,m), 1.72(1H,m), 2.19(1H,m), 2.77(1H,m), 3.06–3.25 (4H,m), 4.17(2H,q,J=7.1Hz), 4.58(1H,m), 5.65(1H,br s), 6.99(1H,d,J=8.3Hz), 7.32(1H,d,J=8.2Hz), 7.47(2H,m), 7.62 (1H,br s), 7.80(3H,m)

Working Example 108

N-[N-[(2S,3S)-3-carboxyaziridine-2-carbonyl]-3-(2-naphthyl)-L-alanyl]isopentylamine In substantially the same manner as Working Example 4, Compound 107 (80 mg) was subjected to alkali hydrolysis. After adjustment to pH 3.0, the resulting precipitate was collected by filtration, washed with water and dried to give the above-titled compound (Compound 108; 56 mg) as a white powdery product (yield 75%).

Elemental Analysis for $C_{22}H_{27}N_3O_4 \cdot 0.25H_2O$: Calcd.: C; 65.73, H; 6.90, N; 10.45 (%) Found: C; 65.80, H; 6.82, N; 10.48 (%)

$^1$H NMR δ ppm (300 MHz, DMSO-$d_6$) 0.75(3H,d,J=6.5Hz), 0.77(3H,d,J=6.6Hz), 1.16(2H,m), 1.39(1H,m), 2.33 (1H,m), 2.72(1H,m), 2.91–3.16(4H,m), 4.59(1H,m), 7.39 (1H,d,J=8.1Hz), 7.47(2H,m), 7.69(1H,s), 7.82(2H,m), 7.85 (1H,m), 8.01(1H,t,J=5.6Hz)

Working Example 109

N-[N-[(2S,3S)-N-Z-3-ethoxycarbonylaziridine-2-carbonyl]-3-(2-naphthyl)-L-alanyl]benzylamine In substantially the same manner as Working Example 2, benzylamine (0.93 g) was condensed with Boc-3-(2-naphthyl)-L-alanine (2.50 g) to give N-(Boc-3-(2-naphthyl)-L-alanyl)benzylamine (3.0 g) as white crystals (yield 94%). The Boc group of the product was deprotected by using 4N hydrochloric acid/ethyl acetate solution, and 1.82 g of thus-obtained compound was condensed, in substantially the same manner as Working Example 2, with Compound 1 (1.47 g) to give the above-titled compound (Compound 109; 0.85 g) as white crystals (yield 29%).

Elemental Analysis for $C_{34}H_{33}N_3O_6 \cdot 0.5H_2O$: Calcd.: C; 69.37, H; 5.82, N; 7.13 (%) Found: C; 69.49, H; 5.68, N; 7.21 (%)

$^1$H NMR δ ppm (300 MHz, $CDCl_3$) 1.21(3H,t), 2.99(1H, d), 3.16(2H,d,J=7.3Hz), 3.38(1H,d), 4.18(2H,m), 4.30(1H, m), 4.37(1H,dd,J=6.7,15.5Hz), 4.66(1H,m), 5.09(1H,d,J=12.2Hz), 5.19(1H,d), 5.86(1H,dd,J=5.5,6.7Hz), 6.89(2H,m), 6.99(1H,d,J=8.8Hz), 7.12(3H,m), 7.34(6H,m), 7.48(2H,m), 7.59(1H,m), 7.75(3H,m)

Working Example 110

N-[N-[(2S,3S)-3-ethoxycarbonylaziridine-2-carbonyl]-3-(2-naphthyl)-L-alanyl]benzylamine In substantially the same manner as Working Example 3, Compound 109 (0.85 g) was subjected to catalytic reduction to thereby deprotect the Z group, followed by concentration. The resulting precipitate was collected by filtration to give the above-titled compound (Compound 110; 385 mg) as a white powdery product (yield 57%).

Elemental Analysis for $C_{26}H_{27}N_2O_4 \cdot 0.5H_2O$: Calcd.: C; 68.70, H; 6.20, N; 9.24 (%) Found: C; 68.89, H; 6.13, N; 9.01 (%)

$^1$H NMR δ ppm (300 MHz, $CDCl_3$) 1.26(3H,t,J=7.2Hz), 1.71(1H,dd,J=7.3,8.5Hz), 2.19(1H,m), 2.76(1H,m), 3.22 (2H,m), 4.19(2H,m), 4.34(2H,m), 4.66(1H,m), 6.07(1H,dd, J=5.1,6.3Hz), 6.98(2H,m), 7.15(3H,m), 7.34(2H,m), 7.48 (2H,m), 7.61(1H,m), 7.77(3H,m)

Working Example 111

N-[N-[(2S,3S)-3-carboxyaziridine-2-carbonyl]-3-(2-naphthyl)-L-alanyl]benzylamine Sodium Salt In substantially the same manner as Working Example 4, Compound 110 (222 mg) was subjected to alkali hydrolysis to give the above-titled compound (Compound 111; 74 mg) as a white powdery product (yield 32%).

Elemental Analysis for $C_{24}H_{22}N_3O_4Na \cdot 1.0H_2O$: Calcd.: C; 63.01, H; 5.29, N; 9.19 (%) Found: C; 62.98, H; 5.55, N; 8.89 (%)

¹H NMR δ ppm (300 MHz, DMSO-d₆) 1.68(1H,m), 1.98(1H,m), 2.77(1H,m), 3.05(2H,m), 4.28(2H,m), 4.68 (1H,m), 7.07(2H,m), 7.17(3H,m), 7.48(3H,m), 7.83(4H,m), 8.77(1H,m), 9.31(1H,m)

Working Example 112

N-[N-[(2S,3S)-3-ethoxycarbonylaziridine-2-carbonyl]-L-phenylalanyl]-N-methyl-2-phenylethylamine In substantially the same manner as Working Example 26, Compound 26b (0.92 g) was condensed with N-methyl-2-phenylethylamine (0.45 g, manufactured by Wako Pure Chemical Industries, Ltd.) to give the above-titled compound (Compound 112; 0.50 g) as an oily product (yield 39%).

Elemental Analysis for $C_{24}H_{29}N_3O_4$: Calcd.: C; 68.07, H; 6.90, N; 9.92 (%) Found: C; 67.59, H; 6.41, N; 9.20 (%)

¹H NMR δ ppm (300 MHz, CDCl₃);Compound 112 occurs as a mixture of two conformers in CDCl₃; the signal for the main conformer is shown. 1.31(3H,t,J=6.9Hz), 1.73 (1H,dd,J=7.4,8.9Hz), 2.38(1H,m), 2.70(3H,s), 2.81(2H,m), 2.88(2H,m), 3.43(2H,m), 4.23(2H,m), 5.11(1H,m), 7.02–7.28(11H,m)

Working Example 113

N-[N-[(2S,3S)-3-carboxyaziridine-2-carbonyl]-L-phenylalanyl]-N-methyl-2-phenylethylamine Sodium Salt In substantially the same manner as Working Example 4, Compound 112 (400 mg) was subjected to alkali hydrolysis to give the above-titled compound (Compound 113; 250 mg) as a white powdery product (yield 61%).

Elemental Analysis for $C_{22}H_{24}N_3O_4Na.1.0H_2O$: Calcd.: C; 60.68, H; 6.02, N; 9.65 (%) Found: C; 60.20, H; 5.93, N; 9.63 (%)

¹H NMR δ ppm (300 MHz, DMSO-d₆); Compound 113 occurs as a mixture of two conformers in DMSO-d6; the signal for the main conformer is shown. 1.44(1H,m), 1.87 (1H,m), 2.21(1H,m), 2.69(2H,m), 2.73(2H,m), 2.77(3H,s), 3.59(2H,m), 4.84(1H,m), 7.10–7.29(10H,m), 7.60(1H,m)

Working Example 114

N-[N-[(2S,3S)-3-ethoxycarbonylaziridine-2-carbonyl]-L-phenylalanyl]-L-phenylalanine Benzyl Ester In substantially the same manner as Working Example 8, Compound 26b (0.92 g) was condensed with L-phenylalanine benzyl ester tosylate (1.41 g) to give the above-titled compound (Compound 114; 0.94 g) as white crystals (yield 58%).

Elemental Analysis for $C_{31}H_{33}N_3O_6$: Calcd.: C; 68.49, H; 6.12, N; 7.73 (%) Found: C; 68.31, H; 6.02, N; 7.66 (%)

¹H NMR δ ppm (300 MHz, CDCl₃) 1.30(3H,t), 1.67(1H, dd,J=7.1,9.4Hz), 2.11(1H,m), 2.70(1H,m), 2.91(1H,dd,J= 8.2,14.1Hz), 3.06(3H,m), 4.21(2H,q,J=7.2Hz), 4.53(1H,m), 4.83(1H,m), 5.12(2H,s), 6.36(1H,d,J=8.7Hz), 6.74(1H,d,J= 10.4Hz), 6.93(2H,m), 7.10–7.38(13H,m)

Working Example 115

N-[N-[(2S,3S)-3-carboxyaziridine-2-carbonyl]-L-phenylalanyl]-L-phenylalanine Disodium Salt In substantially the same manner as Working Example 4, Compound 114 (720 mg) was subjected to alkali hydrolysis to give the above-titled compound (Compound 115; 405 mg) as a white powdery product (yield 58%).

Elemental Analysis for $C_{22}H_{21}N_3O_6Na_2.3.0H_2O$: Calcd.: C; 50.48, H; 5.20, N; 8.03 (%) Found: C; 50.02, H; 4.87, N; 7.93 (%)

¹H NMR δ ppm (300 MHz, DMSO-d₆) 1.39(1H,m), 2.00(1H,m), 2.33(1H,m), 2.58(2H,m), 2.86(1H,m), 3.09 (1H,m), 4.09(1H,m), 4.21(1H,m), 7.07–7.26(10H,m)

Working Example 116

N-[N-[(2S,3S)-3-n-propylcarbamoylaziridine-2-carbonyl]-L-phenylalanyl]isopentylamine In substantially the same manner as Working Example 4, Compound 3 (200 mg) was subjected to alkali hydrolysis, then the pH was adjusted to pH 3.0, followed by extraction with ethyl acetate (50 ml×3). The ethyl acetate layer was washed with water and a saturated aqueous saline solution, which was dried over anhydrous sodium sulfate, followed by concentration to dryness to afford N-[N-[(2S,3S)-3-carboxyaziridine-2-carbonyl]-L-phenylalanyl] isopentylamine (183 mg) as a white powdery product (yield 99%). 150 mg of thus-obtained compound was condensed, in substantially the same manner as Working Example 2, with n-propylamine (36 μl, manufactured by Wako Pure Chemical Industries, Ltd.) to give the above-titled compound (Compound 116; 143 mg) as a white powdery product (yield 85%).

Elemental Analysis for $C_{21}H_{32}N_4O_3.0.2H_2O$: Calcd.: C; 64.32, H; 8.33, N; 14.29 (%) Found: C; 64.24, H; 8.13, N; 14.55 (%)

¹H NMR δ ppm (300 MHz, CDCl₃) 0.84(3H,d,J=6.6Hz), 0.85(3H,d,J=6.6Hz), 0.92(3H,t,J=7.5Hz), 1.24(2H,m), 1.44 (1H,m), 1.52(2H,m), 2.35(1H,br s), 2.64(1H,d,J=2.2Hz), 3.04(2H,d,J=7.5Hz), 3.06–3.27(4H,m), 4.59(1H,dt,J=8.1, 7.5Hz), 6.06(1H,br s), 6.51(1H,t,J=5.6Hz), 7.17–7.33(5H, m), 7.40(1H,d,J=8.0Hz)

Working Example 117

N-[N-[(2S,3S)-3-benzyloxycarbonylaziridine-2-carbonyl]-L-phenylalanyl]-2-phenylethylamine Compound 58 (100 mg) was dissolved in DMF (5 ml). To the solution was added benzyl bromide (44.2 μl, manufactured by Wako Pure Chemical Inudstries, Ltd.), and the mixture was stirred for 24 hours at room temperature. The reaction mixture was concentrated, dissolved in ethyl acetate, washed with water and a saturated aqueous saline solution, which was dried over anhydrous sodium sulfate. The dry product as concentrated and subjected to a silica gel column chromatography (20 ml). Elution was conducted with eluents prepared by adding ethyl acetate to hexane in sequence. The eluate with 50% (v/v) ethyl acetate was concentrated to dryness to give the above-titled compound (Compound 117; 64 mg) as a white powdery product (yield 55%).

Elemental Analysis for $C_{28}H_{29}N_2O_4$: Calcd.: C; 71.32, H; 6.20, N; 8.91 (%) Found: C; 71.23, H; 6.12, N; 8.89 (%)

¹H NMR δ ppm (300 MHz, CDCl₃) 1.73(1H,br s), 2.24(1H,br s), 2.70(2H,m), 2.75(1H,br s), 2.98(2H,m), 3.43 (2H,m), 4.45(1H,m), 5.13(1H,d,J=12.1Hz), 5.21(1H,d,J= 12.1Hz), 5.81(1H,br s), 6.82(1H,d,J=8.2Hz), 7.02–7.43 (15H,m)

Working Example 118

N-[N-[(2S,3S)-3-pivaloyloxymethoxycarbonylaziridine-2-carbonyl]-L-phenylalanyl]-2-phenylethylamine Compound 58 (150 mg) was dissolved in DMF (7.5 ml). To the solution was added pivalic acid chloromethyl ester (107 μl, manufactured by Tokyo Kasei Co., Ltd.), and the mixture was stirred for 24 hours at room temperature. The reaction mixture was concentrated, dissolved in ethyl acetate, washed with water and a saturated aqueous saline solution, which was dried over anhydrous sodium sulfate. The dry product was concentrated and powderized from ethyl acetate-hexane to give the above-titled compound (Compound 118; 93 mg) as a white powdery product (yield 50%).

Elemental Analysis for $C_{27}H_{33}N_3O_6$: Calcd.: C; 65.44, H; 6.71, N; 8.48 (%) Found: C; 65.09, H; 6.48, N; 8.84 (%)

$^1$H NMR δ ppm (300 MHz, CDCl$_3$) 1.23(9H,s), 2.23(1H, br s), 2.70(2H,m), 2.77(1H,br s), 2.99(2H,m), 3.45(2H,m), 4.45(1H,m), 5.76(1H,d,J=5.5Hz), 5.81(1H,d,J=5.5Hz), 6.84 (1H,d,J=9.8Hz), 7.02–7.33(10H,m)

Working Exmample 119

N-[N-[(2S,3S)-3-ethoxycarbonylaziridine-2-carbonyl]-L-phenylalanyl]-p-chlorobenzylamine In substantially the same manner as Working Example 26, Compound 26b (0.92 g) was condensed with p-chlorobenzylamine (0.47 g, manufactured by Aldrich Chemical Company, Inc.) to give the above-titled compound (Compound 119; 0.97 g) as white crystals (yield 75%).

Elemental Analysis for $C_{22}H_{24}N_3O_4Cl$: Calcd.: C; 61.47, H; 5.63, N; 9.77 (%) Found: C; 61.25, H; 5.56, N; 9.55 (%)

$^1$H NMR δ ppm (300 MHz, CDCl$_3$) 1.30(3H,t,J=7.1Hz), 1.74(1H,m), 2.21(1H,m), 2.74(1H,m), 2.97(1H,dd,J=7.4, 13.7Hz), 3.10(1H,dd,J=7.7,13.4Hz), 4.21(2H,m), 4.25(1H, m), 4.37(1H,m), 4.58(1H,m), 6.40(1H,m), 6.94(1H,d,J=8.1Hz), 7.01(2H,d,J=7.8Hz), 7.15(2H,m), 7.26(5H,m)

Working Example 120

N-[N-[(2S,3S)-3-carboxyaziridine-2-carbonyl]-L-phenylalanyl]-p-chlorobenzylamine Sodium Salt In substantially the same manner as Working Example 4, Compound 119 (430 mg) was subjected to alkali hydrolysis to give the above-titled compound (Compound 120; 187 mg) as a white powdery product (yield 42%).

Elemental Analysis for $C_{20}H_{19}N_3O_4ClNa.1.2H_2O$: Calcd.: C; 53.93, H; 4.84, N; 9.43 (%) Found: C; 53.98, H; 4.91, N; 9.28 (%)

$^1$H NMR δ ppm (300 MHz, DMSO-D$_6$) 1.45(1H,m), 1.95(1H,m), 2.38(1H,m), 2.95(2H,m), 4.19(1H,dd,J=5.9, 15.6Hz), 4.29(1H,dd,J=5.9,15.6Hz), 4.39(1H,m), 7.18(2H, d,J=8.5Hz), 7.23(5H,m), 7.35(2H,d,J=8.3Hz), 8.81(1H,br s), 9.37(1H,br s)

Working Example 121

N-[N-[(2S,3S)-3-ethoxycarbonylaziridine-2-carbonyl]-L-phenylalanyl]-2-(p-chlorophenyl)ethylamine In substantially the same manner as Working Example 26, Compound 26b (0.92 g) was condensed with 2-(p-chlorophenyl)ethylamine (0.51 g, manufactured by Tokyo Kasei Co., Ltd.) to give the above-titled compound (Compound 121; 0.94 g) as white crystals (yield 71%).

Elemental Analysis for $C_{23}H_{26}N_3O_4Cl$: Calcd.: C; 62.23, H; 5.90, N; 9.47 (%) Found: C; 62.05, H; 5.80, N; 9.71 (%)

$^1$H NMR δ ppm (300 MHz, CDCl$_3$) 1.30(3H,t,J=7.1Hz), 1.73(1H,t,J=8.4Hz), 2.18(1H,m), 2.64(2H,m), 2.73(1H,m), 2.93(1H,dd,J=7.7,13.7Hz), 3.06(1H,dd,J=7.3,13.7Hz), 3.41 (2H,q,J=6.6Hz), 4.21(2H,q,J=7.1Hz), 4.45(1H,m), 5.93(1H, br s), 6.83(1H,d,J=8.0Hz), 6.99(2H,d,J=8.0Hz), 7.13–7.33 (7H,m)

Working Example 122

N-[N-[(2S,3S)-3-carboxyaziridine-2-carbonyl]-L-phenylalanyl]-2-(p-chlorophenyl)ethylamine Sodium Salt In substantially the same manner as Working Example 4, Compound 121 (444 mg) was subjected to alkali hydrolysis to give the above-titled compound (Compound 122; 396 mg) as a white powdery product (yield 90%).

Elemental Analysis for $C_{21}H_{21}N_3O_4ClNa.0.6H_2O$: Calcd.: C; 56.22, H; 4.99, N; 9.37 (%) Found: C; 56.35, H; 5.22, N; 9.34 (%)

$^1$H NMR δ ppm (300 MHz, DMSO-d$_6$) 2.02(1H,m), 2.41(1H,m), 2.68(2H,t,J=7.1Hz), 2.82(2H,m), 3.27(2H,m), 4.37(1H,m), 7.14–7.35(9H,m), 8.52(1H,m)

Working Example 123

N-[N-[(2S,3S)-3-ethoxycarbonylaziridine-2-carbonyl]-L-phenylalanyl]-2-(p-methoxyphenyl)ethylamine In substantially the same manner as Working Example 26, Compound 26b (0.92 g) was condensed with 2-(p-methoxyphenyl)ethylamine (0.50 g, manufactured by Tokyo Kasei Co., Ltd.) to give the above-titled compound (Compound 123; 0.92 g) as white crystals (yield 70%).

Elemental Analysis for $C_{24}H_{29}N_3O_5$: Calcd.: C; 65.59, H; 6.65, N; 9.56 (%) Found: C; 65.34, H; 6.49, N; 9.38 (%)

$^1$H NMR δ ppm (300 MHz, CDCl$_3$) 1.30(3H,t,J=7.1Hz), 1.70(1H,m), 2.19(1H,m), 2.65(2H,m), 2.72(1H,m), 2.99 (2H,m), 3.40(2H,m), 3.78(3H,s), 4.21(2H,m), 4.45(1H,m), 5.79(1H,m), 6.81(2H,d,J=8.7Hz), 6.84(1H,m), 6.96(2H,d,J=8.5Hz), 7.15(2H,m), 7.28(3H,m)

Working Example 124

N-[N-[(2S,3S)-3-carboxyaziridine-2-carbonyl]-L-phenylalanyl]-2-(p-methoxyphenyl)ethylamine Sodium Salt In substantially the same manner as Working Example 4, Compound 123 (440 mg) was subjected to alkali hydrolysis to give the above-titled compound (Compound 124; 209 mg) as a white powdery product (yield 48%).

Elemental Analysis for $C_{22}H_{24}N_3O_5Na$: Calcd.: C; 60.96, H; 5.58, N; 9.69 (%) Found: C; 61.26, H; 6.05, N; 9.61 (%)

$^1$H NMR δ ppm (300 MHz, DMSO-d$_6$) 2.30(1H,m), 2.60(2H,m), 2.70(1H,m), 2.74(1H,dd,J=9.6,13.8Hz), 2.92 (1H,dd,J=4.8,13.5Hz), 3.21(2H,m), 3.71(3H,s), 4.47(1H,m), 6.84(2H,d,J=8.4Hz), 7.10(2H,d,J=8.4Hz), 7.17–7.29(5H, m), 8.16(1H,m)

Working Example 125

N-[N-[(2S,3S)-3-ethoxycarbonylaziridine-2-carbonyl]-L-phenylalanyl]-p-trifluoromethylbenzylamine In substantially the same manner as Working Example 26, Compound 26b (0.92 g) was condensed with p-trifluoromethylbenzylamine (0.58 g, manufactured by Tokyo Kasei Co., Ltd.) to give the above-titled compound (compound 125; 1.10 g) as white crystals (yield 79%).

Elemental Analysis for $C_{23}H_{24}N_3O_4F_3 \cdot 0.3H_2O$: Calcd.: C; 58.92, H; 5.29, N; 8.96 (%) Found: C; 59.00, H; 5.03, N; 8.91 (%)

$^1$H NMR δ ppm (300 MHz, DMSO-d$_6$) 1.20(3H,t,J= 7.2Hz), 2.53(1H,m), 2.77(1H,m), 2.82(1H,m), 3.03(1H,m), 4.12(2H,m), 4.35(2H,m), 4.59(1H,m), 7.26(5H,m), 7.36 (2H,d,J=8.1Hz), 7.65(2H,d,J=7.5Hz), 8.74(1H,m), 9.02(1H, d,J=8.1Hz)

Working Example 126

N-[N-[(2S,3S)-3-carboxyaziridine-2-carbonyl]-L-phenylalanyl]-p-trifluoromethylbenzylamine Sodium Salt In substantially the same manner as Working Example 4, Compound 125 (463 mg) was subjected to alkali hydrolysis to give the above-titled compound (Compound 126; 390 mg) as a white powdery product (yield 85%).

Elemental Analysis for $C_{21}H_{19}N_3O_4F_3Na$: Calcd.: C; 55.15, H; 4.19, N; 9.19 (%) Found: C; 55.85, H; 4.58, N; 9.16 (%)

$^1$H NMR δ ppm (300 MHz, DMSO-d$_6$) 2.29(1H,m), 2.67(1H,m), 2.86(1H,dd,J=9.0,13.5Hz), 3.02(1H,dd,J=5.6, 13.7Hz), 4.35(2H,m), 4.57(1H,m), 7.23(5H,m), 7.35(2H,d, J=8.1Hz), 7.65(2H,d,J=8.4Hz), 8.48(1H,m), 8.75(1H,m)

Working Example 127

N-[N-[(2S,3S)-3-ethoxycarbonylaziridine-2-carbonyl]-L-phenylalanyl]-N-methyl-2-(2-pyridyl)ethylamine In substantially the same manner as Working Example 26, Compound 26b (0.92 g) was condensed with 2-(2-methylaminoethyl)pyridine (0.45 g, manufactured by Aldrich Chemical Company, Inc.) to give the above-titled compound (Compound 127; 0.99 g) as an oily product (yield 78%).

Elemental Analysis for $C_{23}H_{28}N_4O_4 \cdot 0.5CHCl_3$: Calcd.: C; 58.29, H; 5.93, N; 11.57 (%) Found: C; 58.05, H; 6.10, N; 11.28 (%)

$^1$H NMR δ ppm (300 MHz, CDCl$_3$) 1.30(3H,m), 1.72 (1H,m), 2.35(1H,m), 2.66–3.10(8H,m), 3.40–3.80(2H,m), 4.22(1H,m), 5.09(1H,m), 7.14(5H,m), 7.26(3H,m), 7.59 (1H,m), 8.15(1H,m)

Working Example 128

N-[N-[(2S,3S)-3-carboxyaziridine-2-carbonyl]-L-phenylalanyl]-N-methyl-2-(2-pyridyl)ethylamine Sodium Salt In substantially the same manner as Working Example 4, Compound 127 (637 mg) was subjected to alkali hydrolysis to give the above-titled compound (Compound 128; 567 mg) as a white powdery product (yield 90%).

Elemental Analysis for $C_{21}H_{23}N_4O_4Na \cdot 0.6H_2O$: Calcd.: C; 58.76, H; 5.68, N; 13.05 (%) Found: C; 58.69, H; 5.66, N; 12.91 (%)

$^1$H NMR δ ppm (300 MHz, DMSO-d$_6$) 1.48(1H,m), 1.92(1H,m), 2.27(1H,m), 2.70–3.00(9H,m), 3.40–3.80(2H, m), 4.89(1H,m), 7.10–7.30(9H,m), 7.70(1H,m), 8.49(1H,m)

Working Example 129

N-[N-[(2S,3S)-3-ethoxycarbonylaziridine-2-carbonyl]-L-phenylalanyl]-N-methyl-1-naphthalenemethylamine In substantially the same manner as Working Example 26, Compound 26b (450 mg) was condensed with N-methyl-1-naphthalenemethylamine (250μl) to give the above-titled compound (Compound 129; 421 mg)(yield 62%).

Elemental Analysis for $C_{27}H_{29}N_3O_4 \cdot 0.5H_2O$: Calcd.: C; 69.21, H; 6.45, N; 8.97 (%) Found: C; 69.53, H; 6.25, N; 8.63 (%)

$^1$H NMR δ ppm (300 MHz, CD$_3$OD) 1.30(3H,m), 2.35–3.15(7H,m), 4.22(2H,m), 4.90–5.20(3H,m), 6.95–8.05 (12H,m)

Working Example 130

N-[N-[(2S,3S)-3-carboxyaziridine-2-carbonyl]-L-phenylalanyl]-N-methyl-1-naphthalenemethylamine Sodium Salt In substantially the same manner as Working Example 4, Compound 129 (102 mg) was subjected to alkali hydrolysis to give the above-titled compound (Compound 130; 68 mg) as a white powdery product (yield 68%).

Elemental Analysis for $C_{25}H_{24}N_3O_4Na \cdot 2.0H_2O$: Calcd.: C; 61.34, H; 5.77, N; 8.58, Na; 4.70 (%) Found: C; 61.39, H; 5.58, N; 8.53, Na; 4.96 (%)

$^1$H NMR δ ppm (300 MHz, D$_2$O) 2.25–2.90(7H,m), 4.38–5.07(3H,m), 6.80–7.80(12H,m)

Working Example 131

N-[N-[(2S,3S)-3-ethoxycarbonylaziridine-2-carbonyl]-L-tyrosyl]-N-methyl-2-phenylethylamine In substantially the same manner as Working Example 2, N-methyl-2-phenylethylamine (782 μl) was condensed with Boc-(O-benzyl)-L-tyrosine (2.00 g, manufactured by Peptide Institute, Inc.) to give N-[Boc-(O-benzyl)-L-tyrosyl]-N-methyl-2-phenylethylamine (2.56 g) as a colorless oily product (yield 97%). The Boc group of the product was deprotected by using TFA, and 1.94 g of thus-obtained compound was condensed, in substantially the same manner as Working Example 2, with Compound 1 (1.47 g) to give N-[N-[(2S,3S)-N-Z-3-ethoxycarbonylaziridine-2-carbonyl]-(O-benzyl)-L-tyrosyl]-N-methyl-2-phenylethylamine (1.53 g) as a white powdery product (yield 46%). This compound was subjected to catalytic reduction to thereby deprotect the Z group and benzyl group in substantially the same manner as Working Example 3 to give the above-titled compound (Compound 131; 930 mg) as white crystals (yield 98%).

Elemental Analysis for $C_{24}H_{29}N_3O_5 \cdot 0.3H_2O$: Calcd.: C; 64.79, H; 6.71, N; 9.45 (%) Found: C; 65.14, H; 7.04, N; 9.02 (%)

$^1$H NMR δ ppm (300 MHz, CDCl$_3$); Compound 131 occurs as a mixture of two conformers in CDCl$_3$; the signal for the main conformer is shown. 1.28(3H,t,J=7.2Hz), 2.46 (1H,br s), 2.75(3H,s), 2.77(5H,m), 3.40(2H,m), 4.20(2H,m), 5.04(1H,m), 6.71(2H,d,J=8.5Hz), 6.95(2H,d,J=8.5Hz), 7.02 (1H,d,J=8.4Hz), 7.10–7.32(5H,m)

Working Example 132

N-[N-[(2S,3S)-3-carboxyaziridine-2-carbonyl]-L-tyrosyl]-N-methyl-2-phenylethylamine Sodium Salt In substantially the same manner as Working Example 4, Compound 131 (220 mg) was subjected to alkali hydrolysis to give the above-titled compound (Compound 132; 138 mg) as a white powdery product (yield 64%).

Elemental Analysis for $C_{22}H_{24}N_3O_5Na \cdot 1.5H_2O$: Calcd.: C; 57.39, H; 5.91, N; 9.13 (%) Found: C; 57.34, H; 5.86, N; 8.84 (%)

¹H NMR δ ppm (300 MHz, D₂O); Compound 132 occurs as a mixture of two conformers in heavy water; the signal for the main conformer is shown. 2.49(1H,br s), 2.66(1H,d,J=2.5Hz), 2.84(4H,m), 2.93(3H,s), 3.37(2H,m), 4.96(1H,t,J=7.6Hz), 6.87(2H,d,J=8.5Hz), 7.06(2H,d,J=8.5Hz), 7.36(5H, m)

Working Example 133

N-[N-[(2S,3S)-3-ethoxycarbonylaziridine-2-carbonyl]-L-tyrosyl]-N-methyl-1-naphthalenemethylamine In substantially the same manner as Working Example 2, N-methyl-1-naphthalenemethylamine (877 μl) was condensed with Boc-(O-benzyl)-L-tyrosine (2.00 g) to give N-[Boc-(O-benzyl)-L-tyrosyl]-N-methyl-1-naphthalenemethylamine (2.60 g) as a white powdery product (yield 92%). The Boc group of the product was deprotected by using TFA, and 2.02 g of thus-obtained compound was condensed, in substantially the same manner as Working Example 2, with Compound 1 (1.40 g) to give N-[N-[(2S,3S)-N-Z-3-ethoxycarbonylaziridine-2-carbonyl]-(O-benzyl)-L-tyrosyl]-N-methyl-1-naphthalenemethylamine (1.73 g) as a white powdery product (yield 52%). This compound was subjected to catalytic reduciton to thereby deprotect the Z group and benzyl group in substantially the same manner as Working Example 3 to give the above-titled compound (compound 133; 580 mg) as white crystals (yield 53%).

Elemental Analysis for $C_{27}H_{29}N_3O_5 \cdot 0.9H_2O$: Calcd.: C; 65.95, H; 6.31, N; 8.55 (%) Found: C; 66.41, H; 6.31, N; 8.06 (%)

¹H NMR δ ppm (300 MHz, CDCl₃); Compound 133 occurs as a mixture of two conformers in CDCl₃; the signal for the main conformer is shown. 1.30(3H,t,J=7.0Hz), 2.52 (1H br s), 2.71(3H,s), 2.80(1H,d,J=2.2Hz), 2.84(1H,dd,J=6.3,13.7Hz), 2.96(1H,dd,J=7.6,13.6Hz), 4.22(2H,m), 4.80 (1H,d,J=14.8Hz), 5.13(1H,m), 5.26(1H,d,J=14.9Hz), 6.60 (2H,d,J=8.5Hz), 6.93(2H,d,J=8.5Hz), 7.18(1H,m), 7.40(1H, dd,J=7.1,8.3Hz), 7.52(2H,m), 7.80(1H,m), 7.87(1H,m), 8.04 (1H,m)

Working Example 134

N-[N-[(2S,3S)-3-carboxyaziridine-2-carbonyl]-L-tyrosyl]-N-methyl-1-naphthalenemethylamine Sodium Salt In substantially the same manner as Working Example 4, Compound 133 (180 mg) was subjected to alkali hydrolysis to give the above-titled compound (Compound 134; 130 mg) as a white powdery product (yield 73%).

Elemental Analysis for $C_{25}H_{24}N_3O_5Na \cdot 1.0H_2O$: Calcd.: C; 61.60, H; 5.38, N; 8.62 (%) Found: C; 61.65, H; 5.60, N; 8.35 (%)

¹H NMR δ ppm (300 MHz, D₂O); Compound 134 occurs as a mixture of two conformers in heavy water; the signal for the main conformer is shown. 2.56(1H,d,J=2.6Hz), 2.68(3H, s), 2.82(1H,d,J=2.7Hz), 2.92(2H,m), 4.62(1H,d,J=15.6Hz), 5.04(1H,m), 5.10(1H,d,J=15.7Hz), 6.72(2H,d,J=8.4Hz), 6.91(2H,m), 7.04(2H,d,J=8.5Hz), 7.40(1H,m), 7.57(2H,m), 7.87(2H,m)

Formulation Example

All the following components, including Compound 7 obtained in Example 7, were mixed together and filled in a gelatin capsule to prepare a capsular preparation containing 30 mg of Compound 7.

| Compound 7 | 30 mg |
| --- | --- |
| Lactose | 100 mg |
| Corn starch | 40 mg |
| Magnesium stearate | 10 mg |
| Total | 180 mg |

The compound [I] or salts thereof are used for prophylactic and therapeutic agents for bone diseases such as osteoporosis, hypercalcemia in malignancy and Paget's disease. And, the compound [I] or salts thereof have an activity of inhibiting thiol protease, and are used as prophylactic and therapeutic agents for diseases caused by thiol protease.

What is claimed is:

1. A compound of the formula:

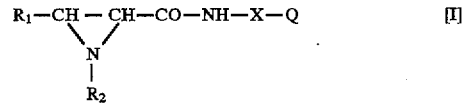

wherein

R₁ and Q are independently a carboxyl group which may be esterified or amidated;

R₂ is hydrogen, an acyl group or a $C_{1-20}$ hydrocarbon residue; and

X is a $C_{1-20}$ divalent hydrocarbon residue;

or a salt thereof.

2. The compound according to claim 1, which is a pharmaceutically acceptable salt.

3. The compound according to claim 1, wherein R₁ or Q is, or both R₁ and Q are, a carboxyl group.

4. The compound according to claim 1, wherein R₁ or Q is, or both R₁ and Q are, an esterified carboxyl group.

5. The compound according to claim 4, wherein R₁ or Q is, or both R₁ and Q are independently, an esterified carboxyl group having the partial structural formula: —COOR₅, wherein R₅ is selected from the group consisting of a $C_{1-6}$ alkyl group optionally having 1 to 3 substituents selected from (a) nitro, (b) halogen and (c) $C_{1-6}$ alkanoyloxy group; a $C_{6-14}$ aryl group; and a $C_{7-12}$ aralkyl group optionally having 1 to 3 substituents selected from (a) nitro, (b) halogen and (c) $C_{1-4}$ alkoxy group.

6. The compound according to claim 1, wherein R₁ or Q is, or both R₁ and Q are independently, an amidated carboxyl group having a partial structural formula: —CONHR₆, wherein R₆ is selected from the group consisting of hydrogen, a $C_{1-6}$ alkyl group, a $C_{1-14}$ aryl group, and a $C_{7-12}$ aralkyl group.

7. The compound according to claim 1, wherein Q is an amidated carboxyl group having the partial structural formula: —CO—N(R₃)(R₄), wherein R₃ and R₄ independently are hydrogen, a $C_{1-20}$ hydrocarbon residue, or a 5- or 6-membered heterocyclic group; or R₃ and R₄ are combined with the adjacent nitrogen atom to form a 5- to 8-membered heterocyclic group.

8. The compound according to claim 7, wherein R₃ or R₄ is, or both R₃ and R₄ are, hydrogen.

9. The compound according to claim 7, wherein R₃ or R₄ is, or both R₃ and R₄ are independently, a hydrocarbon residue selected from the group consisting of a $C_{1-15}$ alkyl group, a $C_{3-12}$ cycloalkyl group, a $C_{2-10}$ alkenyl group, a $C_{2-10}$ alkynyl group, a $C_{3-10}$ cycloalkenyl group, a $C_{6-14}$ aryl group, and a $C_{7-14}$ aralkyl group.

10. The compound according to claim 9, wherein the hydrocarbon residue is substituted with at least one substituent selected from the group consisting of an amino group optionally having one or two substituents selected from (a) $C_{1-4}$ alkyl group, (b) $C_{1-6}$ alkanoyl group, (c) $C_{7-11}$ aroyl group, (d) $C_{2-7}$ alkoxycarbonyl group, (e) $C_{8-12}$ aralkyloxycarbonyl group, (f) $C_{1-6}$ alkylsulfonyl group and (g) $C_{6-12}$ arylsulfonyl group; a hydroxyl group optionally having a substituent selected from (a) $C_{1-4}$ alkyl group, (b) $C_{7-12}$ aralkyl group, (c) $C_{1-6}$ alkanoyl group and (d) $C_{7-11}$ aroyl group; a mercapto group optionally having a substituent selected from (a) $C_{1-4}$ alkyl group and (b) $C_{6-10}$ aryl group; a carboxyl group; a carbamoyl group; a $C_{2-5}$ alkoxycarbonyl group; a $C_{8-14}$ aralkyloxycarbonyl group; a 5- or 6-membered heterocyclic group; a nitro group, a cyano group; halogen atom, a guanidyl group; an amidino group; and a $C_{3-8}$ cycloalkyl group.

11. The compound according to claim 7, wherein the 5- or 6-membered heterocyclic group is substituted with at least one substituent selected from the group consisting of a $C_{1-4}$ alkyl group, a $C_{6-14}$ aryl group, a $C_{7-12}$ aralkyl group, a hydroxyl group, a carboxyl group, a carbamoyl group, a $C_{2-5}$ alkoxycarbonyl group, a nitro group and a halogen atom.

12. The compound according to claim 7, wherein the 5- to 8-membered heterocyclic group is substituted with at least one substituent selected from the group consisting of a $C_{1-4}$ alkyl group, a $C_{6-14}$ aryl group, a $C_{7-12}$ aralkyl group, a hydroxyl group, a carboxyl group, a carbamoyl group, a $C_{2-5}$ alkoxycarbonyl group, a nitro group and a halogen atom.

13. The compound according to claim 7, wherein either $R_3$ or $R_4$ is hydrogen and the other is a $C_{1-20}$ hydrocarbon residue.

14. The compound according to claim 13, wherein the hydrocarbon residue is an alkyl group.

15. The compound according to claim 13, wherein the hydrocarbon residue is an aralkyl group.

16. The compound according to claim 7, wherein the 5- to 8-membered heterocyclic group is a 6-membered heterocyclic group.

17. The compound according to claim 1, wherein $R_2$ is hydrogen.

18. The compound according to claim 1, wherein $R_2$ is an acyl group.

19. The compound according to claim 18, wherein $R_2$ is an acyl group selected from the group consisting of a formyl group, a $C_{2-6}$ alkanoyl group, a $C_{7-11}$ aroyl group, a $C_{2-7}$ alkoxycarbonyl group, a $C_{7-11}$ aryloxycarbonyl group, a $C_{8-13}$ aralkylcarbonyl group, and a $C_{8-13}$ aralkyloxycarbonyl group.

20. The compound according to claim 1, wherein $R_2$ is a hydrocarbon residue selected from the group consisting of a $C_{1-15}$ alkyl group, a $C_{3-12}$ cycloalkyl group, a $C_{2-10}$ alkenyl group, a $C_{2-10}$ alkynyl group, a $C_{3-10}$ cycloalkenyl group, a $C_{6-14}$ aryl group, and a $C_{7-14}$ aralkyl group.

21. The compound according to claim 20, wherein the hydrocarbon residue is substituted with at least one substituent selected from the group consisting of an amino group, a hydroxyl group, a mercapto group, a carboxyl group, a carbamoyl group, a $C_{2-5}$ alkoxycarbonyl group, a $C_{8-14}$ aralkyloxycarbonyl group, a 5- or 6-membered heterocyclic group, a nitro group, a cyano group, halogen atom, a guanidyl group, an amidino group, and a $C_{3-8}$ cycloalkyl group.

22. The compound according to claim 1, wherein X is a $C_{1-20}$ divalent aliphatic hydrocarbon residue.

23. The compound according to claim 1, wherein the $C_{1-20}$ divalent hydrocarbon residue is substituted with at least one substituent selected from the group consisting of an amino group, a hydroxyl group, a mercapto group, a carboxyl group, a carbamoyl group, a $C_{2-5}$ alkoxycarbonyl group, a $C_{8-14}$ aralkyloxycarbonyl group, a 5- or 6-membered heterocyclic group, a nitro group, a cyano group, a halogen atom, a guanidyl group, an amidino group, a $C_{6-14}$ aryl group, and a $C_{3-8}$ cycloalkyl group.

24. The compound according to claim 1, wherein the partial structural formula: —NH—X—CO— is an α-amino acid residue.

25. The compound according to claim 24, wherein the α-amino acid residue is in an L-configuration.

26. The compound according to claim 24, wherein the α-amino acid residue is an aromatic amino acid residue.

27. N-(N-((2S,3S)-3-ethoxycarbonylaziridine-2-carbonyl)-L-phenylalanyl)-2-phenylethylamine.

28. N-(N-((2S,3S)-3-ethoxycarbonylaziridine-2-carbonyl)-L-phenylalanyl)isopentylamine.

29. N-(N-((2S,3S)-3-ethoxycarbonylaziridine-2-carbonyl)-L-phenylalanyl)-3-methoxypropylamine.

30. N-(N-((2S,3S)-3-ethoxycarbonylaziridine-2-carbonyl)-L-phenylalanyl)-N-methyl-2-phenylethylamine.

31. A composition which comprises the compound or a salt thereof according to claim 1.

32. A pharmaceutical composition which comprises the compound or a pharmaceutical acceptable salt thereof according to claim 1 with a pharmaceutically acceptable carrier, excipient or diluent.

33. A method for inhibiting a thiol protease in a mammal, which comprises administering an effective amount of the compound or a pharmaceutically acceptable salt thereof according to claim 1 to the mammal.

34. The method according to claim 33, wherein the thiolprotease is selected from cathepsins and calpains.

35. A method for treating a bone disease in a mammal, which comprises administering an effective amount of the compound or a pharmaceutically acceptable salt thereof according to claim 1 to the mammal.

36. The method according to claim 35, wherein the bone disease is osteoporosis.

37. A method for preventing a bone disease in a mammal, which comprises administering an effective amount of the compound or a pharmaceutically acceptable salt thereof according to claim 1 to the mammal, wherein the bone disease is selected from the group consisting of osteoporosis, Paget's disease and hypercalcemia in malignancy.

* * * * *